United States Patent
Stokes et al.

(10) Patent No.: US 10,889,582 B2
(45) Date of Patent: Jan. 12, 2021

(54) 1H-PYRROLO [2,3-B] PYRIDINE DERIVATIVES AND THEIR USE AS KINASE INHIBITORS

(71) Applicant: Vernalis (R&D) Limited, Winnersh (GB)

(72) Inventors: Stephen Stokes, Winnersh (GB); Christopher John Graham, Winnersh (GB); Stuart Christopher Ray, Winnersh (GB); Emma Jayne Stefaniak, Winnersh (GB)

(73) Assignee: Vernalis (R&D) Limited, Winnersh (GB)

( * ) Notice: Subject to any disclaimer, the term of this patent is extended or adjusted under 35 U.S.C. 154(b) by 0 days.

(21) Appl. No.: 16/009,439

(22) Filed: Jun. 15, 2018

(65) Prior Publication Data
US 2018/0362526 A1  Dec. 20, 2018

Related U.S. Application Data

(63) Continuation of application No. 14/375,353, filed as application No. PCT/GB2013/050212 on Jan. 30, 2013, now Pat. No. 10,000,481.

(30) Foreign Application Priority Data

Jan. 30, 2012  (GB) .................................. 1201566.5

(51) Int. Cl.
| | | |
|---|---|---|
| A61K 45/06 | (2006.01) | |
| C07D 471/04 | (2006.01) | |
| A61K 31/437 | (2006.01) | |
| A61K 31/4545 | (2006.01) | |

(52) U.S. Cl.
CPC .......... *C07D 471/04* (2013.01); *A61K 31/437* (2013.01); *A61K 31/4545* (2013.01); *A61K 45/06* (2013.01)

(58) Field of Classification Search
CPC .................................................... A61K 45/06
See application file for complete search history.

(56) References Cited

U.S. PATENT DOCUMENTS

| | | | |
|---|---|---|---|
| 8,569,295 | B2 | 10/2013 | Chen |
| 10,000,481 | B2 | 6/2018 | Stokes et al. |

FOREIGN PATENT DOCUMENTS

| | | |
|---|---|---|
| JP | 2011-510055 A | 3/2011 |
| JP | 2011-522888 A | 8/2011 |
| WO | WO 2003/028724 A1 | 4/2003 |
| WO | WO 2009/089352 A1 | 7/2009 |
| WO | WO 2009/093012 A1 | 7/2009 |
| WO | WO 2009/140320 A1 | 11/2009 |
| WO | WO 2009/151589 A1 | 12/2009 |
| WO | WO 2011/146313 A1 | 11/2011 |

OTHER PUBLICATIONS

Fabian "A small molecule-kinase interaction map for clinical kinase inhibitors" Nature Biotechnology 2005, 23, 329-336.*
Simone, Oncology: Introduction, Cecil Textbook of Medicine, 20th Edition, 1996 vol. 1, pp. 1004-1010.*
Garson "Models of ovarian cancer—Are we there yet?" Molecular and Cellular Endocrinology 239 (2005) 15-26.*
Sale "Models of ovarian cancer metastasis: Murine models" Drug Discovery Today: Disease Models 2006, 3, 150-154.*
Fattaneh A. Tavassoli and Peter Devilee "World Health Organization Classification of Tumours: Pathology and Genetics of Tumours of the Breast and Female Genital Organs" Online "http://www.iarc.fr/en/publications/pdfs-online/pat-gen/bb4/BB4.pdf" accessed Nov. 4, 2016 IARCPress Lyon, 2003.*
Hudis "Triple-Negative Breast Cancer: An Unmet Medical Need" The Oncologist 2011;16(suppl 1):1-11.*
Gerratana "Do platinum salts fit all triple negative breast cancers?" Cancer Treatment Reviews 48 (2016) 34-41.*
Vardiman "The World Health Organization (WHO) classification of the myeloid neoplasms" Blood (2002), 100(7), 2292-2302.*
Pui "Treatment of Acute Lymphoblastic Leukemia" New England Journal of Medicine 2006, 354, 166-78.*
FS14 Myelofibrosis Facts I p. 1 Revised Apr. 2012, pp. 1-9.*
Howington "Treatment of Stage I and II Non-small Cell Lung Cancer Diagnosis and Management of Lung Cancer, 3rd ed: American College of Chest Physicians Evidence-Based Clinical Practice Guidelines" Chest 2013; 143(5)(Suppl):e278S-e313S.*
Socinski "Treatment of Stage IV Non-small Cell Lung Cancer Diagnosis and Management of Lung Cancer, 3rd ed: American College of Chest Physicians Evidence-Based Clinical Practice Guideline" CHEST 2013; 143(5)(Suppl):e341S-e368S.*
Jett Treatment of Small Cell Lung Cancer Diagnosis and Management of Lung Cancer, 3rd ed: American College of Chest Physicians Evidence-Based Clinical Practice Guidelines CHEST 2013; 143(5)(Suppl):e400S-e419S.*
Balamuth "Ewing's sarcoma" Lancet Oncology (2010), 11(2), 184-192.*

(Continued)

*Primary Examiner* — David K O'Dell
(74) *Attorney, Agent, or Firm* — Wolf, Greenfield & Sacks, P.C.

(57) ABSTRACT

The inventions relates to compounds of (I) and therapeutic uses thereof: (I) The terms Z, Y, and $R^1$ are as defined in the claims.

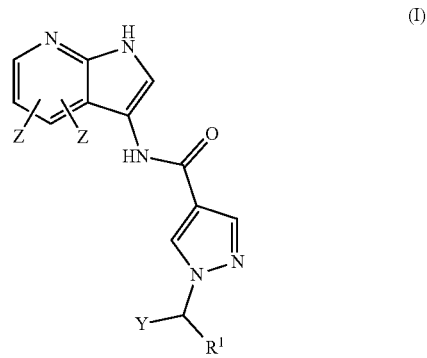

(I)

19 Claims, No Drawings

(56) References Cited

OTHER PUBLICATIONS

Schober "New Advances in the Treatment of Metastatic Pancreatic Cancer" Digestion 2015;92:175-184.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Patil "Checkpoint kinase 1 in DNA damage response and cell cycle regulation" Cell Mol Life Sci. Nov. 2013 70(21), 4009-4021.*
Manic "Trial Watch: Targeting ATM-CHK2 and ATR-CHK1 pathways for anticancer therapy" Molecular & Cellular Oncology, 2015, 2:4, e1012976.*
Chaichian "Targeted Therapies in Systemic Lupus Erythematosus: A State-of-the-Art Review" J Clin Cell Immunol 2013, S6, 1-8.*
Georg Pilz, "Modern multiple sclerosis treatment—what is approved, what is on the horizon" Drug Discovery Today Dec. 2008, vol. 13, Nos. 23/24 1013-1025.*
A.M. Bendele "Animal models of rheumatoid arthritis" J Musculoskel Neuron Interact 2001; 1(4):377-385.*
Ben Dele, "Animal Models of Arthritis: Relevance to Human Disease" Toxicol Pathol 1999 27: 134-142.*
International Search Report and Written Opinion dated May 7, 2013 in connection with PCT/GB2013/050212.
Bohm et al., Scaffold hopping. Drug Discovery Today: Technologies. 2004;1(3):217-24. doi: 10.1016/j.ddtec.2004.10.009.
Arora et al., RNAi screening of the kinome identifies modulators of cisplatin response in ovarian cancer cells. Gynecol Oncol. Sep. 2010;118(3):220-7. doi: 10.1016/j.ygyno.2010.05.006.
Brooks et al., A potent Chk1 inhibitor is selectively cytotoxic in melanomas with high levels of replicative stress. Oncogene. Feb. 7, 2013;32(6):788-96. doi: 10.1038/onc.2012.72. Epub Mar. 5, 2012.
Bryant et al., Chk1 Inhibition as a novel therapeutic strategy for treating triple-negative breast and ovarian cancers. BMC Cancer. Aug. 7, 2014;14:570. doi: 10.1186/1471-2407-14-570.
Dafau et al., Multicellular tumor spheroid model to evaluate spatio-temporal dynamics effect of chemotherapeutics: application to the gemcitabine/CHK1 inhibitor combination in pancreatic cancer. BMC Cancer. Jan. 13, 2012;12:15. doi: 10.1186/1471-2407-12-15.
Guzi et al., Targeting the Replication Checkpoint Using SCH 900776, a Potent and Functionally Selective CHK1 Inhibitor Identified via High Content Screening. Mol Cancer Ther. Apr. 2011;10(4):591-602. doi: 10.1158/1535-7163.MCT-10-0928.
Mitchell et al., Simultaneous exposure of transformed cells to SRC family inhibitors and CHK1 inhibitors causes cell death. Cancer Biol Ther. Aug. 1, 2011;12(3):215-28. doi: 10.4161/cbt.12.3.16218.
Morgan et al., Mechanism of Radiosensitization by the Chk1/2 Inhibitor AZD7762 Involves Abrogation of the G2 Checkpoint and Inhibition of Homologous Recombinational DNA Repair. Cancer Res. Jun. 15, 2013;70(12):4972-81. doi: 10.1158/0008-5472.CAN-09-3573.
Russell et al., Combination Therapy Targeting the Chk1 and Wee1 Kinases Shows Therapeutic Efficacy in Neuroblastoma. Cancer Res. Jan. 15, 2013;73(2):776-84. doi: 10.1158/0008-5472.CAN-12-2669. Epub Nov. 7, 2012.
Shibata et al., Response of subtype-specific human breast cancer-derived cells to poly (ADP-ribose) polymerase and checkpoint kinase 1 inhibition. Cancer Sci. Oct. 2011;102(10):1882-8. doi: 10.1111/j.1349-7006.2011.02016.x. Epub Jul. 21, 2011.
Walton et al., CCT244747 Is a Novel Potent and Selective CHK1 Inhibitor with Oral Efficacy Alone and in Combination with Genotoxic Anticancer Drugs. Clin Cancer Res. Oct. 15, 2012;18(20):5650-61. doi: 10.1158/1078-0432.CCR-12-1322. Epub Aug. 28, 2012.
Xu et al., Checkpoint kinase inhibitor synergizes with DNA-damaging agents in G1 checkpoint-defective neuroblastoma. Int J Cancer. Oct. 15, 2011;129(8):1953-62. doi: 10.1002/ijc.25842. Epub Mar. 8, 2011.
Zabludoff et al., AZD7762, a novel checkpoint kinase inhibitor, drives checkpoint abrogation and potentiates DNA-targeted therapies. Mol Cancer Ther. Sep. 2008;7(9):2955-66. doi: 10.1158/1535-7163.MCT-08-0492.
Zhang et al., Checkpoint Controls and Targets in Cancer Therapy. Published Sep. 7, 2009. Humana Press, Eds. p. 254, Section 16.7.2.1, A-776574.

* cited by examiner

1H-PYRROLO [2,3-B] PYRIDINE DERIVATIVES AND THEIR USE AS KINASE INHIBITORS

RELATED APPLICATIONS

The present application is a Continuation application of U.S. application Ser. No. 14/375,353, filed Jul. 29, 2014 (allowed), which is a National Stage filing under 35 U.S.C. § 371 of International PCT Application No. PCT/GB2013/050212, filed Jan. 30, 2013, which claims priority to United Kingdom Patent Application, GB 1201566.5, filed Jan. 30, 2012, each of which is incorporated herein by reference.

FIELD OF INVENTION

This invention relates to novel 1H-pyrrolo[2,3-b]pyridine derivatives having checkpoint kinase 1 (CHK1) inhibitory activity, to the use of such compounds in medicine, in relation to the treatment of cancer, via the inhibition of aberrant cell proliferation, and to pharmaceutical compositions containing such compounds.

BACKGROUND OF THE INVENTION

DNA damaging cytotoxic chemotherapeutic agents and ionizing radiation are the mainstay of current cancer treatment regimens. These therapies are effective, especially when administered in combinations, against a wide variety of neoplasms and are likely to remain the standard of care for cancer treatment for the foreseeable future. These agents, due to their mechanism of action, have limitations which restrict their overall effectiveness. As these agents target DNA, they are effective against any cell especially those actively replicating and therefore lack tumor cell specificity. Administration is usually at the maximum tolerated dose (MTD) resulting in a narrow therapeutic index and toxicity to normal tissue especially those with an actively dividing cell component such as the gastrointestinal tract, hematological system and other organs. Acquired or intrinsic resistance can further limit the usefulness of these agents making many patients' tumors refractory to the drug. Multiple mechanisms can contribute to acquired resistance including reduced cellular levels of active drug (through increased metabolism, detoxification or active efflux), increased DNA repair, loss of p53 or attenuation of apoptotic signaling.

Despite inducing DNA damaging through multiple mechanisms (e.g. topoisomerase inhibition, direct DNA alkylation or reduction of deoxyribonucleotides), DNA damaging cytotoxic chemotherapeutic agents such as cisplatin, irinotecan or gemcitabine activate cell cycle checkpoints. Cell cycle checkpoints exist to protect the fidelity of DNA replication and division, and ensure the correct timing of cell cycle events. As DNA cannot be replaced, these pathways are critical in protecting genomic integrity and preventing the onset of cancer. Checkpoints exist at multiple phases of the cell cycle and can be activated during the G1-, S- or G2-phase of the cell cycle in response to DNA damage.

Alternatively, the mitotic checkpoint is activated by improper chromosome attachment to a bipolar spindle and exists to ensure accurate chromosome segregation and protect against aneuploidy. In mammalian cells, the key effector proteins are p53 and the checkpoint kinases Chk1 and Chk2. A large proportion of human cancers are defective for the p53-pathway in some form thereby lacking a functional G1 checkpoint. Therefore, these human tumors are highly reliant on the Chk kinases to protect them in response to DNA damaging insults.

DNA damaging agents, along with ionizing radiation, activate DNA damage checkpoints and induce cell cycle arrest in G1, S, or at the G2-M transition.

Damage sensors, such as the Mre11 complex (Mre11, Rad50 and Nbs1) that recognize double strand breaks, or the Rad17 and the Rad9-Hus1-Rad1 complex that recognize replication stress, activate the central transducing kinases ATM and ATR. In turn, these kinases directly activate the effector kinases Chk1 and Chk2. Chk1 and Chk2 negatively regulate the Cdc25 family of phosphatases thereby preventing cell cycle progression as well as directly modulating repair proteins resulting in increased lesion repair. This allows the cell to pause replication, repair the damaged DNA, then resume replication. Biochemical and genetic studies have demonstrated Chk1 to be essential and indispensible for the S- and G2-M checkpoints.

Chk1 inhibition, therefore, represents a novel therapeutic strategy to increase the lethality of DNA-damaging chemotherapeutic drugs in p53 pathway defective cancers. Abrogation of the remaining intact checkpoint should result in increased tumor cell death. Chk1 inhibitors have demonstrated potentatiation of a range of cytotoxic chemotherapy drugs both in vitro and in a range of pre-clinical models of human cancer including gemcitabine, irinotecan and paclitaxel. This 'synthetic lethality' approach should increase the therapeutic activity of the chemotherapeutic drug without increasing the systemic toxicity as normal cells should remain protected by their functional p53 pathway. Chk1 inhibitors have, therefore, the potential to be combined with a wide range of cytotoxic chemotherapeutic agents for the treatment of a diverse selection of human cancers. This approach has started to be tested clinically with several small molecule inhibitors of Chk1 (GDC0425, GDC0575, LY2603618 and LY2606368) currently undergoing Phase I/II clinical evaluation in combination with gemcitabine, irinotecan and cytarabine. Additional agents including AZD7762, PF00477736, SCH900776 and XL844 have undergone Phase I trials but the development of these agents has subsequently been stopped.

WO2009140320 and WO2009089352 disclose pyrrolopyridines as CHK1 and/or CHK2 inhibitors.

It has now been found that certain 1H-pyrrolo[2,3-b]pyridine derivatives show efficacy as CHK1 inhibitors.

SUMMARY OF THE INVENTION

The present invention relates to a class of substituted 1H-pyrrolo[2,3-b]pyridine compounds useful as CHK1 inhibitors, for example, for the treatment of cancer. A core 1H-pyrrolo[2,3-b]pyridine template, with optional substitution in the 4 and position and in the three position by a substituted-pyrazolyl amido-linked group are principle characterising features of the compounds with which the invention is concerned.

The present invention is a compound of formula I:

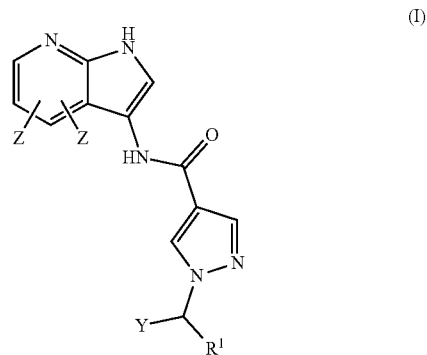

or a pharmaceutically acceptable salt thereof, wherein:

each Z is independently $(Alk)_n-R-(Alk)_n-X$, wherein each Alk is independently ($C_1$ to $C_{12}$) alkylene or ($C_2$ to $C_{12}$) alkenylene, each of which may be optionally substituted;

each n is independently 0 or 1;

each R is independently optionally substituted arylene or heteroarylene, or optionally substituted cycloalkylene or heterocyclic, —O—, —S—, —(C=O)—, —(C=S)—, —SO$_2$—, —C(=O)O—, —C(=O)NR$^A$—, —C(=S)NR$^A$—, —SO$_2$NR$^A$—, —NR$^A$C(=O)—, —NR$^A$SO$_2$— or —NR$^A$— wherein $R^A$ is hydrogen, $C_1$-$C_6$ alkyl, —$C_1$-$C_6$ alkyl(cycloalkyl), $C_1$-$C_6$ alkyl($C_1$-$C_6$ alkoxy) or $C_1$-$C_6$ alkoxy;

each X is independently halogen, —H, —OR$^A$, NR$^A$R$^A$, optionally substituted aryl or heteroaryl, or optionally substituted cycloalkyl or heterocyclic, CN or C(halogen)$_a$H$_b$, where a is 1, 2, or 3, and b is (3-a);

Y is optionally substituted aryl or heteroaryl, or optionally substituted cycloalkyl or heterocyclic; and $R^1$ is H or $C_1$-$C_6$ alkyl.

DESCRIPTION OF PREFERRED EMBODIMENTS

Terminology

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "($C_a$-$C_b$)alkylene" wherein a and b are integers refers to a saturated hydrocarbon chain having from a to b carbon atoms and two unsatisfied valences, such as —CH$_2$—, —CH$_2$CH$_2$—, —CH$_2$CH$_2$CH$_2$—, —CH$_2$CH(CH$_3$)CH$_2$— and —CH$_2$C(CH$_3$)$_2$CH$_2$—. For the avoidance of doubt, it is to be understood that a divalent branched chain ($C_a$-$C_b$)alkylene radical includes those wherein one of the carbons of the hydrocarbon chain is a ring carbon of a cycloalkyl ring (ie is a spiro centre).

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "carbocyclic" refers to a mono- or bi-cyclic radical whose ring atoms are all carbon, and includes monocyclic aryl, cycloalkyl, and cycloalkenyl radicals, provided that no single ring present has more than 8 ring members. A "carbocyclic" group includes a mono-bridged or multiply-bridged cyclic alkyl group.

As used herein the term "aryl" refers to a mono-, bi- or tri-cyclic carbocyclic aromatic radical. Illustrative of such radicals are phenyl, biphenyl and napthyl.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular refers to a mono-, bi- or tri-cyclic non-aromatic radical containing one or more heteroatoms selected from S, N and O, to groups consisting of a monocyclic non-aromatic radical containing one or more such heteroatoms which is covalently linked to another such radical or to a monocyclic carbocyclic radical, and to a mono-, bi- or tri-cyclic non-aromatic radical containing one or more heteroatoms selected from S, N and O which is mono-bridged or multiply-bridged. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with at least one substituent, for example selected from ($C_1$-$C_6$)alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, halo (including fluoro and chloro), trifluoromethyl, trifluoromethoxy, nitro, nitrile (—CN), oxo, phenyl, —COOH, —COOR$^A$, —COR$_A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NH$^B$COOR$^A$, —NR$^B$COOR$^A$. —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein $R^A$ and $R^B$ are independently a ($C_1$-$C_6$)alkyl group, or $R^A$ and $R^B$ when attached to the same nitrogen may form a cyclic amino ring such as a morpholinyl, piperidinyl or piperazinyl ring. An "optional substituent" or "substituent" may be one of the foregoing substituent groups.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides, alkaline earth metal hydroxides e.g. calcium, barium and magnesium hydroxides, with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

For a review on suitable salts, see Handbook of Pharmaceutical Salts: Properties, Selection. and Use by Stahl and Wermuth (Wiley-VCH, Weinheim, Germany, 2002).

Compounds of the invention are expected to be isolatable as hydrates and solvates. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is H$_2$O. Any reference herein to a compound of formula (I) is to be understood as including such hydrates and solvates.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

So-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H. Bundgaard (Elsevier, 1985).

Also included within the scope of the invention are metabolites of compounds of formula (I), that is, compounds formed in vivo upon administration of the drug. Some examples of metabolites include (i) where the compound of formula (I) contains a methyl group, an hydroxymethyl derivative thereof (—CH$_3$—>—CH$_2$OH):
(ii) where the compound of formula (I) contains an alkoxy group, an hydroxy derivative thereof (—OR—>—OH),
(iii) where the compound of formula (I) contains a tertiary amino group, a secondary amino derivative thereof (—NR$^1$R$^2$—>—NHR$^1$ or —NHR$^2$),
(iv) where the compound of formula (I) contains a secondary amino group, a primary derivative thereof (—NHR$^1$—>—NH$^2$),
(v) where the compound of formula (I) contains a phenyl moiety, a phenol derivative thereof (-Ph->-PhOH), and
(vi) where the compound of formula (I) contains an amide group, a carboxylic acid derivative thereof (—CONH$_2$>COOH).

PREFERRED EMBODIMENTS

Variable substituents present in compounds (I) will now be further described. It is to be understood in the further description that any disclosed substituent or substituent class may be present in any combination with any of the other disclosed substituent classes. Specific examples of the variable substituents include those present in the compounds of the Examples herein.

Preferably, the group "alk" is (C$_1$ to C$_6$) alkylene or (C$_2$ to C$_6$) alkenylene.

Preferably, at least one of the "Z" groups is located on either the 4- or 5-position of the pyridine ring. More preferably, at least one Z group is located on the 5-position of the ring. Most preferably, the Z groups are located on the 4- and 5-positions of the ring.

Preferably, X and/or Z is a solubilising group. Many such solubilising groups are known in medicinal chemistry. Examples of solubilising groups are morpholinyl, piperidinyl, piperazinyl, pyrrolidinyl, ethylamino, isopropylamino, diethylamino, cyclohexylamino, cyclopentylamino, methoxyethylamino, piperidin-4-yl, N-acetylpiperazinyl, methylsulfonylamino, thiomorpholinyl, thiomorpholinyldioxide, 4-hydroxyethylpiperidinyl, and 4-hydroxypiperidinyl.

In a preferred embodiment Y is phenyl or heteroaryl optionally substituted with C$_1$ to C$_6$ alkyl, OR$^A$, halogen or C$_1$ to C$_6$ alkoxy. More preferably Y is pyridyl, pyrrolyl, phenyl, or phenyl substituted with methyl, O-methyl, bromine or chlorine.

In a yet further preferred embodiment, Y is optionally substituted aryl. Preferably, Y is optionally substituted phenyl More preferably, Y is unsubstituted phenyl.

Preferably, a compound of the invention is according to one of the specific examples, or a pharmaceutically acceptable salt thereof.

R$^1$ is preferably H or Me. More preferably, R$^1$ is H.

R$^A$ is preferably is H or C$_1$-C$_6$ alkyl. In an embodiment R$^A$ is —C$_1$-C$_6$ alkyl(cycloalkyl) such as —CH$_2$-cyclopropyl, —CH$_2$-cyclopentyl or —CH$_2$— cyclohexyl.

In an embodiment at least one Z is H, halogen, optionally substituted aryl, optionally substituted heteroaryl, optionally substituted nitrogen-containing heterocycle, C$_1$ to C$_6$ alkyl or OR$^A$. In a particularly preferred embodiment the optional substituent on the nitrogen-containing heterocycle is NR$^A$R$^A$.

In a preferred embodiment one Z group is H, halogen, OR$^A$ or C$_1$ to C$_6$ alkyl, and the other Z group is optionally substituted aryl or optionally substituted nitrogen-containing heterocycle. In a particularly preferred embodiment the optional substituent on the nitrogen-containing heterocycle is NR$^A$R$^A$.

In a preferred embodiment Z is (Alk)$_n$-optionally substituted arylene-(Alk)$_n$-optionally substituted heterocycle.

In an alternative preferred embodiment Z is optionally substituted heteroaryl or optionally substituted nitrogen-containing heterocycle.

In a preferred embodiment, the compounds of the invention are according to formula (Ia):

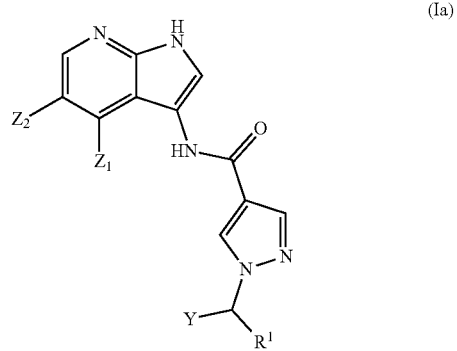

(Ia)

or a pharmaceutically acceptable salt thereof, wherein:
Z$_1$ and Z$_2$ are independently (Alk)$_n$-R$_n$-(Alk)$_n$-X; and
Alk, n, R, X, Y, R$^A$ and R$^1$ are as defined in claim 1.

Preferably in the compound of formula (Ia) Z$_2$ is halogen, phenyl, OR$^A$ or C$_1$ to C$_6$ alkyl, and Z$_2$ is optionally substituted aryl or optionally substituted heterocycle.

Preferably in the compound of formula (Ia) Z$_2$ is halogen, CF$_3$, cyclopropyl, phenyl, OR$^A$ or C$_1$ to C$_6$ alkyl, and Z$_1$ is optionally substituted aryl or optionally substituted heterocycle.

Preferably the terms "heterocycle" or "nitrogen-containing heterocycle" when used in the context of compounds of formula (I) or (Ia) represent an optionally substituted piperidine, piperazine or morpholine ring.

In an embodiment $Z_1$ is R—X, and $Z_2$ is X.
In an alternative embodiment $Z_2$ is R—X, and $Z_2$ is X.
In a further embodiment $Z_1$ is R-Alk-X, and $Z_2$ is X.
In a yet further embodiment $Z_2$ is R-Alk-X, and $Z_2$ is X.

Utility

The present invention may be employed in respect of a human or animal subject, more preferably a mammal, more preferably a human subject.

As used herein, the term "treatment" as used herein includes prophylactic treatment.

Compounds of the invention may be used alone in the treatment of cancers and autoimmune disorders such as organ transplant rejection, lupus, multiple sclerosis, rheumatoid arthritis and osteoarthritis. Inhibitors of CHK1 have demonstrated utility in improving the efficacy of current DNA-damage inducing radiotherapy or chemotherapeutic regimens for cancer treatment. The compound of formula (I) can be used in combination for the treatment of cancer with radiation therapy or one or more cytotoxic or cytostatic drugs, or drugs which induce cytotoxicity or cytostasis. The compound of the invention and the other component (may be in the same pharmaceutical formulation or in separate formulations for administration simultaneously or sequentially.

Non-limiting examples of chemotherapeutic agents, radiotherapic agents and other active and ancillary agents are set forth below.

(i) Alkylating agents.
(ii) Nitrogen mustards such as
Chlorambucil
Cyclophosphamide
Ifosfamide
Mechlorethamine
Melphalan
(iii) Nitrosoureas Such as
carmustine (BCNU)
lomustine (CCNU)
semustine (methyl-CCNU)
(iv) Ethylenimine/Methyl-melamine such as
hexamethylmelamine (HMM/altetamine)
thriethylenemelamine (TEM)
trethylene thiophosphoramide (thiotepa)
(v) Alkyl sulphonates such as busulphan.
(vi) Triazines such as dacarbazine (DTIC).
(vii) Antimetabolites such as the Folic acid analogues such as
Methoxtrexate
pemetrexed (multi-targeted antifolate)
Tnmetrexate
(viii) Pyrimidine analogues such as
2,2'-difluorodeoxy-cytidine
5-azacytidine
5-fluorouracil
cytosine arabinoside (araC/cytarabine)
Fluorodeoxyuridine
Gemcitabine
(ix) Purine analogues such as
2-chlorodeoxyadenosine (cladribine/2-CdA)
2'-deoxycoformycin (pentostatin)
6-Mercaptopurine
6-thioguanine
Azathioprine
erthyrohydroxynonyl-adenine (EHNA)
fludarabine phosphate
(x) Type I Topoisomerase Inhibitors such as
Camptothecin
Irinotecan
Topotecan
(xi) Biological response modifiers such as G-CSF and GM-CSF.
(xii) Differentiation agents such as retinoic acid derivatives.
(xiii) Hormones and antagonists.
(xiv) Adrenocorticosteroids/antagonists such as
Ainoglutethimide
Dexamethasone
prednisone and equivalents
(xv) Progestins such as
hydroxyprogesterone caproate
medroxyprogesterone acetate
megestrol acetate
(xvi) Estrogens such as
Diethylstilbestrol
ethynyl estradiol/equivalents
(xvii) Antiestrogens such as tamoxifen.
(xviii) Andogens such as
testosterone propionate
fluoxymesterone/equivalents
(xix) Anti-androgens such as
Flutimide
gonadotropin-releasing hormone analogues
Leuprolide
(xx) Nonsteroidal antiandrogens.
(xxi) Natural products.
(xxii) Antimitotic drugs.
(xxiii) Taxanes such as
docetaxel (Taxotere)
estramustine/estramustine phosphate
Paclitaxel
vinblastine (VLB)
vinca alkaloids
Vincristine
Vinorelbine
(xxiv) Epipodophylotoxins such as etoposide or teniposide.
(xxv) Antibiotics such as
actimomycin D
aphidicolin
Bleomycin
Dactinomycin
daunomycin (rubidomycin)
doxorubicin (adriamycin)
mitomycin C
Mitroxantroneidarubicin
splicamycin (mithramycin)
(xxvi) Enzymes such as L-asparaginase and L-arginase.
(xxvii) Radiosensitizers such as
5-bromodeozyuridine
5-idoddeoxyuridine
Bromodeoxycytidine
Desmethylmisonidazole
EO9
Etanidazole
Metronidazole
Misonidazole
Nicotinamide
Nimorazole
Pimonidazole
RB 6145
RSU 1069
SR4233

(xxviii) Platinum coordination complexes such as
Anthracenedione
Carboplatin
Cisplatin
Mitoxantrone
oxaliplatin
(xxix) Substituted ureas such as hydroxyurea.
(xxx) Methyhydrazine derivatives such as N-methylhyrazine (MIH) and
procarbazine.
(xxxi) Adrenocortical suppressant mitocane (o,p'-DDD) ainoglutethimide.
(xxxii) Cytokines such as interferon ($\alpha$, $\beta$, $\gamma$) and interleukin-2.
(xxxiii) Photosensitisers such as
bacteriochlorophyll-a
benzoporphyrin denvatives
hematoporphyrin derivatives
napthalocyanines
Npe6
pheboride-a
photofrin
phthalocyanines
tin etioporphyrin (SnET2)
zinc phthalocyanines
(xxxiv) Radiation such as
gamma radiation
infrared radiation
microwave radiation
ultraviolet light
visible light
X-ray
(xxxv) Molecular targeted therapeutics
mTOR inhibitors
PI3 Kinase inhibitors
MEK inhibitors
Wee1 inhibitors CHK1 inhibitors have recently shown preclinical activity as single agents in a diverse range of human cancers including but not limited to ovarian cancer, triple negative breast cancer, neuroblastoma, melanoma, pancreatic cancer, hematological cancers and cancers with defects in DNA repair pathways such as Fanconi's Anaemia.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg, once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone, fillers for example lactose, sugar, maize-starch, calcium phosphate, sorbitol or glycine, tabletting lubricant, for example magnesium stearate, talc, polyethylene glycol or silica, disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with $H_2O$ or other suitable vehicle before use. Such liquid preparations may contain conventional additives such as suspending agents, for example sorbitol, syrup, methyl cellulose, glucose syrup, gelatin hydrogenated edible fats, emulsifying agents, for example lecithin, sorbitan monooleate, or acacia, non-aqueous vehicles (which may include edible oils), for example almond oil, fractionated coconut oil, oily esters such as glycerine, propylene glycol, or ethyl alcohol, preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia. The active ingredient may also be administered parenterally in a sterile medium.

Depending on the vehicle and concentration used, the drug can either be suspended or dissolved in the vehicle. Advantageously, adjuvants such as a local anaesthetic, preservative and buffering agents can be dissolved in the vehicle.

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "Advanced organic chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein". Such literature methods include those of the preparative Examples herein, and methods analogous thereto.

Examples of methods known in the art of organic chemistry in general, by which the compounds of the present invention may be prepared, are included in the following reaction schemes and procedures.

Scheme 1

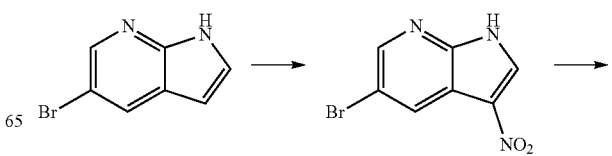

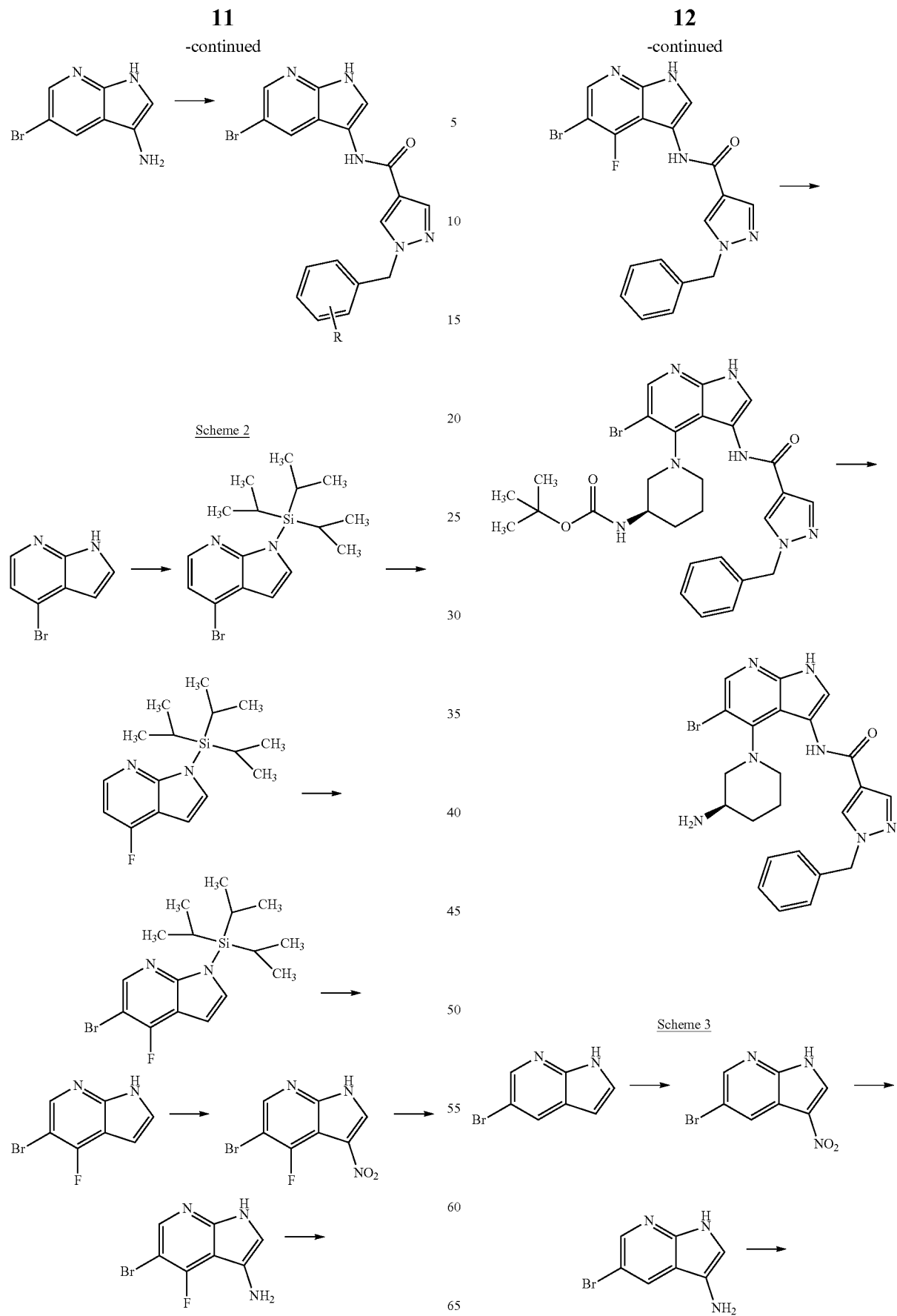

13
-continued
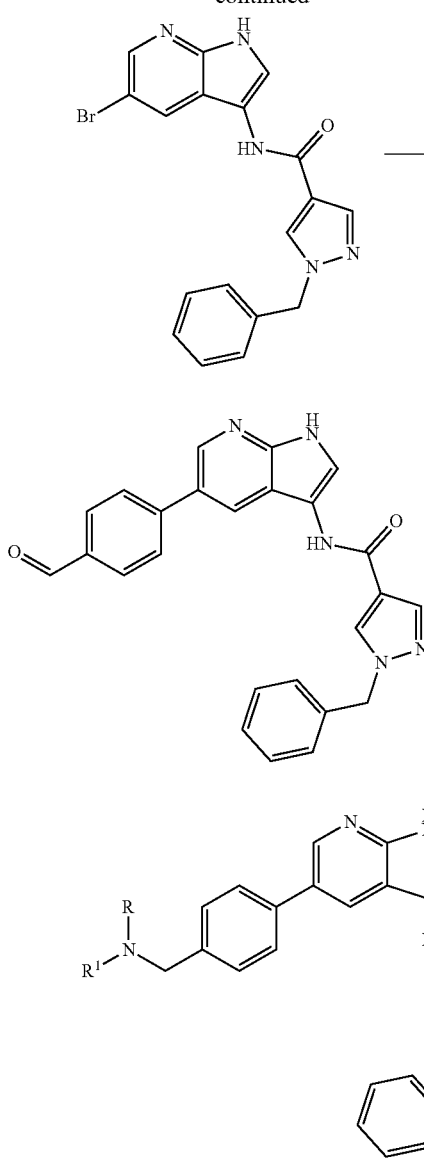
Scheme 4
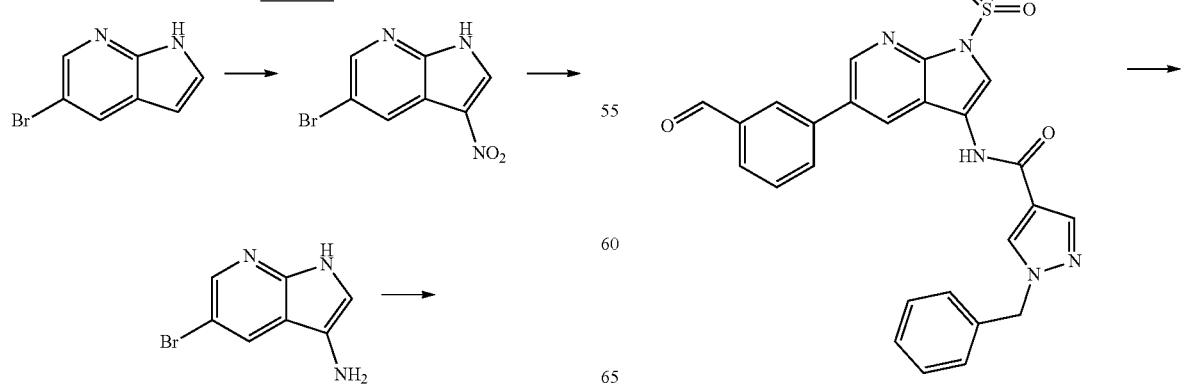
14
-continued
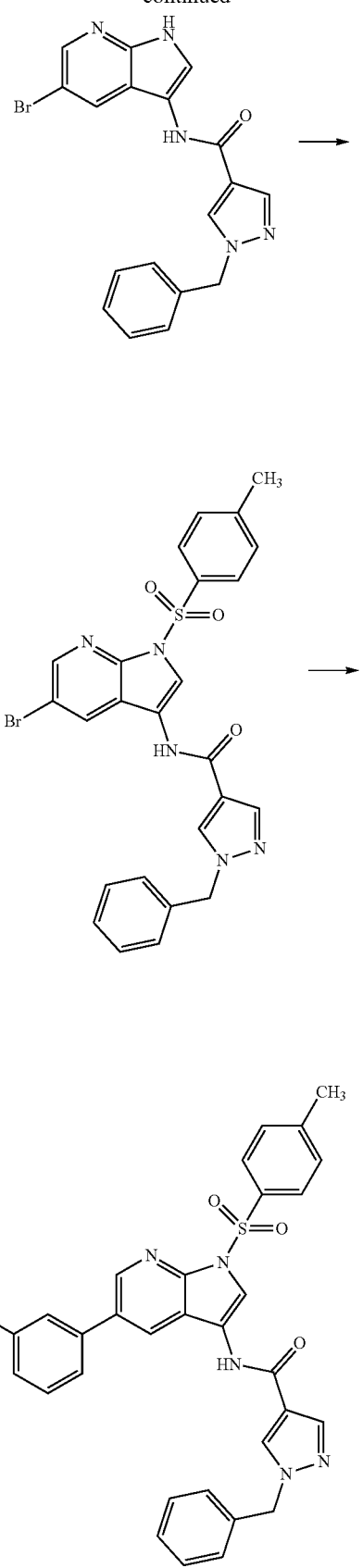

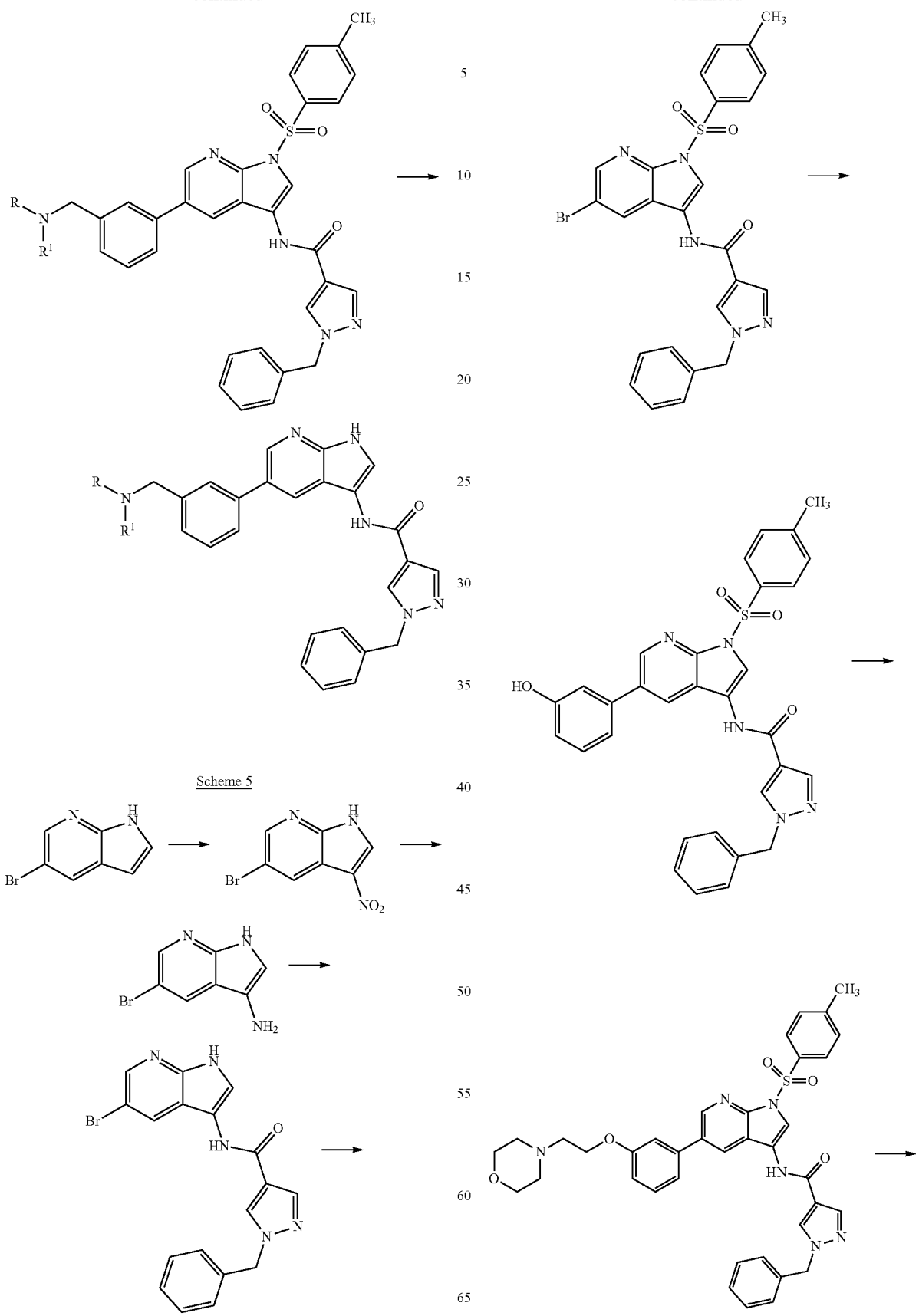

17
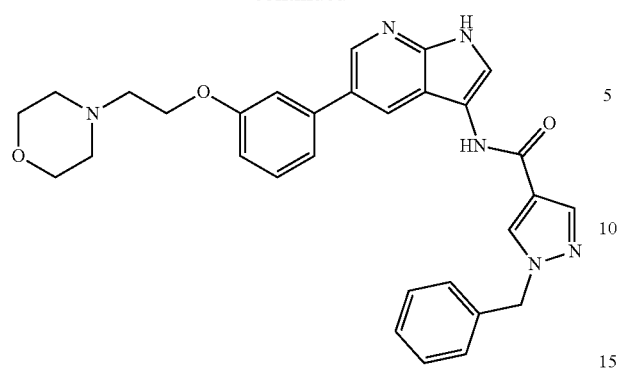
18
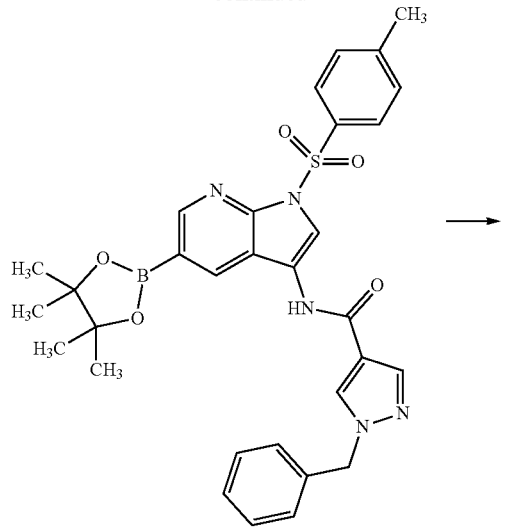
Scheme 6
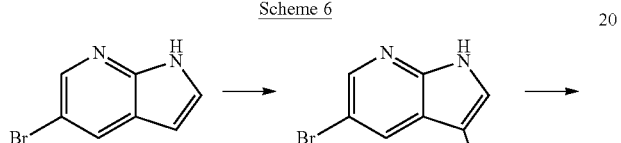
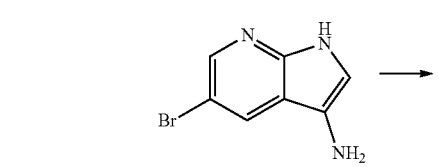
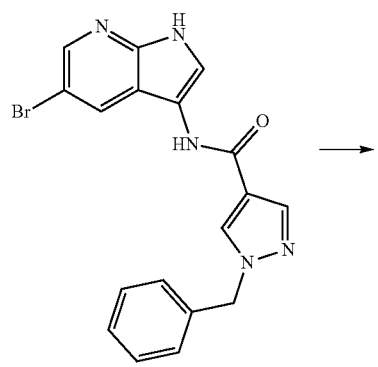
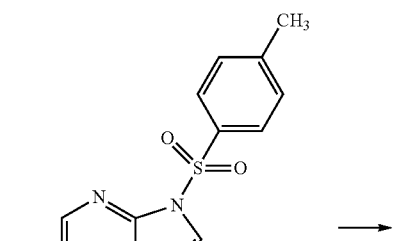
Scheme 7
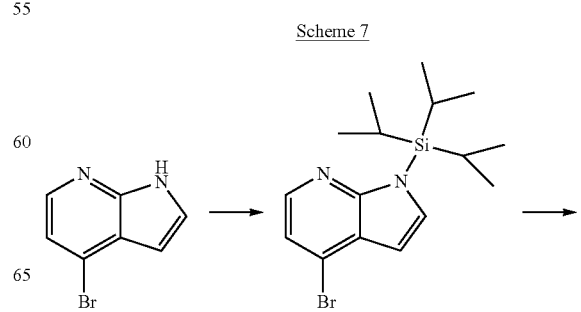

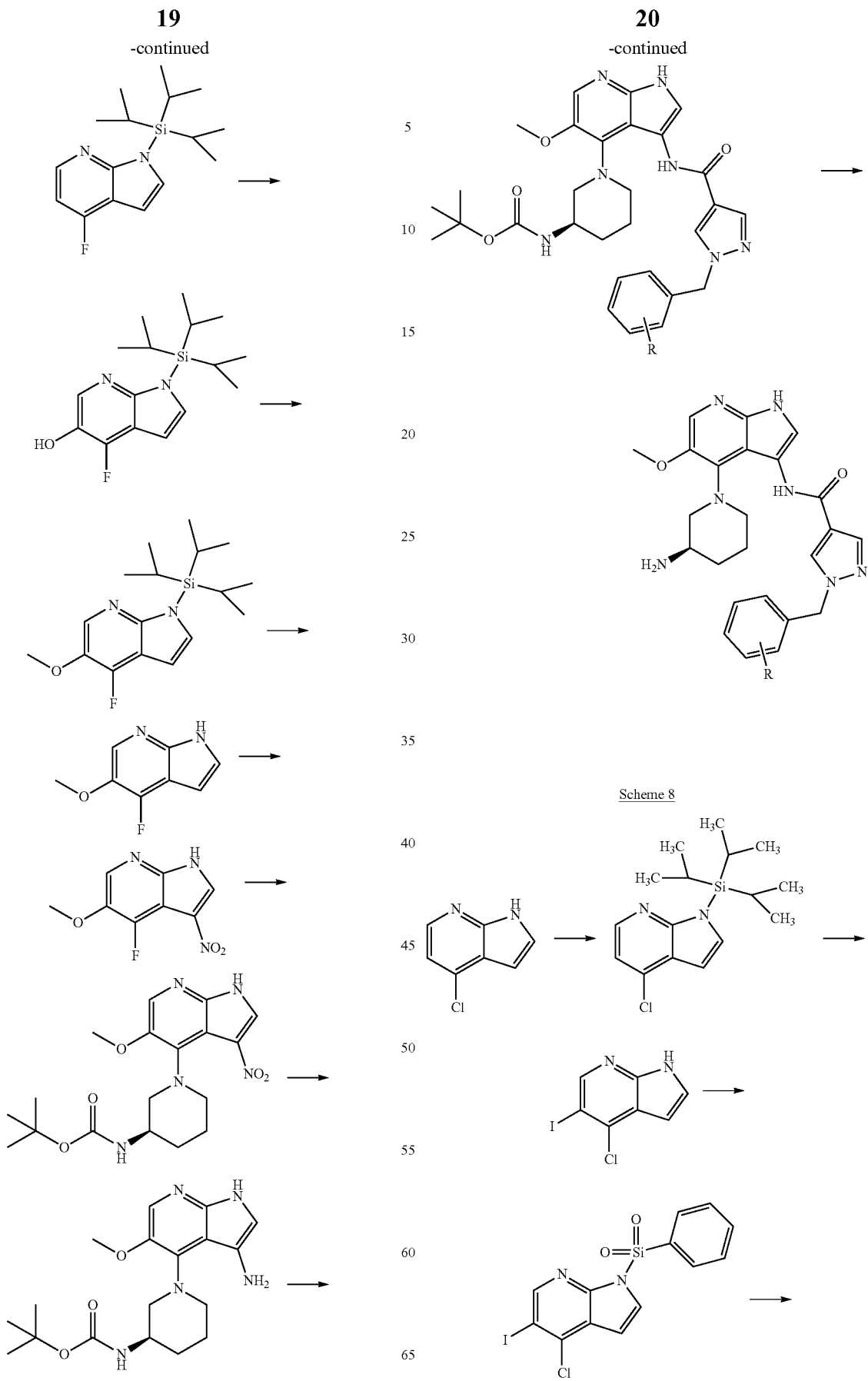

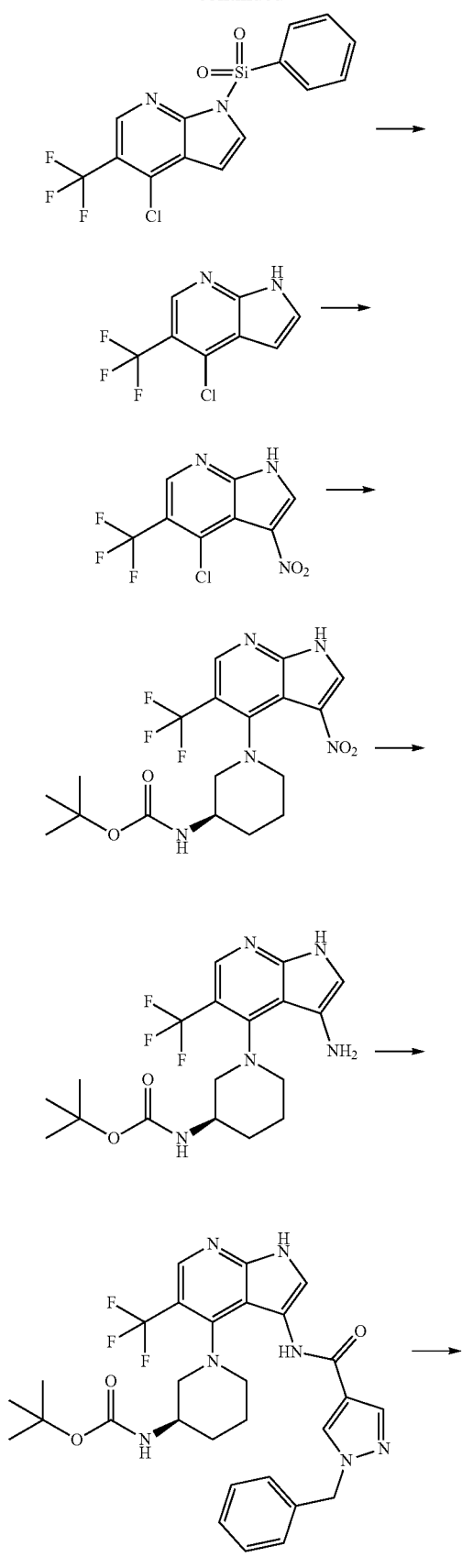
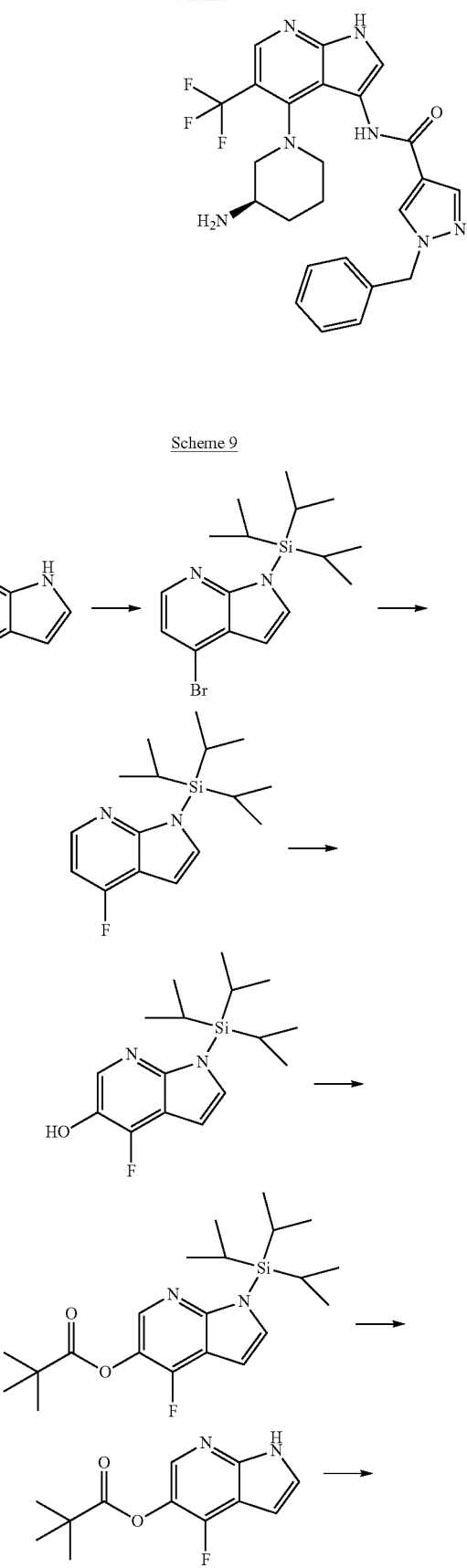
Scheme 9

-continued

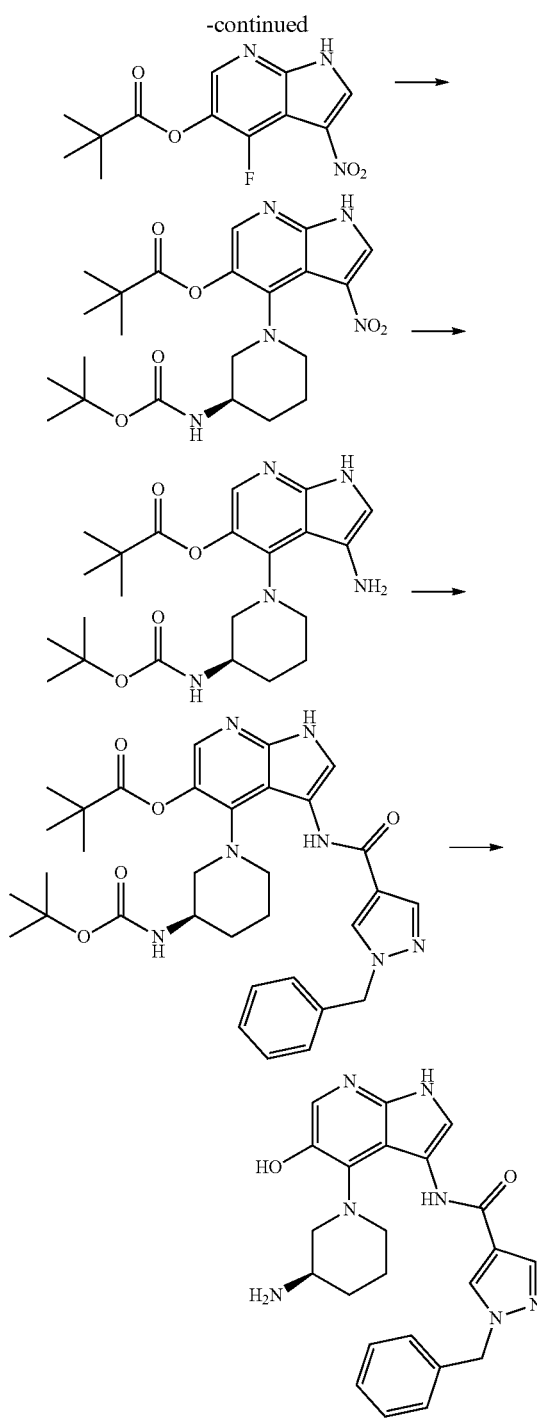

EXAMPLES

The following examples illustrate the preparation of specific compounds of the invention and are not intended to be limiting of the full scope of the invention. Persons skilled in the art should recognize that the chemical syntheses described here may be adapted to prepare other compounds of the invention. Indeed, alternative methods for preparing compounds of this invention are deemed to be within the scope of this invention.

Example 1: 1-Benzyl-1H-pyrazole-4-carboxylic acid (5-bromo-1H-pyrrolo[2,3-b]pyridin-3-yl)-amide

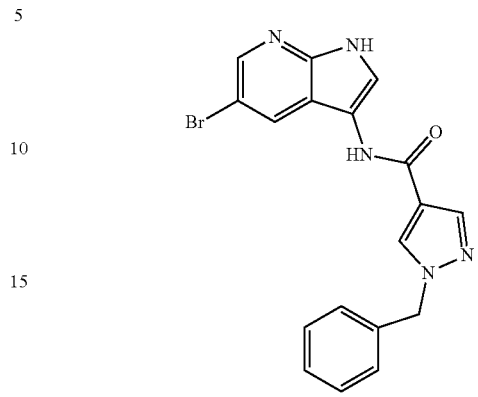

The title compound was prepared according to the route outlined in Scheme 1.

Step 1: Preparation of 5-Bromo-3-nitro-1H-pyrrolo[2,3-b]pyridine

5-Bromo-1H-pyrrolo[2,3-b]pyridine (470 mg, 2.39 mmol) was added in portions to a stirring solution of fuming nitric acid (2.5 mL) at 0° C. After addition the reaction was stirred at 0° C. for 30 minutes and then carefully added to a mixture of ice/$H_2O$ (25 mL) and stirred for 30 minutes. The solids were separated via filtration and the filter cake washed with copious amounts of $H_2O$ and then iso-hexane prior to drying in vacuo to afford the desired title compound, 484 mg, 84%.

Step 2: Preparation of 5-Bromo-1H-pyrrolo[2,3-b]pyridin-3-ylamine

5-Bromo-3-nitro-1H-pyrrolo[2,3-b]pyridine was stirred in glacial acetic acid (6 mL) at 85° C. and to this, was added a solution of tin(II)chloride dihydrate (936 mg, 4.15 mmol) in conc HCl (1 mL), drop wise. After addition the reaction was heated at 85° C. for a further 2 hours and then allowed to cool to room temperature. The reaction mixture was poured onto a mixture of rapidly stirring ice/$H_2O$ (30 mL) and the pH was adjusted to 9 by the careful addition of a 50% aqueous solution of sodium hydroxide. This aqueous mixture was extracted with DCM (3×25 mL) and the combined extracts were washed with $H_2O$, saturated aqueous sodium chloride, dried ($MgSO_4$) and concentrated in vacuo to yield the desired compound, 115 mg, 66%.

Step 3: Preparation of Title compound: 1-Benzyl-1H-pyrazole-4-carboxylic acid (5-bromo-1H-pyrrolo[2,3-b]pyridin-3-yl)-amide 5-Bromo-1H-pyrrolo[2,3-b]pyridin-3-ylamine (60 mg, 0.28 mmol), 1-benzyl-1H-pyrazole-4-carboxylic acid (62 mg, 0.31 mmol) and triethylamine (57 mg, 80 uL, 0.56 mmol) were stirred in dimethyl formamide (1 mL). O-(7-azabenzotriazol-1-yl)-N,N,N',N'-tetramethyluroniumhexafluorophosphate (HATU) (106 mg, 0.28 mmol) was added and the reaction was stirred at room temperature for 4 hours. The reaction mixture was partitioned between EtOAc and saturated sodium hydrogen sulphate solution and the organics separated and washed with saturated aqueous sodium chloride (×4), dried (MgSO$_4$) and solvent removed in vacuo to afford a brown solid. The residue was purified by flash chromatography on SiO$_2$ eluting first with 50% EtOAc/DCM and then 5% MeOH/DCM. The fractions containing pure product were combined and concentrated in vacuo to afford the title compound as a tan solid, 35 mg, 31%.

LC/MS: RT=2.22 Min (270 nm), m/z=396 [M+H], 394 [M−H]. Total run time 3.75 min (short pos/neg), HP1100.

$^1$H NMR (d$_6$ DMSO): δ5.41 (s, 2H), 7.28-7.41 (m, 5H), 7.84 (d, 1H), 8.08 (s, 1H), 8.28 (d, 1H), 8.45 (s, 1H), 8.48 (d, 1H), 9.88 (s, 1H), 11.69 (br s, 1H)

Example 2: 1-Benzyl-1H-pyrazole-4-carboxylic acid (1H-pyrrolo[2,3-b]pyridin-3-yl)-amide

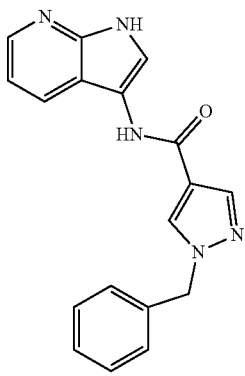 [SMILES: O=C(Nc1c[nH]c2ncccc12)c1cnn(Cc2ccccc2)c1]

The title compound was prepared according to the route outlined in Scheme 1, and using the methodology described for Example 1, Steps 1, 2 and 3, substituting 1H-pyrrolo[2,3-b]pyridine (150 mg, 1.27 mmol) for 5-bromo-1H-pyrrolo[2,3-b]pyridine in Step 1. The title compound was isolated as a cream solid, 60.3 mg, 35.8%.

LC/MS: RT=1.95 Min (270 nm), m/z=318 [M+H], 316 [M−H]. Total run time 3.75 min (short pos/neg), HP1100.

$^1$H NMR (d$_6$ DMSO): δ 5.41 (s, 2H), 7.06 (dd, 1H), 7.28-7.41 (m, 5H), 7.74 (d, 1H), 8.08 (s, 1H), 8.18 (dd, 1H), 8.22 (dd, 1H), 8.44 (s, 1H), 9.87 (s, 1H), 11.41 (br d, 1H)

Example 3: 1-Benzyl-1H-pyrazole-4-carboxylic acid (4-bromo-1H-pyrrolo[2,3-b]pyridin-3-yl)-amide

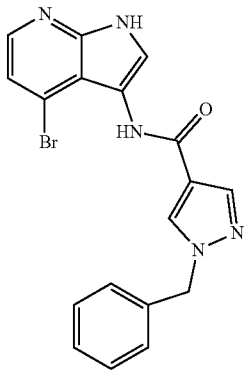 [SMILES: O=C(Nc1c[nH]c2nccc(Br)c12)c1cnn(Cc2ccccc2)c1]

The title compound was prepared by a similar route to that shown in Scheme 1.

Step 1: Preparation of 4-Bromo-3-nitro-1H-pyrrolo[2,3-b]pyridine c.HNO$_3$ (0.93 mL) was added drop wise to a solution of c.H$_2$SO$_4$ (0.64 mL) at 0° C. 4-Bromo-1H-pyrrolo[2,3-b]pyridine (2 g, 10.15 mmol) in c.H$_2$SO$_4$ (9 mL) was added slowly, keeping the temperature at 0° C. After addition the reaction was stirred for a further hour at 0° C. before pouring carefully onto rapidly stirring ice/H$_2$O (100 mL). The suspension was stirred for 30 mins and then the solids separated via filtration. The filter cake was washed with copious amounts of H$_2$O before drying in vacuo at 40° C., to afford the desired compound, 1.9 g, 77.3%

Step 2: Preparation of 4-Bromo-1H-pyrrolo[2,3-b]pyridin-3-ylamine

4-Bromo-3-nitro-1H-pyrrolo[2,3-b]pyridine (500 mg, 2.07 mmol) was heated in 48% aqueous hydrobromic acid (4 mL) at 70° C. and then tin (II) chloride dihydrate (2.26 g, 10 mmol) was added in portions. After addition the reaction was heated at 70° C. for a further 1 hour and then cooled before carefully adding to stirring ice/H$_2$O (15 mL). This solution was basified to pH12 using sodium hydroxide solution, and the insoluble material separated via filtration. The filtrate was extracted with DCM (3×100 mL) and the combined extracts were washed with H$_2$O and saturated aqueous sodium chloride, dried (MgSO$_4$) and concentrated in vacuo. This afforded the desired compound, 230 mg, 52.5%, which was used without further purification.

Step 3: Preparation of Title compound: 1-Benzyl-1H-pyrazole-4-carboxylic acid (4-bromo-1H-pyrrolo[2,3-b]pyridin-3-yl)-amide The title compound (cream solid, 145 mg, 66.5%) was prepared as described in Example 1, Step 3, substituting 4-Bromo-1H-pyrrolo[2,3-b]pyridin-3-ylamine (117 mg, 0.55 mmol) for 5-Bromo-1H-pyrrolo[2,3-b]pyridin-3-ylamine.

LC/MS: RT=2.12 Min (270 nm), m/z=396 [M+H], 394 [M−H] Total run time 3.75 min (short pos/neg), HP1100.

$^1$H NMR (d$_6$ DMSO): δ 5.39 (s, 2H), 7.28-7.41 (m, 6H), 7.61 (d, 1H), 8.03 (s, 1H), 8.07 (d, 1H), 8.39 (s, 1H), 9.43 (s, 1H), 11.99 (br s, 1H)

Example 4: 1-Benzyl-1H-pyrazole-4-carboxylic acid (5-phenyl-1H-pyrrolo[2,3-b]pyridin-3-yl)-amide

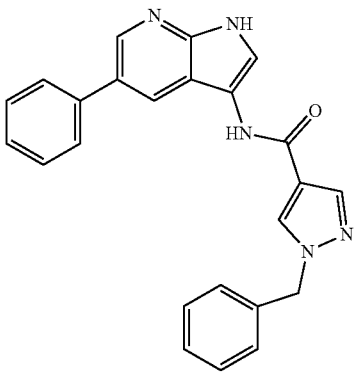 [SMILES: O=C(Nc1c[nH]c2ncc(-c3ccccc3)cc12)c1cnn(Cc2ccccc2)c1]

The title compound was prepared from Example 1.

1-Benzyl-1H-pyrazole-4-carboxylic acid (5-bromo-1H-pyrrolo[2,3-b]pyridin-3-yl)-amide (50 mg, 0.13 mmol), phenylboronic acid (16.9 mg, 0.14 mmol), K$_2$CO$_3$ (53.9 mg, 0.39 mmol) and Pd(dppf)Cl$_2$ (9.5 mg, 0.01 mmol) were combined in THF/H$_2$O (1.1 mL:0.12 mL) and thoroughly degassed. The reaction mixture was heated at 120° C. for 1 hour under microwave irradiation and then it was diluted with EtOAc. The organic layer was separated and the aqueous extracted with another portion of EtOAc. The combined organics were washed with H$_2$O, saturated aqueous sodium chloride, dried (MgSO$_4$) and solvent removed in vacuo to afford a brown gum. This crude material was purified by automated column chromatography, eluting with DCM to 5% MeOH/DCM. Fractions found to contain pure material were combined and solvent removed in vacuo to afford the desired product as a pale brown solid, 27 mg, 54%.

LC/MS: RT=1.23 Min (270 nm), m/z=394 [M+H]. Total run time 1.9 min (super short pos), HP1200

$^1$H NMR (d$_6$ DMSO): δ 5.41 (s, 2H), 7.28-7.41 (m, 6H), 7.5 (m, 2H), 7.71 (dd, 2H), 7.83 (d, 1H), 8.10 (s, 1H), 8.47 (s, 1H), 8.51 (d, 1H), 854 (d, 1H), 9.92 (s, 1H), 11.51 (br d, 1H).

Example 5: 1-Benzyl-1H-pyrazole-4-carboxylic acid (5-piperidin-1-yl-1H-pyrrolo[2,3-b]pyridin-3-yl)-amide

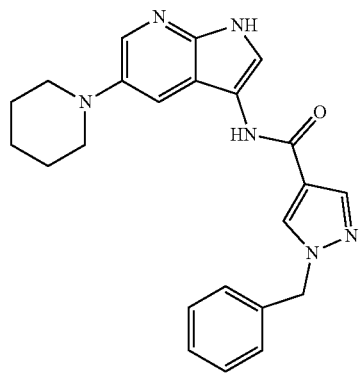 [SMILES: O=C(Nc1c[nH]c2ncc(N3CCCCC3)cc12)c1cnn(Cc2ccccc2)c1]

The title compound was prepared from Example 1.

1-Benzyl-1H-pyrazole-4-carboxylic acid (5-bromo-1H-pyrrolo[2,3-b]pyridin-3-yl)-amide (75 mg, 0.19 mmol), piperidine (0.03 mL, 0.28 mmol), 2-dicyclohexylphosphino-2',6'-diisopropoxybiphenyl (8.83 mg, 0.02 mmol), chloro-(2-dicyclohexylphosphino-2',6'-diisopropoxy-1,1'-biphenyl)[2-(2-aminoethyl)phenyl]palladium(III)-methyl-t-butyl ether adduct (15.5 mg, 0.02 mmol) were added to a 0.5-2.0 mL microwave vial. The vial was sealed, evacuated and back-filled with nitrogen. Lithium bis(trimethylsilyl)amide solution, 1.0M in THF. (0.45 mL, 0.45 mmol) was added and reaction mixture was heated at 65° C. for 18 hours. The reaction was allowed to cool and the mixture was quenched with 1N HCl, diluted with DCM, washed with H$_2$O, dried (phase separator) and solvent removed in vacuo to afford a brown solid. This crude material was purified by automated column chromatography, eluting with DCM-10% MeOH/DCM (gradient). Fractions found to contain product were combined and solvent removed in vacuo to afford a brown solid, 11 mg, 14%.

LC/MS: RT=1.02 Min (270 nm), m/z=401 [M+H]. Total run time 1.9 min (super short pos), HP1200.

$^1$H NMR (d$_6$ DMSO): δ 1.49-1.51 (m, 2H), 1.65-1.73 (m, 4H), 3.01-3.07 (m, 4H), 5.41 (s, 2H), 7.28-7.41 (m, 5H), 7.69 (s, 1H), 7.76 (s, 1H), 8.05 (d, 1H), 8.07 (s, 1H), 8.44 (s, 1H), 9.75 (s, 1H), 11.11 (br d, 1H)

Example 6: N-{4-[(3R)-3-aminopiperidin-1-yl]-5-bromo-1H-pyrrolo[2,3-b]pyridin-3-yl}-1-benzyl-1H-pyrazole-4-carboxamide

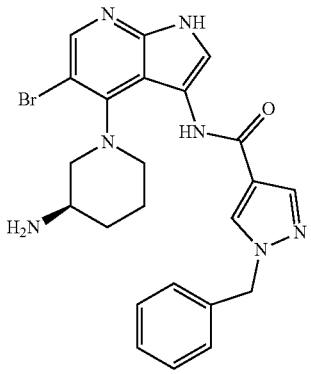 [SMILES: N[C@@H]1CCCN(c2c(Br)cnc3[nH]cc(NC(=O)c4cnn(Cc5ccccc5)c4)c23)C1]

The title compound was prepared according to the route outlined in Scheme 2.

Step 1: Preparation of 4-bromo-1-[tris(propan-2-yl)silyl]-1H-pyrrolo[2,3-b]pyridine Sodium hydride, 60% dispersion in mineral oil (0.49 g, 12.18 mmol) was added in portions to 4-bromo-1H-pyrrolopyridine (2 g, 10.15 mmol) in THF (45 mL) at 0° C. and stirred for 15 minutes. Triisopropylsilyl chloride (2.31 g, 2.57 mL, 12 mmol) was then added to the reaction mixture drop wise at 0° C. After addition the cooling was removed and the reaction mixture allowed to attain RT, where it was stirred for a further 1 hour. The suspension was then cooled to about 0-5° C. and quenched with saturated aqueous ammonium chloride (30 mL). The aqueous phase was extracted with EtOAc (3×30 mL) and the combined organic phases were washed with saturated aqueous sodium chloride, dried (MgSO$_4$) and solvent removed in vacuo to afford a yellow oil. The crude material was purified by flash chromatography, eluting with iso-hexane. Fractions found to contain pure product were combined and solvent removed in vacuo to afford the desired compound as an oil, 3.5 g, 97.6%.

Step 2: Preparation of 4-fluoro-1-[tris(propan-2-yl)silyl]-1H-pyrrolo[2,3-b]pyridine n-Butyllithium solution, 2.5M in hexanes (2.52 mL, 11.3 mmol) was added drop wise to a solution of 4-bromo-1-[tris(propan-2-yl)silyl]-1H-pyrrolo[2,3-b]pyridine (2.0 g, 5.66 mmol) in Et$_2$O (60 mL) at −78° C. under a nitrogen atmosphere, and the mixture stirred for 30 minutes at −78° C. and for 45 mins at −5° C. to give a pale yellow solution. The resulting solution was cooled to −78° C., and a solution of N-fluorobis(phenylsulphonyl)amine (2.05 g, 6.51 mmol) in THF (10 mL) was added drop wise. The mixture stirred for a further 3 hours at −78° C., and then quenched by the addition of saturated aqueous ammonium chloride solution. The organic layer was separated and the aqueous layer was extracted with Et$_2$O (2×50 mL) and the combined extracts washed with saturated aqueous sodium chloride solution. The solution was dried over anhydrous MgSO$_4$ and concentrated to a yellow gum. The crude material was purified by flash chromatography, eluting with iso-hexane. Fractions found to contain pure product were combined and solvent removed in vacuo to afford the desired compound as a colourless oil, 1.3 g, 78.5%.

Step 3: Preparation of 5-Bromo-4-fluoro-1-[tris(propan-2-yl)silyl]-1H-pyrrolo[2,3-b]pyridine 4-fluoro-1-[tris(propan-2-yl)silyl]-1H-pyrrolo[2,3-b]pyridine (833.0 mg, 2.85 mmol) in THF (34 mL) at −78° C. was treated drop wise with sec-butyllithium solution, 1.4M in cyclohexane (4.48 mL, 6.27 mmol). The reaction was stirred at −78° C. for 1 hour. A solution of carbon tetrabromide (2.36 g, 7.12 mmol) in THF (6.3 mL) was added drop wise and the reaction was stirred at −78° C. for a further 1 hour. The reaction was quenched by the addition of saturated aqueous ammonium chloride. The mixture was extracted with iso-hexane (×2) and the combined extracts washed with saturated aqueous sodium chloride. The solution was dried over anhydrous MgSO4 and concentrated to a brown oil. The crude material was purified by automated column chromatography, eluting with iso-hexane. Fractions found to contain pure product were combined and solvent removed in vacuo to afford the desired compound as a yellow gum that solidified on standing, 0.97 g, 91.7%.

Step 4: Preparation of 5-Bromo-4-fluoro-1H-pyrrolo[2,3-b]pyridine

Tetrabutylammonium fluoride solution, 1.0M in THF (2.61 mL, 2.61 mmol) was added to a solution of 5-bromo-4-fluoro-1-[tris(propan-2-yl)silyl]-1H-pyrrolo[2,3-b]pyridine (970 mg, 2.61 mmol) in THF (16.5 mL) at RT. The reaction mixture was stirred at RT for 20 minutes and then partitioned between H$_2$O and Et$_2$O. The organic layer was separated and the aqueous was extracted with more Et$_2$O (2×25 mL). The combined organic phases were washed with saturated aqueous sodium chloride, dried (MgSO$_4$) and concentrated in vacuo to afford a brown gum.

The crude material was purified by automated chromatography, eluting with iso-hexane to 40% EtOAc/iso-hexane (gradient). Fractions found to contain pure product were combined and solvent removed in vacuo to afford the desired compound as an off white solid, 0.323 g, 57.5%.

Step 5: Preparation of 5-Bromo-4-fluoro-3-nitro-1H-pyrrolo[2,3-b]pyridine

5-Bromo-4-fluoro-1H-pyrrolo[2,3-b]pyridine (0.323 g, 1.50 mmol) was added in portions to fuming nitric acid (1.6 mL) at 0° C. After addition the reaction mixture was stirred at 0° C. for 30 minutes and then added carefully to rapidly stirring ice/H$_2$O (25 mL). The suspension was stirred for a further 30 minutes and then the solids were collected via filtration and the filter cake washed with copious amounts of H$_2$O and then iso-hexane, prior to drying in vacuo at 60° C. This yielded the desired compound as an off white solid, 0.335 g, 85.8%.

Step 6: Preparation of 5-Bromo-4-fluoro-1H-pyrrolo[2,3-b]pyridin-3-ylamine

Tin (II) chloride dihydrate (2.62 g, 13.8 mmol) was added in portions to 5-Bromo-4-fluoro-3-nitro-1H-pyrrolo[2,3-b]pyridine (0.717 g, 2.76 mmol) in 6N HCl (21 mL) at 0° C. and then the cooling was removed and the reaction stirred at RT for 1 hour. The reaction mixture was cooled and poured onto a mixture of ice/H$_2$O (50 mL) and basified to pH 8 by the careful addition of 50% sodium hydroxide solution. This was extracted with DCM/isopropyl alcohol (3:1; v:v) (3×100 mL) and the combined extracts were washed with saturated aqueous sodium chloride, dried (MgSO$_4$) and concentrated in vacuo to afford a brown solid. This yielded the desired compound as a brown solid, 0.613 g, 96.5%.

Step 7: Preparation of 1-Benzyl-1H-pyrazole-4-carboxylic acid (5-bromo-4-fluoro-1H-pyrrolo[2,3-b]pyridin-3-yl)-amide This was prepared using the methodology described for Example 1, Step 3, 0.85 g, 77.0%.

Step 8: Preparation of Title compound: 1-Benzyl-1H-pyrazole-4-carboxylic acid [4-((R)-3-amino-piperidin-1-yl)-5-bromo-1H-pyrrolo[2,3-b]pyridin-3-yl]-amide 1-Benzyl-1H-pyrazole-4-carboxylic acid (5-bromo-4-fluoro-1H-pyrrolo[2,3-b]pyridin-3-yl)-amide (40 mg, 0.10 mmol), (R)-piperidin-3-yl-carbamic acid tert-butyl ester (97 mg, 0.48 mmol) and n-butanol (2 mL) were combined in a 2-5 mL microwave vial. The contents were heated at 160° C. for 8 hours under microwave irradiation and then the reaction mixture was concentrated in vacuo. The residue was taken up in DCM (3 mL) then TFA (3 mL) was added at RT and stirring continued for 3 hours. The solvent was removed in vacuo and the residue taken up in EtOAc (20 mL), that was washed with saturated aqueous sodium hydrogen carbonate (3×20 mL) and saturated aqueous sodium chloride-saturated aqueous sodium chloride (50 mL). The organics were dried (MgSO$_4$) and concentrated in vacuo to afford a dark yellow gum. This crude material was purified by automated chromatography, eluting with DCM to 10% MeOH/DCM (gradient). Fractions found to contain pure product were combined and concentrated in vacuo to afford the title compound as a pale yellow solid, 10.2 mg, 21.4%.

LC/MS: RT=1.77 Min (270 nm), m/z=494.4 [M+H]. Total run time 3.75 min (short pos/neg), HP1100.

$^1$H NMR (d$_6$ DMSO): δ 1.13-1.20 (m, 1H), 1.44-1.53 (m, 1H), 1.62-1.77 (m, 2H), 2.88-2.98 (m, 2H), 3.10-3.19 (m, 2H), 5.42 (s, 2H), 7.26-7.40 (m, 5H), 7.71 (s, 1H), 8.04 (s, 1H), 8.19 (s, 1H), 8.52 (s, 1H), 9.77 (br s, 1H), 11.71 (s, 1H) 3 protons not seen Example 7: 1-Benzyl-1H-pyrazole-4-carboxylic acid [4-((R)-3-amino-pyrrolidin-1-yl-5-bromo-1H-pyrrolo[2,3-b]pyridin-3-yl]-amide

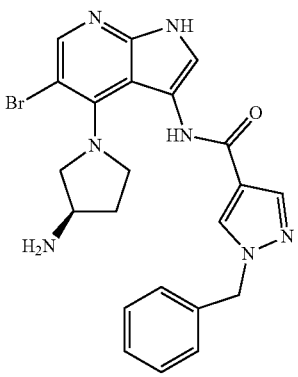 [SMILES: N[C@@H]1CCN(c2c(Br)cnc3[nH]cc(NC(=O)c4cnn(Cc5ccccc5)c4)c23)C1]

The title compound (cream solid, 50.6 mg, 54.5%) was prepared as described in Example 6, substituting (R)-pyrrolidin-3-yl-carbamic acid tert-butyl ester (180 mg, 0.97 mmol) for (R)-piperidin-3-yl-carbamic acid tert-butyl ester in Step 8.

LC/MS: RT=1.73 Min (254 nm), m/z=480.4 [M+H]. Total run time 3.75 min (short pos/neg), HP1100.

$^1$H NMR (d$_6$ DMSO): δ 1.68-1.75 (m, 1H), 1.78-1.87 (br s, 2H), 2.12-2.21 (m, 1H), 3.00-3.03 (m, 1H), 3.39-3.45 (m, 1H), 3.52-3.58 (m, 2H), 3.66-3.70 (m, 1H), 5.39 (s, 2H), 7.28-7.40 (m, 5H), 7.78 (s, 1H), 8.10 (s, 1H), 8.25 (s, 1H), 8.67 (s, 1H), 9.81 (br s, 1H), 11.63 (s, 1H)

Example 8: 1-Benzyl-1H-pyrazole-4-carboxylic acid [5-bromo-4-((R)-3-methylamino-piperidin-1-yl)-1H-pyrrolo[2,3-b]pyridin-3-yl]-amide

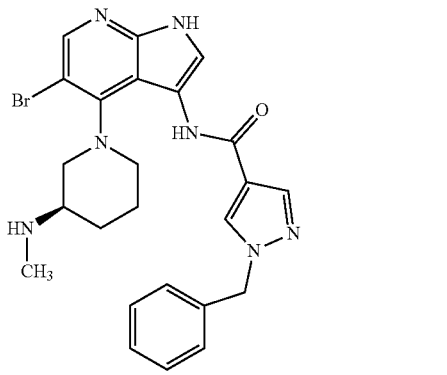 [SMILES: CN[C@@H]1CCCN(c2c(Br)cnc3[nH]cc(NC(=O)c4cnn(Cc5ccccc5)c4)c23)C1]

The title compound (cream solid, 63.4 mg, 51.7%) was prepared as described in Example 6, substituting carbamic acid, N-methyl-N-(3R)-3-piperidinyl-, 1,1-dimethylethyl ester (259 mg, 1.21 mmol) for (R)-piperidin-3-yl-carbamic acid tert-butyl ester in Step 8.

LC/MS: RT=1.78 Min (270 nm), m/z=510.4 [M+H]. Total run time 3.75 min (short pos/neg), HP1100.

$^1$H NMR (d$_6$ DMSO): δ 1.28-1.35 (m, 1H), 1.47-1.52 (m, 1H), 1.62-1.68 (m, 1H), 1.72-1.79 (m, 1H), 2.10 (s, 3H), 2.56-2.61 (m, 1H), 2.95-2.99 (m, 1H), 3.09-3.18 (m, 1H), 3.21-3.27 (m, 1H), 3.45-3.52 (m, 1H), 5.42 (s, 2H), 7.26-7.39 (m, 5H), 7.79 (s, 1H), 8.07 (s, 1H), 8.19 (s, 1H), 8.47 (s, 1H), 9.82 (br s, 1H), 11.70 (s, 1H) 1 proton not seen Example 9: 1-Benzyl-1H-pyrazole-4-carboxylic acid [5-bromo-4-((R)-3-ethylamino-piperidin-1-yl)-1H-pyrrolo[2,3-b]pyridin-3-yl]-amide

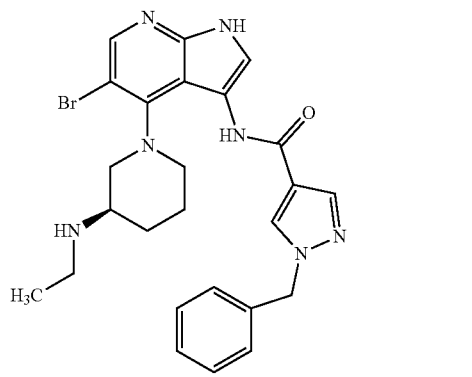 [SMILES: CCN[C@@H]1CCCN(c2c(Br)cnc3[nH]cc(NC(=O)c4cnn(Cc5ccccc5)c4)c23)C1]

The title compound (cream solid, 34.8 mg, 39.4%) was prepared as described in Example 6, substituting carbamic acid, N-ethyl-N-(3R)-3-piperidinyl-, 1,1-dimethylethyl ester (116 mg, 0.51 mmol) for (R)-piperidin-3-yl-carbamic acid tert-butyl ester in Step 8.

LC/MS: RT=1.81 Min (270 nm), m/z=524.5 [M+H]. Total run time 3.75 min (short pos/neg), HP1100.

$^1$H NMR (d$_6$ DMSO): δ 0.87 (t, 3H), 1.23-1.28 (m, 1H), 1.50-1.56 (m, 1H), 1.71-1.73 (m, 2H), 2.45 (q, 2H), 2.72-2.78 (m, 1H), 2.99-3.05 (m, 1H), 3.14-3.21 (m, 2H), 5.42 (s, 2H), 7.26-7.39 (m, 5H), 7.71 (s, 1H), 8.06 (s, 1H), 8.20 (s, 1H), 8.45 (s, 1H), 9.70 (br s, 1H), 11.73 (s, 1H) 2 protons not seen Example 10: 1-Benzyl-1H-pyrazole-4-carboxylic acid [5-bromo-4-((R)-3-hydroxy-pyrrolidin-1-yl)-1H-pyrrolo[2,3-b]pyridin-3-yl]-amide

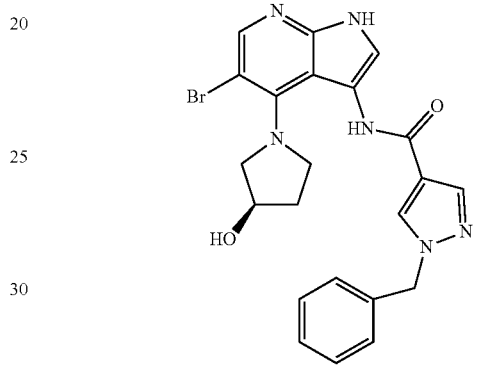

The title compound (pale orange solid, 47 mg, 51.0%) was prepared as described in Example 6, substituting (R)-pyrrolidin-3-ol (84 mg, 0.97 mmol) for (R)-piperidin-3-yl-carbamic acid tert-butyl ester in Step 8.

LC/MS: RT=2.30 Min (270 nm), m/z=483.4 [M+H]. Total run time 3.75 min (short pos/neg), HP1100.

$^1$H NMR (d$_6$ DMSO): δ 1.94-1.99 (m, 1H), 2.24-2.33 (m, 1H), 3.14-3.17 (m, 1H), 3.43-3.49 (m, 1H), 3.53-3.60 (m, 1H), 3.64-3.68 (m, 1H), 4.54 (br s, 1H), 5.37 (s, 2H), 5.50 (d, 1H), 7.29-7.39 (m, 5H), 7.85 (s, 1H), 8.14 (s, 1H), 8.27 (s, 1H), 8.60 (s, 1H), 9.72 (br s, 1H), 11.63 (s, 1H)

Example 11: 1-Benzyl-1H-pyrazole-4-carboxylic acid [5-bromo-4-((R)-3-hydroxy-piperidin-1-yl)-1H-pyrrolo[2,3-b]pyridin-3-yl]-amide

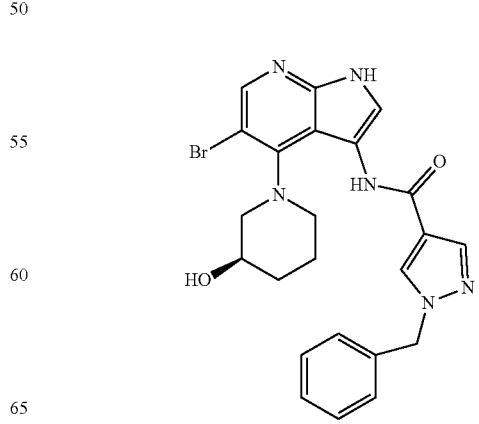

The title compound (pale yellow solid, 3.6 mg, 6.0%) was prepared as described in Example 6, substituting (R)-3-hydroxypiperidine hydrochloride (83 mg, 0.6 mmol) for (R)-piperidin-3-yl-carbamic acid tert-butyl ester and using potassium carbonate (83 mg, 0.6 mmol) as base in Step 8.

LC/MS: RT=2.35 Min (270 nm), m/z=495.4 [M+H]. Total run time 3.75 min (short pos/neg), HP1100.

$^1$H NMR (d$_6$ DMSO): δ 1.48-1.54 (m, 2H), 1.63-1.68 (m, 1H), 1.78-1.87 (m, 1H), 2.97-3.07 (m, 2H), 3.54-3.63 (m, 1H), 3.84-3.90 (m, 1H), 5.33 (br s, 1H), 5.39 (s, 2H), 7.26-7.39 (m, 5H), 7.88 (s, 1H), 8.18 (s, 1H), 8.20 (s, 1H), 8.62 (s, 1H), 9.91 (br s, 1H), 11.69 (s, 1H) 1 proton not seen

Example 12: 1-Benzyl-1H-pyrazole-4-carboxylic acid [5-bromo-4-(3-dimethylamino-piperidin-1-yl)-1H-pyrrolo[2,3-b]pyridin-3-yl]-amide

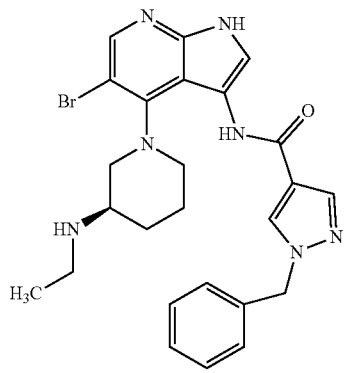 [SMILES: CCN[C@@H]1CCCN(c2c(Br)cnc3[nH]cc(NC(=O)c4cnn(Cc5ccccc5)c4)c23)C1]

The title compound (pale yellow solid, 51.9 mg, 54.9%) was prepared as described in Example 6, substituting dimethyl-piperidin-3-yl-amine (116 mg, 0.91 mmol) for (R)-piperidin-3-yl-carbamic acid tert-butyl ester in Step 8.

LC/MS: RT=1.78 Min (270 nm), m/z=524.5 [M+H]. Total run time 3.75 min (short pos/neg), HP1100.

$^1$H NMR (d$_6$ DMSO): δ 1.31-1.37 (m, 1H), 1.54-1.58 (m, 1H), 1.63-1.75 (m, 2H), 1.99 (s, 6H), 2.21-2.25 (m, 1H), 3.10-3.19 (m, 3H), 4.26-4.46 (m, 1H), 541 (s, 2H), 7.25-7.27 (m, 2H), 7.30-7.39 (m, 3H), 7.70 (s, 1H), 8.07 (s, 1H), 8.20 (s, 1H), 8.42 (s, 1H), 9.61 (br s, 1H), 11.73 (s, 1H)

Example 13: 1-Benzyl-1H-pyrazole-4-carboxylic acid {5-bromo-4-((R)-3-(cyclopentylmethyl-amino)-piperidin-1-yl-1H-pyrrolo[2,3-b]pyridin-3-yl}-amide

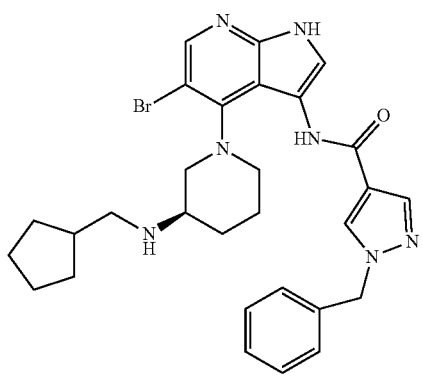 [SMILES: O=C(Nc1c[nH]c2ncc(Br)c(N3CCC[C@@H](NCC4CCCC4)C3)c12)c1cnn(Cc2ccccc2)c1]

The title compound was prepared from Example 6

1-Benzyl-1H-pyrazole-4-carboxylic acid (5-bromo-1H-pyrrolo[2,3-b]pyridin-3-yl)-amide (40.0 mg, 0.08 mmol), acetic acid (0.01 mL, 0.17 mmol) and cyclopentanecarbaldehyde (10.8 mg, 0.11 mmol) were stirred in MeOH (0.5 mL). Reaction mixture was stirred at RT for 10 minutes before addition of NaBH(OAc)$_3$ (42.4 mg, 0.2 mmol) and reaction mixture was left to stir at RT 18 hours. The reaction mixture was basified with sodium bicarbonate solution and extracted with EtOAc (3×30 mL). The organic phases were combined, washed with saturated aqueous sodium chloride, dried (MgSO$_4$) and concentrated in vacuo. The residue was purified by automated column chromatography, eluting with DCM to 5% MeOH/DCM (gradient). Fractions found to contain pure product were combined and concentrated in vacuo to afford the title compound as a yellow solid, 5.6 mg, 12.1%.

LC/MS: RT=2.00 Min (230 nm), m/z=576.6 [M+H]. Total run time 3.75 min (short pos/neg), HP1100.

$^1$H NMR (d$_6$ DMSO): δ 0.94-1.80 (m, 14H), 2.24-2.32 (m, 2H), 2.59-2.66 (m, 1H), 2.93-3.68 (m, 3H), 5.41 (s, 2H), 7.25-7.26 (m, 2H), 7.30-7.39 (m, 3H), 7.68 (d, 1H), 8.03 (s, 1H), 8.19 (s, 1H), 8.42 (s, 1H), 9.66 (br s, 1H), 11.72 (d, 1H)

Example 14: 1-Benzyl-1H-pyrazole-4-carboxylic acid [5-bromo-4-((R)-3-isobutylamino-piperidin-1-yl)-1H-pyrrolo[2,3-b]pyridin-3-yl]-amide

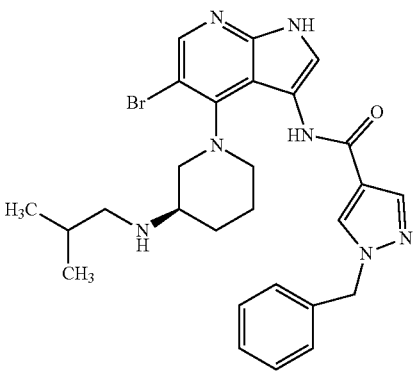 [SMILES: CC(C)CN[C@@H]1CCCN(c2c(Br)cnc3[nH]cc(NC(=O)c4cnn(Cc5ccccc5)c4)c23)C1]

The title compound (cream solid, 38.1 mg, 68.4%) was prepared as described in Example 13, substituting isobutyraldeyhyde (9.9 mg, 0.14 mmol) for cyclopentanecarbaldehyde.

LC/MS: RT=1.91 Min (254 nm), m/z=552.5 [M+H]. Total run time 3.75 min (short pos/neg), HP1100.

$^1$H NMR (d$_6$ DMSO): δ 0.74 (d, 6H), 1.14-1.20 (m, 1H), 1.40-1.50 (m, 1H), 1.52-1.58 (m, 1H), 1.69-1.71 (m, 2H), 2.13-2.22 (m, 2H), 2.58-2.62 (m, 1H), 2.95-3.00 (m, 1H), 3.10-3.15 (m, 1H), 3.21-3.27 (m, 1H), 5.42 (s, 2H), 7.25-7.27 (m, 2H), 7.30-7.39 (m, 3H), 7.66 (d, 1H), 8.02 (s, 1H), 8.19 (s, 1H), 8.41 (s, 1H), 9.62 (br s, 1H), 11.73 (br s, 1H) 2 protons not seen

Example 15: 1-Benzyl-1H-pyrazole-4-carboxylic acid {5-bromo-4-[(R)-3-(2,2-dimethyl-propylamino)-piperidin-1-yl]-1H-pyrrolo[2,3-b]pyridin-3-yl}-amide

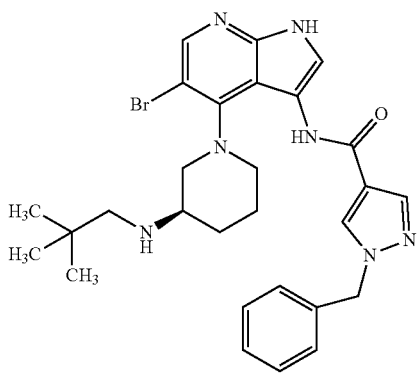 [SMILES: CC(C)(C)CN[C@@H]1CCCN(c2c(Br)cnc3[nH]cc(NC(=O)c4cnn(Cc5ccccc5)c4)c23)C1]

The title compound (cream solid, 38.1 mg, 68.4%) was prepared as described in Example 13, substituting isobutyraldeyhyde (9.9 mg, 0.14 mmol) for cyclopentanecarbaldehyde.

LC/MS: RT=1.96 Min (270 nm), m/z=566.5 [M+H]. Total run time 3.75 min (short pos/neg), HP1100.

$^1$H NMR (d$_6$ DMSO): δ 0.75 (s, 9H), 1.08-1.13 (m, 2H), 1.53-1.58 (m, 1H), 1.63-1.74 (m, 2H), 2.10-2.17 (m, 2H), 2.97-3.08 (m, 2H), 5.41 (s, 2H), 7.23-7.26 (m, 2H), 7.30-7.39 (m, 3H), 7.58 (s, 1H), 8.00 (s, 1H), 8.19 (s, 1H), 8.39 (s, 1H), 9.52 (br s, 1H), 11.74 (s, 1H) 3 protons not seen

Example 16: 1-Benzyl-1H-pyrazole-4-carboxylic acid {5-bromo-4-((R)-3-(cyclopropylmethyl-amino)-piperidin-1-yl-1H-pyrrolo[2,3-b]pyridin-3-yl}-amide

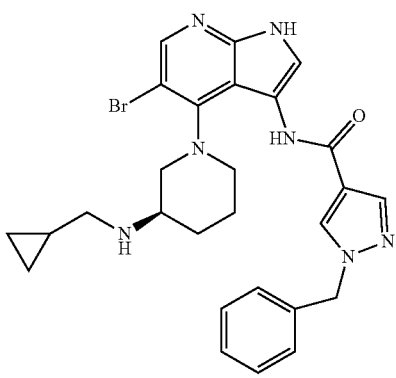 [SMILES: O=C(Nc1c[nH]c2ncc(Br)c(N3CCC[C@@H](NCC4CC4)C3)c12)c1cnn(Cc2ccccc2)c1]

The title compound (cream solid, 18.4 mg, 41.9%) was prepared as described in Example 13, substituting cyclopropylcarboxaldehyde (7.7 mg, 0.14 mmol) for cyclopentanecarbaldehyde.

LC/MS: RT=1.88 Min (254 nm), m/z=550.5 [M+H]. Total run time 3.75 min (short pos/neg), HP1100.

$^1$H NMR (d$_6$ DMSO): δ 0.09-0.02 (m, 2H), 0.23-0.26 (m, 2H), 0.64-0.71 (m, 1H), 1.25-1.30 (m, 1H), 1.51-1.56 (m, 1H), 1.68-1.77 (m, 2H), 2.18-2.29 (m, 2H), 2.71-2.77 (m, 1H), 2.96-3.03 (m, 1H), 3.16-3.28 (m, 2H), 5.42 (s, 2H), 7.25-7.27 (m, 2H), 7.30-7.39 (m, 3H), 7.73 (s, 1H), 8.05 (s, 1H), 8.19 (s, 1H), 8.47 (s, 1H), 9.74 (br s, 1H), 11.71 (s, 1H) 2 protons not seen

Example 17: 1-(4-Fluoro-benzyl-1H-pyrazole-4-carboxylic acid [4-((R)-3-amino-piperidin-1-yl-5-bromo-1H-pyrrolo[2,3-b]pyridin-3-yl]-amide

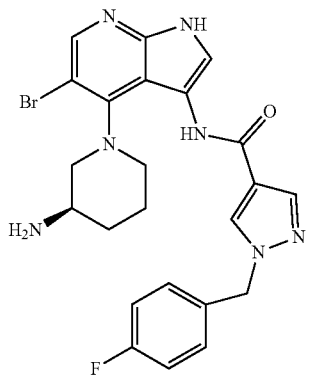 [SMILES: N[C@@H]1CCCN(c2c(Br)cnc3[nH]cc(NC(=O)c4cnn(Cc5ccc(F)cc5)c4)c23)C1]

The title compound was prepared as described in Example 6, substituting 1-(4-fluoro-benzyl)-1H-pyrazole-4-carboxylic acid (157 mg, 0.715 mmol) for 1-benzyl-1H-pyrazole-4-carboxylic acid, in Step 7.

Preparation of
1-(4-fluoro-benzyl)-1H-pyrazole-4-carboxylic acid

Ethyl 4-pyrazolecarboxylate (1.5 g, 10.7 mmol) and K$_2$CO$_3$ (4.44 g, 32.1 mmol) were stirred in acetone (45 mL). To this was added 4-fluorobenzyl bromide (1.38 mL, 11.24 mmol) and the reaction mixture was heated at 50° C. for 18 hours. The reaction was cooled to RT and the solids separated via filtration. The filter cake was washed through with EtOAc and the filtrate concentrated in vacuo. The residue was taken up in MeOH (36 mL) and a solution of KOH (1.20 g, 21.4 mmol) in water (7.2 mL) was added. The reaction was refluxed for 2 hours, cooled and the solvent removed in vacuo. The residue was diluted with a little H$_2$O, cooled to 5° C., and acidified by the careful addition of 1M HCl solution to precipitate the product. After stirring for 10 minutes the solids were collected via filtration, washed well with water, iso-hexane and dried in vacuo at 40° C. for 18 hours to afford 1-(4-fluoro-benzyl)-1H-pyrazole-4-carboxylic acid as a white solid, 2.35 g, 99.6%.

The title compound was isolated as a pale yellow solid, 20.5 mg, 17.3%.

LC/MS: RT=1.80 Min (254 nm), m/z=514.4 [M+H]. Total run time 3.75 min (short pos/neg), HP1100.

$^1$H NMR (d$_6$ DMSO): δ 1.12-1.25 (m, 1H), 1.43-1.53 (m, 1H), 1.65-1.75 (m, 2H), 1.95-2.30 (br s, 2H), 2.87-3.00 (m, 2H), 3.01-3.20 (m, 2H), 5.41 (s, 2H), 7.21 (dd, 2H), 7.33 (dd, 2H), 7.71 (s, 1H), 8.04 (s, 1H), 8.19 (s, 1H), 8.51 (br s, 1H), 9.75 (br s, 1H), 11.70 (br s, 1H) 1 proton not seen Example 18: 1-(4-Chloro-benzyl)-1H-pyrazole-4-carboxylic acid [4-((R)-3-amino-piperidin-1-yl)-5-bromo-1H-pyrrolo[2,3-b]pyridin-3-yl]-amide

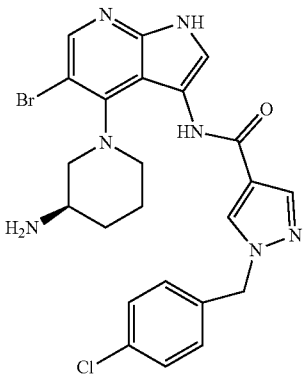 [SMILES: N[C@@H]1CCCN(c2c(Br)cnc3[nH]cc(NC(=O)c4cnn(Cc5ccc(Cl)cc5)c4)c23)C1]

The title compound (pale yellow solid, 19.6 mg, 17.3%) was prepared as described in Example 6, substituting 1-(4-chloro-benzyl)-1H-pyrazole-4-carboxylic acid (163 mg, 0.715 mmol), prepared in a similar manner to that described for 1-(4-fluoro-benzyl)-1H-pyrazole-4-carboxylic acid, for 1-benzyl-1H-pyrazole-4-carboxylic acid, in Step 7.

LC/MS: RT=1.87 Min (254 nm), m/z=530.4 [M+H]. Total run time 3.75 min (short pos/neg), HP1100.

$^1$H NMR (d$_6$ DMSO): δ 1.11-1.20 (m, 1H), 1.43-1.79 (m, 5H), 2.86-2.98 (m, 2H), 3.09-3.20 (m, 2H), 5.42 (s, 2H), 7.28 (d, 2H), 7.44 (d, 2H), 7.71 (s, 1H), 8.05 (s, 1H), 8.19 (s, 1H), 8.53 (br s, 1H), 9.77 (br s, 1H), 11.72 (br s, 1H) 1 proton not seen Example 19: 1-(4-Methyl-benzyl)-1H-pyrazole-4-carboxylic acid [4-((R)-3-amino-piperidin-1-yl)-5-bromo-1H-pyrrolo[2,3-b]pyridin-3-yl]-amide

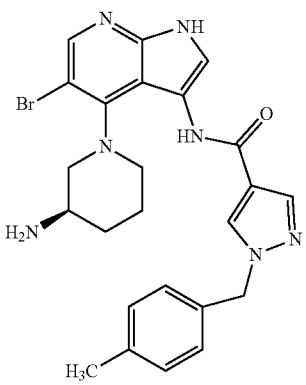 [SMILES: Cc1ccc(Cn2cc(C(=O)Nc3c[nH]c4ncc(Br)c(N5CCC[C@@H](N)C5)c34)cn2)cc1]

The title compound (tan solid, 22 mg, 18.5%) was prepared as described in Example 6, substituting 1-(4-methyl-benzyl)-1H-pyrazole-4-carboxylic acid (155 mg, 0.715 mmol), prepared in a similar manner to that described for 1-(4-fluoro-benzyl)-1H-pyrazole-4-carboxylic acid, for 1-benzyl-1H-pyrazole-4-carboxylic acid, in Step 7. LC/MS: RT=1.85 Min (254 nm), m/z=508.4 [M+H]. Total run time 3.75 min (short pos/neg), HP1100.

$^1$H NMR (d$_6$ DMSO): δ 1.11-1.25 (m, 1H), 1.43-1.53 (m, 1H), 1.65-1.77 (m, 2H), 2.13-2.70 (br s, 2H), 2.29 (s, 3H), 2.88-3.01 (m, 2H), 3.08-3.20 (m, 2H), 5.36 (s, 2H), 7.15-7.21 (m, 4H), 7.70 (s, 1H), 8.02 (s, 1H), 8.19 (s, 1H), 8.47 (br s, 1H), 9.74 (br s, 1H), 11.70 (br s, 1H) 1 proton not seen Example 20: 1-(4-Methoxy-benzyl)-11H-pyrazole-4-carboxylic acid [4-((R)-3-amino-piperidin-1-yl)-5-bromo-1H-pyrrolo[2,3-b]pyridin-3-yl]-amide

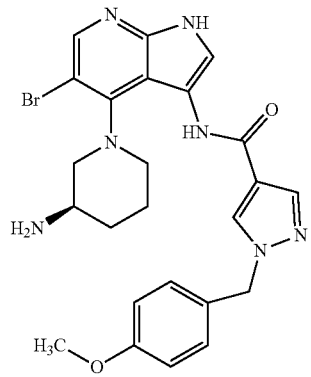 [SMILES: COc1ccc(Cn2cc(C(=O)Nc3c[nH]c4ncc(Br)c(N5CCC[C@@H](N)C5)c34)cn2)cc1]

The title compound (tan solid, 16.2 mg, 13.7%) was prepared as described in Example 6, substituting 1-(4-methoxy-benzyl)-1H-pyrazole-4-carboxylic acid (166 mg, 0.715 mmol), prepared in a similar manner to that described for 1-(4-fluoro-benzyl)-1H-pyrazole-4-carboxylic acid, for 1-benzyl-1H-pyrazole-4-carboxylic acid, in Step 7.

LC/MS: RT=1.79 Min (254 nm), m/z=524.4 [M+H]. Total run time 3.75 min (short pos/neg), HP1100.

$^1$H NMR (d$_6$ DMSO): δ 1.10-1.27 (m, 1H), 1.43-1.53 (m, 1H), 1.64-1.95 (m, 4H), 2.87-2.99 (m, 2H), 3.09-3.21 (m, 2H), 3.74 (s, 3H), 5.32 (s, 2H), 6.92 (d, 2H), 7.25 (d, 2H), 7.72 (s, 1H), 8.01 (s, 1H), 8.19 (s, 1H), 8.44 (br s, 1H), 9.73 (br s, 1H), 11.69 (br s, 1H) 1 proton not seen Example 21: 1-Pyridin-2-ylmethyl-1H-pyrazole-4-carboxylic acid [4-((R)-3-amino-piperidin-1-yl)-5-bromo-1H-pyrrolo[2,3-b]pyridin-3-yl]-amide

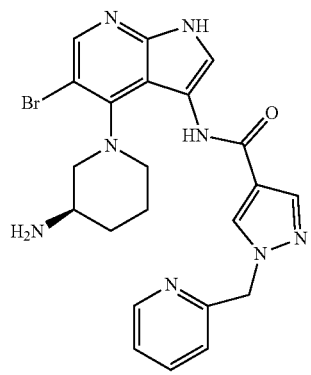 [SMILES: N[C@@H]1CCCN(c2c(Br)cnc3[nH]cc(NC(=O)c4cnn(Cc5ccccn5)c4)c23)C1]

The title compound (yellow solid, 40 mg, 68.7%) was prepared as described in Example 6, substituting 1-pyridin-2-ylmethyl-1H-pyrazole-4-carboxylic acid (150 mg, 0.74 mmol), prepared in a similar manner to that described for 1-pyridin-4-ylmethyl-1H-pyrazole-4-carboxylic acid in Example 81, Step 1, for 1-benzyl-1H-pyrazole-4-carboxylic acid, in Step 7. It was isolated as a formate salt following purification by preparative HPLC at pH4.

LC/MS: RT=0.87 Min (270 nm), m/z=497 [M+H]. Total run time 1.9 min (super short pos), HP1200.

¹H NMR (d₆ DMSO): d □ 11.21-1.34 (br m, 1H), 1.40-1.53 (br m, 1H), 1.59-1.68 (br m, 1H), 1.78-1.86 (br m, 1H), 2.98-3.08 (br m, 1H), 3.13-3.29 (br m, 3H), 3.33-3.44 (br m, 1H), 5.52 (s, 2H), 7.10 (d, 1H), 7.31-7.35 (m, 1H), 7.54 (s, 1H), 7.78-7.82 (m, 1H), 8.06 (s, 1H), 8.20 (s, 1H), 8.49-8.56 (m, 2H), 9.77 (br s, 1H) 3 protons not seen Example 22: 1-Pyridin-3-ylmethyl-1H-pyrazole-4-carboxylic acid [4-((R)-3-amino-piperidin-1-yl)-5-bromo-1H-pyrrolo[2,3-b]pyridin-3-yl]-amide

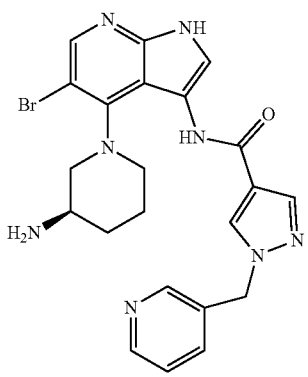 [SMILES: N[C@@H]1CCCN(c2c(Br)cnc3[nH]cc(NC(=O)c4cnn(Cc5cccnc5)c4)c23)C1]

The title compound (tan solid, 9.5 mg, 38%) was prepared as described in Example 6, substituting 1-pyridin-3-ylmethyl-1H-pyrazole-4-carboxylic acid (150 mg, 0.74 mmol) prepared in a similar manner to that described for 1-pyridin-4-ylmethyl-1H-pyrazole-4-carboxylic acid in Example 81, Step 1, for 1-benzyl-1H-pyrazole-4-carboxylic acid, in Step 7.

LC/MS: RT=0.83 Min (270 nm), m/z=497 [M+H]. Total run time 1.9 min (super short pos), HP1200.

¹H NMR (d₆ DMSO): δ 1.43-1.55 (br m, 1H), 1.61-1.69 (br m, 1H), 1.72-1.79 (br m, 1H), 3.03-3.22 (br m, 4H), 5.48 (s, 2H), 7.39-7.43 (m, 1H), 7.61 (s, 1H), 7.66-7.69 (m, 1H), 8.05 (s, 1H), 8.22 (s, 1H), 8.50-8.55 (m, 3H), 9.61 (br s, 1H), 11.81 (br s, 1H) 4 protons not seen Example 23: 1-Pyridin-4-ylmethyl-1H-pyrazole-4-carboxylic acid [4-((R)-3-amino-piperidin-1-yl)-5-bromo-1H-pyrrolo[2,3-b]pyridin-3-yl]-amide

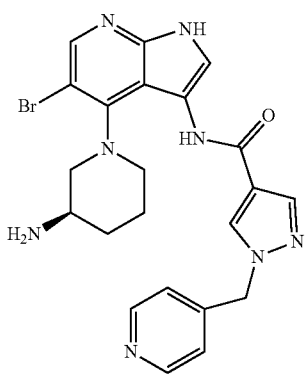 [SMILES: N[C@@H]1CCCN(c2c(Br)cnc3[nH]cc(NC(=O)c4cnn(Cc5ccncc5)c4)c23)C1]

The title compound (tan solid, 25 mg, 24%) was prepared as described in Example 6, substituting 1-pyridin-4-ylmethyl-1H-pyrazole-4-carboxylic acid (225 mg, 1.1 mmol), described in Example 81, Step 1, for 1-benzyl-1H-pyrazole-4-carboxylic acid, in Step 7.

LC/MS: RT=0.74 Min (254 nm), m/z=no mass [M+H]. Total run time 1.9 min (super short pos), HP1200.

¹H NMR (d₆ DMSO): d □ 1.10-1.20 (br m, 1H), 1.44-1.54 (br m, 1H), 1.61-1.80 (br m, 2H), 2.87-2.99 (br m, 2H), 3.09-3.23 (br m, 2H), 5.51 (s, 2H), 7.15 (d, 2H), 7.72 (s, 1H), 8.10 (s, 1H), 8.20 (s, 1H), 8.55 (d, 2H), 8.59 (s, 1H), 9.82 (s, 1H), 11.72 (br s, 1H) 4 protons not seen Example 24: N-{4-[(3R)-3-aminopiperidin-1-yl]-5-chloro-1H-pyrrolo[2,3-b]pyridin-3-yl}-1-benzyl-1H-pyrazole-4-carboxamide

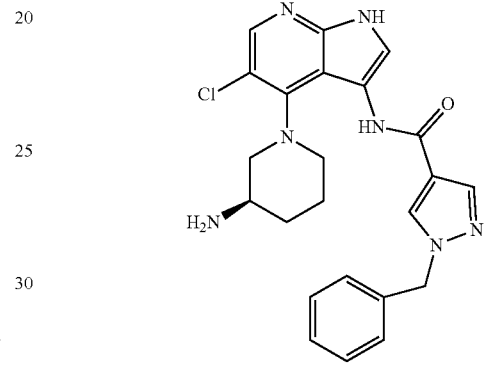

The title compound was prepared according to an analogous route to that outlined in Scheme 2.

The title compound was prepared as described in Example 6, Steps 1 and 2.

Step 3: 5-Chloro-4-fluoro-1H-pyrrolo[2,3-b]pyridine

4-Fluoro-1-[tris(propan-2-yl)silyl]-1H-pyrrolo[2,3-b] pyridine (2 g, 6.84 mmol) in THF (80 mL) at −78° C. was treated drop wise with sec-butyllithium solution, 1.4M in cyclohexane (4.48 mL, 6.27 mmol). The reaction was stirred at −78° C. for 0.5 hours. A solution of hexachloroethane (4.05 g, 17.1 mmol) in THF (20 mL) was added drop wise and the reaction was stirred at −78° C. for a further 0.5 hours. The reaction was quenched by the addition of saturated aqueous ammonium chloride. The mixture was extracted with iso-hexane (×2) and the combined extracts washed with saturated aqueous sodium chloride. The solution was dried over anhydrous MgSO4 and concentrated to a yellow gum.

The crude material was stirred in THF (50 mL) and tetrabutylammonium fluoride solution, 1.0M in THF (6.84 mL, 6.84 mmol) was added drop wise at RT. The reaction was stirred at RT for a further 1 hour before H₂O and EtOAc were added. The organic layer was separated and the aqueous phase was extracted with another portion of EtOAc. The combined organic phases were washed with saturated aqueous sodium chloride, dried (MgSO₄) and concentrated in vacuo to afford a pale orange solid. The crude residue was purified by automated flash chromatography eluting with iso-hexane to 40% EtOAc/iso-hexane. Fractions containing pure material were combined and solvent removed in vacuo to afford the desired product as a white solid 1.0 g, 85.7%

Step 4: Preparation of 5-chloro-4-fluoro-3-nitro-1H-pyrrolo[2,3-b]pyridine

This was prepared using the methodology described for Example 6, Step 5, substituting 5-chloro-4-fluoro-1H-pyrrolo[2,3-b]pyridine (1 g, 5.86 mmol) for 5-bromo-4-fluoro-1H-pyrrolo[2,3-b]pyridine. The title compound was isolated as a white solid, 1.15 g, 91.1%.

Step 5: Preparation of 5-Chloro-4-fluoro-1H-pyrrolo[2,3-b]pyridin-3-ylamine

This was prepared using the methodology described for Example 6, Step 6, substituting 5-chloro-4-fluoro-3-nitro-1H-pyrrolo[2,3-b]pyridine (202.9 mg, 0.94 mmol) for 5-bromo-4-fluoro-3-nitro-1H-pyrrolo[2,3-b]pyridine. The title compound was isolated as a solid, 167.4 mg, 95.8%.

Step 6: Preparation of 1-benzyl-1H-pyrazole-4-carboxylic acid (5-chloro-4-fluoro-1H-pyrrolo[2,3-b]pyridin-3-yl)-amide 5-Chloro-4-fluoro-1H-pyrrolo[2,3-b]pyridin-3-ylamine (167.4 mg, 0.90 mmol) was stirred in DMF (9.0 mL) with Et$_3$N (0.25 mL, 1.80 mmol) and 1-benzyl-1H-pyrazole-4-carboxylic acid (200.6 mg, 0.99 mmol). HATU (342.2 mg, 0.90 mmol) was added and the reaction was stirred at RT for 2 hours. The reaction mixture was diluted with H$_2$O, and extracted with EtOAc (3×30 mL). The combined extracts were washed with saturated aqueous sodium bicarbonate, saturated aqueous sodium chloride (4×60 mL), dried (MgSO$_4$) and solvent removed in vacuo to afford a brown gum. This was triturated with Et$_2$O, filtered and washed with Et$_2$O prior to drying in vacuo at 40° C. This afforded the title compound as an off white solid, 240.5 mg, 72.1%.

Step 7: Preparation of title compound: N-{4-[(3R)-3-aminopiperidin-1-yl]-5-chloro-1H-pyrrolo[2,3-b]pyridin-3-yl}-1-benzyl-1H-pyrazole-4-carboxamide A solution of 1-benzyl-1H-pyrazole-4-carboxylic acid (5-chloro-4-fluoro-1H-pyrrolo[2,3-b]pyridin-3-yl)-amide (100.0 mg, 0.27 mmol) in n-BuOH (5.4 mL) was treated with (R)-piperidin-3-yl-carbamic acid tert-butyl ester (270.8 mg, 1.35 mmol) and heated under microwave irradiation at 160° C. for 6 hours. The solvent was removed in vacuo and residue was taken up in DCM (5 mL). TFA (5 mL) was added and the reaction stirred at RT for 18 hours. The reaction mixture was concentrated in vacuo, the residue taken up in EtOAc (40 mL), washed with aqueous ammonia solution (2×50 mL), saturated aqueous sodium chloride, dried (MgSO$_4$) and concentrated in vacuo. The crude material was purified by automated column chromatography, eluting with DCM to 10% MeOH/DCM (gradient). The fractions containing pure product were combined and concentrated in vacuo to afford the title compound as a cream solid, 53.6 mg, 44.1%.

LC/MS: RT=1.77 Min (270 nm), m/z=450.4 [M+H]. Total run time 3.75 min (short pos/neg), HP1100.

$^1$H NMR (d$_6$ DMSO): δ 1.16-1.21 (m, 1H), 1.45-1.49 (m, 1H), 1.66-1.74 (m, 4H), 2.90-2.94 (m, 2H), 3.13-3.16 (m, 2H), 5.42 (s, 2H), 7.26-7.39 (m, 5H), 7.73 (s, 1H), 8.04 (s, 1H), 8.08 (s, 1H), 8.53 (s, 1H), 9.73 (br s, 1H), 11.68 (s, 1H) 1 proton not seen

Example 25: 1-(4-Methyl-benzyl)-1H-pyrazole-4-carboxylic acid [4-((R)-3-amino-piperidin-1-yl)-5-chloro-1H-pyrrolo[2,3-b]pyridin-3-yl]-amide

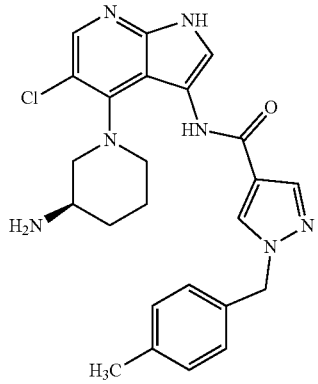 [SMILES: Cc1ccc(Cn2cc(C(=O)Nc3c[nH]c4ncc(Cl)c(N5CCC[C@@H](N)C5)c34)cn2)cc1]

The title compound (cream solid, 24 mg, 28.4%) was prepared as described in Example 24, substituting 1-(4-methyl-benzyl)-1H-pyrazole-4-carboxylic acid (256.3 mg, 1.19 mmol) for 1-benzyl-1H-pyrazole-4-carboxylic acid, in Step 6.

LC/MS: RT=1.82 Min (254 nm), m/z=464 [M+H]. Total run time 3.75 min (short pos)HP1100.

$^1$H NMR (d$_6$ DMSO): ☐☐, 1.18 (m, 1H), 1.52 (m, 2H), 1.68 (m, 2H), 2.33 (2, 3H), 2.91 (m, 2H), 3.14 (m, 2H), 3.33 (m, 2H), 5.36 (s, 2H), 7.19 (m, 4H), 7.75 (s, 1H), 8.03 (s, 1H), 8.09 (s, 1H), 8.50 (s, 1H), 9.73 (s, 1H), 11.69 (s, 1H)

Example 26: 1-(4-Fluoro-benzyl)-1H-pyrazole-4-carboxylic acid [4-((R)-3-amino-piperidin-1-yl)-5-chloro-1H-pyrrolo[2,3-b]pyridin-3-yl]-amide

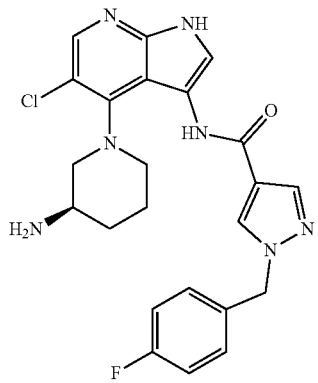 [SMILES: N[C@@H]1CCCN(c2c(Cl)cnc3[nH]cc(NC(=O)c4cnn(Cc5ccc(F)cc5)c4)c23)C1]

The title compound (cream solid, 24.2 mg, 20.1%) was prepared as described in Example 24, substituting 1-(4-fluoro-benzyl)-1H-pyrazole-4-carboxylic acid (261 mg, 1.19 mmol) for 1-benzyl-1H-pyrazole-4-carboxylic acid, in Step 6 LC/MS: RT=1.77 Min (270 nm), m/z=468.5 [M+H]. Total run time 3.75 min (short pos/neg), HP1100.

$^1$H NMR (d$_6$ DMSO): δ 1.18-1.23 (m, 1H), 1.45-1.50 (m, 1H), 1.68-1.70 (m, 2H), 2.94-2.99 (m, 2H), 3.11-3.13 (m, 2H), 5.41 (s, 2H), 7.19-7.23 (m, 2H), 7.32-7.36 (m, 2H), 7.71 (s, 1H), 8.04 (s, 1H), 8.09 (s, 1H), 8.51 (s, 1H), 9.69 (br s, 1H), 11.71 (br s, 1H) 3 protons not seen Example 27: 1-(4-Chloro-benzyl)-1H-pyrazole-4-carboxylic acid [4-((R)-3-amino-piperidin-1-yl)-5-chloro-1H-pyrrolo[2,3-b]piperidin-3-yl]-amide

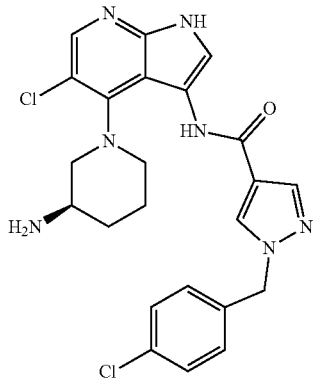 [SMILES: N[C@@H]1CCCN(c2c(Cl)cnc3[nH]cc(NC(=O)c4cnn(Cc5ccc(Cl)cc5)c4)c23)C1]

The title compound (cream solid, 22.1 mg, 18.4%) was prepared as described in Example 24, substituting 1-(4-chloro-benzyl)-1H-pyrazole-4-carboxylic acid (280.5 mg, 1.19 mmol) for 1-benzyl-1H-pyrazole-4-carboxylic acid, in Step 6.

LC/MS: RT=1.84 Min (270 nm), m/z=484.4 [M+H]. Total run time 3.75 min (short pos/neg), HP1100.

$^1$H NMR (d$_6$ DMSO): δ 1.15-1.20 (m, 1H), 1.45-1.49 (m, 1H), 1.66-1.72 (m, 2H), 2.92-2.96 (m, 2H), 3.13-3.16 (m, 2H), 5.42 (s, 2H), 7.29 (d, 2H), 7.44 (d, 2H), 7.72 (s, 1H), 8.05 (s, 1H), 8.09 (s, 1H), 8.53 (s, 1H), 9.72 (br s, 1H), 11.70 (br s, 1H) 3 protons not seen Example 28: 1-(4-Methoxy-benzyl)-1H-pyrazole-4-carboxylic acid [4-((R)-3-amino-piperidin-1-yl)-5-chloro-1H-pyrrolo[2,3-b]pyridin-3-yl]-amide

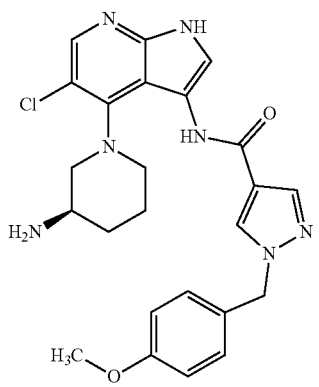 [SMILES: COc1ccc(Cn2cc(C(=O)Nc3c[nH]c4ncc(Cl)c(N5CCC[C@@H](N)C5)c34)cn2)cc1]

The title compound (white solid, 24 mg, 19.8%) was prepared as described in Example 24, substituting 1-(4-methoxy-benzyl)-1H-pyrazole-4-carboxylic acid (275.3 mg, 1.19 mmol) for 1-benzyl-1H-pyrazole-4-carboxylic acid, in Step 6. LC/MS: RT=1.77 Min (254 nm), m/z=480 [M+H]. Total run time 3.75 min (short pos/neg), HP1100.

$^1$H NMR (d$_6$ DMSO): δ 1.17 (m, 1H), 1.49 (m, 2H), 1.71 (m, 2H), 2.91 (m, 2H), 3.14 (m, 2H), 3.33 (m, 2H), 3.75 (s, 3H), 5.33 (s, 2H), 6.94 (d, J 8.68, 2H), 7.27 (d, J 865, 2H), 7.75 (s, 1H), 8.01 (s, 1H), 8.08 (s, 1H), 8.46 (s, 1H), 9.71 (s, 1H), 11.65 (s, 1H)

Example 29: 1-Benzyl-1H-pyrazole-4-carboxylic acid [4-((R)-3-amino-pyrrolidin-1-yl-5-chloro-1H-pyrrolo[2,3-b]pyridin-3-yl]-amide

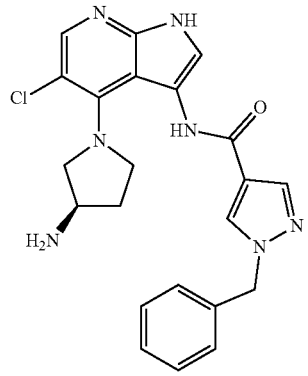 [SMILES: N[C@@H]1CCN(c2c(Cl)cnc3[nH]cc(NC(=O)c4cnn(Cc5ccccc5)c4)c23)C1]

The title compound (white solid, 42.5 mg, 60.1%) was prepared as described in Example 24, substituting (R)-pyrrolidin-3-yl-carbamic acid tert-butyl ester (151.1 mg, 0.81 mmol) for (R)-piperidin-3-yl-carbamic acid tert-butyl ester, in Step 7.

LC/MS: RT=1.71 Min (254 nm), m/z=436.4 [M+H]. Total run time 3.75 min (short pos/neg), HP1100.

$^1$H NMR (d$_6$ DMSO): δ 1.66-1.72 (m, 1H), 2.09-2.17 (m, 1H), 3.02-3.05 (m, 1H), 3.37-3.43 (m, 1H), 3.51-3.58 (m, 2H), 3.63-3.68 (m, 1H), 5.39 (s, 2H), 7.28-7.39 (m, 5H), 7.76 (s, 1H), 8.10 (s, 1H), 8.14 (s, 1H), 8.66 (s, 1H), 9.78 (s, 1H), 11.60 (br s, 1H) 2 protons not seen Example 30: N-{4-[(3R)-3-aminopiperidin-1-yl]-5-cyclopropyl-1H-pyrrolo[2,3-b]pyridin-3-yl}-1-benzyl-1H-pyrazole-4-carboxamide

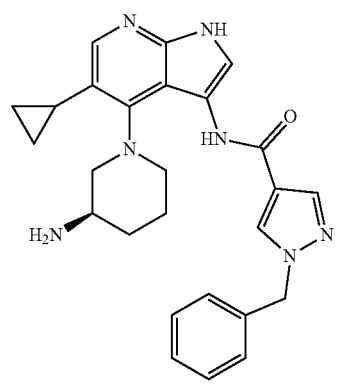 [SMILES: N[C@@H]1CCCN(c2c(C3CC3)cnc3[nH]cc(NC(=O)c4cnn(Cc5ccccc5)c4)c23)C1]

The title compound was prepared from ((R)-1-{3-[(1-benzyl-1H-pyrazole-4-carbonyl)-amino]-5-bromo-1H-pyrrolo[2,3-b]pyridin-4-yl}-piperidin-3-yl)-carbamic acid tert-butyl ester, the product of Step 1, Example 53.

((R)-1-{3-[(1-benzyl-1H-pyrazole-4-carbonyl)-amino]-5-bromo-1H-pyrrolo[2,3-b]pyridin-4-yl}-piperidin-3-yl)-carbamic acid tert-butyl ester (29 mg, 0.05 mmol), cyclopropylboronic acid (8.4 mg, 0.1 mmol), Pd(dppf)Cl$_2$ (5.1 mg, 0.01 mol) and K$_2$CO$_3$ (27.6 mg, 0.20 mmol) and THF (4.5 mL)/H$_2$OH$_2$O (0.5 mL) were charged to a microwave vial and degassed. The contents were heated under microwave irradiation at 120° C. for 1 hour. The reaction mixture was partitioned between EtOAc and H$_2$OH$_2$O, then the organic layer was separated and the aqueous extracted with another portion of EtOAc. The combined organics were washed with saturated aqueous sodium hydrogen bicarbonate, H$_2$OH$_2$O, saturated aqueous sodium chloride, dried (MgSO$_4$) and solvent removed in vacuo to give crude ((R)-1-{3-[(1-benzyl-1H-pyrazole-4-carbonyl)-amino]-5-cyclopropyl-1H-pyrrolo[2,3-b]pyridin-4-yl}-piperidin-3-yl)-carbamic acid tert-butyl ester as a yellow oil.

This material was taken up in hydrochloric acid solution, 1.25 M in MeOH (5 mL) and irradiated in a microwave for 1 hour at 80° C. The volatiles were removed in vacuo and the residue was taken up in the minimum volume of MeOH and loaded onto a SCX2 ion exchange column that had been primed with MeOH. The column was washed with DCM, MeOH and the title compound was eluted using ammonia solution, 3.5M in MeOH. This solution was concentrated in vacuo and the residue was purified by preparative HPLC at pH4 and then at pH9. The material was taken up in acetone and filtered through a plug of potassium carbonate. The filtrate was concentrated in vacuo to afford the title compound as a solid, 1.5 mg, 6.8%.

LC/MS: RT=1.56 Min (270 nm), m/z=456 [M+H]. Total run time 3.75 min (short pos/neg), HP1100.

$^1$H NMR (d$_4$ MeOH): δ 0.72-1.07 (m, 4H), 1.20-2.18 (m, 5H), 3.16-3.24 (m, 1H), 3.37-3.52 (m, 3H), 5.41 (s, 2H), 7.28-7.42 (m, 5H), 7.66 (s, 1H), 7.96 (s, 1H), 8.10 (s, 1H), 8.32 (s, 1H) 5 protons not seen Example 31: 1-Benzyl-1H-pyrazole-4-carboxylic acid [4-((R)-3-amino-piperidin-1-yl)-5-hydroxy-1H-pyrrolo[2,3-b]pyridin-3-yl]-amide

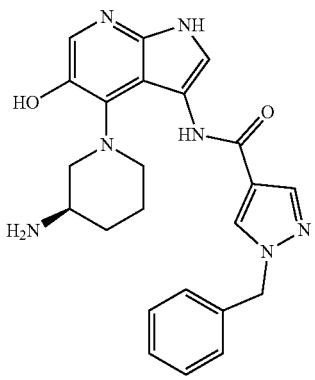 [SMILES: N[C@@H]1CCCN(c2c(O)cnc3[nH]cc(NC(=O)c4cnn(Cc5ccccc5)c4)c23)C1]

The title compound was prepared according to the route outlined in Scheme 9. The title compound was prepared as described in Example 6. In Step 3, (2R,8aS)-(+)-(camphorylsulfonyl)oxaziridine (2.55 g, 11.1 mmol) was used as the electrophile instead of carbon tetrabromide Following the usual work up, purification by flash column chromatography eluting with iso-hexane and then 5% EtOAc/iso-hexane, the desired intermediate, 4-fluoro-1-triisopropylsilanyl-1H-indol-5-ol, was isolated as a pale yellow oil, 0.91 g, 66.5%.

Step 4: Preparation of 2,2-dimethyl-propionic acid 4-fluoro-1-triisopropylsilanyl-1H-pyrrolo[2,3-b]pyridin-5-yl ester To a solution of 4-fluoro-1-triisopropylsilanyl-1H-indol-5-ol (1 g, 3.24 mmol) and Et$_3$N (0.45 mL, 3.24 mmol) in DCM (1 mL) was added pivaloyl chloride (0.8 mL, 6.5 mmol) and stirred at RT for 3 hours. The mixture was diluted with DCM (30 mL) and washed with H$_2$O, saturated aqueous sodium chloride, dried over anhydrous Na$_2$SO$_4$ and concentrated in vacuo. The crude material was purified by flash column chromatography to give the title compound as a clear oil, 055 g, 43.2%.

Step 5: Preparation of 2,2-dimethyl-propionic acid 4-fluoro-1H-pyrrolo[2,3-b]pyridin-5-yl ester Tetrabutylammonium fluoride solution, 1.0M in THF (2.8 mL, 2.8 mmol) was added drop wise to a solution of 2,2-dimethyl-propionic acid 4-fluoro-1-triisopropylsilanyl-1H-pyrrolo[2,3-b]pyridin-5-yl ester (550 mg, 1.4 mmol) in THF (10 mL) at 0° C. After addition, stirring was continued for a further 1.5 hours at RT. EtOAc was added and the mixture washed with H$_2$O and saturated aqueous sodium chloride. The organics were dried over MgSO$_4$, concentrated in vacuo and the crude material obtained was purified by flash chromatography eluting with 33% EtOAc/iso-hexane. Fractions containing pure product were combined and concentrated in vacuo to afford the title compound as a white solid, 270 mg, 81.6%.

Step 6: Preparation of 2,2-dimethyl-propionic acid 4-fluoro-3-nitro-1H-pyrrolo[2,3-b]pyridin-5-yl ester This was prepared using the methodology described for Example 6, Step 5, substituting 2,2-dimethyl-propionic acid 4-fluoro-1H-pyrrolo[2,3-b]pyridin-5-yl ester (270 mg, 1.14 mmol) for 5-bromo-4-fluoro-1H-pyrrolo[2,3-b]pyridine. The title compound was isolated as a pale yellow solid, 321 mg, 99.9%.

Step 7: Preparation of 2,2-dimethyl-propionic acid 4-((R)-3-tert-butoxycarbonylamino-piperidin-1-yl)-3-nitro-1H-pyrrolo[2,3-b]pyridin-5-yl ester 2,2-Dimethyl-propionic acid 4-fluoro-3-nitro-1H-pyrrolo [2,3-b]pyridin-5-yl ester (95 mg, 0.34 mmol), (R)-piperidin-3-yl-carbamic acid tert-butyl ester (81 mg, 0.4 mmol), DIPEA (89 uL, 0.51 mmol) and 1-butanol (2 mL) were combined in a microwave vial and then heated at 120° C. for 2 hours under microwave irradiation. The mixture was concentrated in vacuo and the residue purified by flash chromatography eluting with 25% EtOAc/iso-hexane. Fractions containing product were combined and concentrated in vacuo to give the title compound as a yellow solid 73 mg, 46.5%.

Step 8: Preparation of 2,2-dimethyl-propionic acid 3-amino-4-((R)-3-tert-butoxycarbonylamino-piperidin-1-yl)-1H-pyrrolo[2,3-b]pyridin-5-yl ester To a mixture of 2,2-dimethyl-propionic acid 4-((R)-3-tert-butoxycarbonylamino-piperidin-1-yl)-3-nitro-1H-pyrrolo[2,3-b]pyridin-5-yl ester (73 mg, 0.158 mmol) and Et$_3$N (0.2 mL) in MeOH (20 mL) was added Raney Nickel, 50% slurry in H$_2$O (10 mg). The reaction was stirred at RT an atmosphere of hydrogen for 18 hours. The catalyst was removed via filtration and the filtrate concentrated in vacuo to afford the title compound as a brown solid, 68 mg, 100%.

Step 9: Preparation of 2,2-dimethyl-propionic acid 3-[(1-benzyl-1H-pyrazole-4-carbonyl)-amino]-4-((R)-3-tert-butoxycarbonylamino-piperidin-1-yl)-1H-pyrrolo[2,3-b]pyridin-5-yl ester 2,2-Dimethyl-propionic acid 3-amino-4-((R)-3-tert-butoxycarbonylamino-piperidin-1-yl)-1H-pyrrolo[2,3-b]pyridin-5-yl ester (68 mg, 0.158 mmol) and 1-benzyl-1H-pyrazole-4-carboxylic acid (32 mg, 0.158 mmol) were stirred in DMF (5 mL) at RT To this was added triethylamine (0.04 mL, 5.74 mmol) followed by HATU (60 mg, 0.158 mmol) and the mixture was stirred at room temperature for 5 hours. The resulting solution was concentrated in vacuo and the resultant brown gum was taken up in EtOAc (100 mL). It was washed with H₂O (2×60 mL), saturated aqueous sodium chloride (20 mL), dried (MgSO₄) and concentrated in vacuo. The crude material was purified by flash column chromatography to afford the title compound as a brown solid, 63 mg, 64.8%.

Step 10: Preparation of ((R)-1-{3-[(1-benzyl-1H-pyrazole-4-carbonyl)-amino]-5-hydroxy-1H-pyrrolo[2,3-b]pyridin-4-yl}-piperidin-3-yl)-carbamic acid tert-butyl ester To a solution of 2,2-dimethyl-propionic acid 3-[(1-benzyl-1H-pyrazole-4-carbonyl)-amino]-4-((R)-3-tert-butoxycarbonylamino-piperidin-1-yl)-1H-pyrrolo[2,3-b]pyridin-5-yl ester (382 mg, 0.62 mmol, in ethanol (15 mL) was added aqueous NaOH, 4N (1.5 mL, 6 mmol) and the reaction was stirred at RT for 2 hours. The solvent was removed in vacuo and the residue was carefully neutralized to pH7 with HCl, 6N. The mixture was extracted with EtOAc (3×40 mL) and the combined extracts washed with saturated aqueous sodium chloride (×3), dried over Na₂SO₄ and concentrated in vacuo. The crude material was purified twice by flash column chromatography eluting with 6% MeOH/DCM and the fractions containing pure product were combined and concentrated in vacuo to give the title compound as a pale brown solid 115 mg, 34.9%.

Step 11: Preparation of title compound: 1-benzyl-1H-pyrazole-4-carboxylic acid [4-((R)-3-amino-piperidin-1-yl)-5-hydroxy-1H-pyrrolo[2,3-b]pyridin-3-yl]-amide ((R)-1-{3-[(1-Benzyl-1H-pyrazole-4-carbonyl)-amino]-5-hydroxy-1H-pyrrolo[2,3-b]pyridin-4-yl}-piperidin-3-yl)-carbamic acid tert-butyl ester (115 mg, 0.216 mmol) was stirred in MeOH (4 mL) and hydrochloric acid solution, 4N in MeOH (1 mL) was added. The mixture was stirred at RT for 18 hours and then neutralized (pH 7) by the careful addition of ammonium hydroxide solution. DCM (70 mL) was added and the mixture washed with H₂O (2×20 mL), saturated aqueous sodium chloride (2×20 mL), dried over Na₂SO₄ and concentrated in vacuo to afford the title compound as the hydrochloride salt, 75 mg, 80.5%.
LC/MS: RT=2.02 Min (270 nm), m/z=432 [M+H]. Total run time 7.5 min (long pos), HP1100.
¹H NMR (d₆ DMSO): □ 1.35-1.48 (m, 2H), 1.59-1.69 (m, 1H), 1.84-1.91 (m, 1H), 2.99-3.11 (m, 2H), 3.17-3.38 (m, 2H), 5.42 (s, 2H), 7.24-7.28 (m, 2H), 7.30-7.40 (m, 3H), 7.50 (d, 1H), 7.88 (s, 1H), 7.99 (br s, 3H), 8.02 (s, 1H), 8.42 (s, 1H), 9.31 (br s, 1H), 9.52 (s, 1H), 11.39 (s, 1H) 1 proton not seen Example 32: 1-Benzyl-1H-pyrazole-4-carboxylic acid [4-((R)-3-amino-piperidin-1-yl-5-methoxy-1H-pyrrolo[2,3-b]pyridin-3-yl]-amide

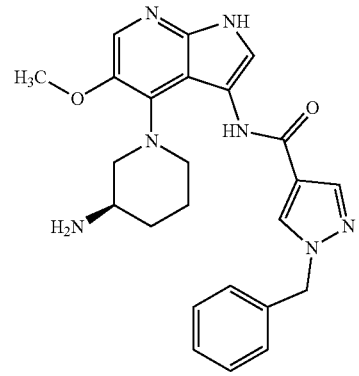 [SMILES: COc1cnc2[nH]cc(NC(=O)c3cnn(Cc4ccccc4)c3)c2c1N1CCC[C@@H](N)C1]

The title compound was prepared from 4-fluoro-1-triisopropylsilanyl-1H-indol-5-ol, the product of Step 3, in Example 31.

Step 1: Preparation of 4-Fluoro-5-methoxy-1-triisopropylsilanyl-1H-pyrrolo[2,3-b]pyridine Diisopropyl azodicarboxylate (688 mg, 3.4 mmol) was added drop wise to a solution of 4-fluoro-1-triisopropylsilanyl-1H-indol-5-ol (805 mg, 2.61 mmol) and triphenylphosphine (892 mg, 3.44 mmol) in THF (25 mL) at 0° C. and the reaction stirred for 10 mins. MeOH (1 mL, 24.7 mmol) was added and the mixture stirred for a further 1 hour at 0° C. and then RT for 1 hour. The solution was concentrated in vacuo to a dark yellow gum. The crude material was purified by column chromatography eluting with iso-hexane to 3% EtOAc/iso-hexane. Fractions containing pure product were combined and concentrated in vacuo to afford the title compound as a pale yellow oil, 680 mg, 80.8%.

Step 2: Preparation of 4-Fluoro-5-methoxy-1H-pyrrolo[2,3-b]pyridine

This was prepared using the methodology described for Example 31, Step 5, substituting 4-fluoro-5-methoxy-1-triisopropylsilanyl-1H-pyrrolo[2,3-b]pyridine (630 mg, 1.95 mmol) for 2,2-dimethyl-propionic acid 4-fluoro-1-triisopropylsilanyl-1H-pyrrolo[2,3-b]pyridin-5-yl ester. The title compound was isolated as a pale yellow solid, 285 mg, 87.8%.

Step 3: Preparation of 4-Fluoro-5-methoxy-3-nitro-1H-pyrrolo[2,3-b]pyridine

This was prepared using the methodology described for Example 6, Step 5, substituting 4-fluoro-5-methoxy-1H-pyrrolo[2,3-b]pyridine (280 mg, 1.69 mmol) for 5-bromo-4-fluoro-1H-pyrrolo[2,3-b]pyridine. The title compound was isolated as a pale yellow solid, 325 mg, 91.3%.

Step 4: Preparation of [(R)-1-(5-methoxy-3-nitro-1H-pyrrolo[2,3-b]pyridin-4-yl)-piperidin-3-yl]-carbamic acid tert-butyl ester This was prepared using the methodology described for Example 31, Step 7, substituting 4-fluoro-5-methoxy-3-nitro-1H-pyrrolo[2,3-b]pyridine (270 mg, 1.28 mmol) for 2,2-dimethyl-propionic acid 4-fluoro-3-nitro-1H-pyrrolo[2,3-b]pyridin-5-yl ester. The title compound was isolated as a yellow solid, 385 mg, 76.9%.

Step 5: Preparation of [(R)-1-(3-amino-5-methoxy-1H-pyrrolo[2,3-b]pyridin-4-yl)-piperidin-3-yl]-carbamic acid tert-butyl ester This was prepared using the methodology described for Example 31, Step 8, substituting [(R)-1-(5-methoxy-3-nitro-1H-pyrrolo[2,3-b]pyridin-4-yl)-piperidin-3-yl]-carbamic acid tert-butyl ester (130 mg, 0.332 mmol) for 2,2-dimethyl-propionic acid 4-((R)-3-tert-butoxycarbonylamino-piperidin-1-yl)-3-nitro-1H-pyrrolo[2,3-b]pyridin-5-yl ester. The title compound was isolated as a brown oil, 120 mg, 100%.

Step 6: Preparation of ((R)-1-{3-[(1-benzyl-1H-pyrazole-4-carbonyl)-amino]-5-methoxy-1H-pyrrolo[2,3-b]pyridin-4-yl}-piperidin-3-yl)-carbamic acid tert-butyl ester This was prepared using the methodology described for Example 31, Step 9, substituting [(R)-1-(3-amino-5-methoxy-1H-pyrrolo[2,3-b]pyridin-4-yl)-piperidin-3-yl]-carbamic acid tert-butyl ester (120 mg, 0.332 mmol) for 2,2-dimethyl-propionic acid 3-amino-4-((R)-3-tert-butoxycarbonylamino-piperidin-1-yl)-1H-pyrrolo[2,3-b]pyridin-5-yl ester. The title compound was isolated as a pale brown solid, 68 mg, 37.5%.

Step 7: Preparation of title compound: 1-benzyl-1H-pyrazole-4-carboxylic acid [4-((R)-3-amino-piperidin-1-yl)-5-methoxy-1H-pyrrolo[2,3-b]pyridin-3-yl]-amide To a solution of ((R)-1-{3-[(1-benzyl-1H-pyrazole-4-carbonyl)-amino]-5-methoxy-1H-pyrrolo[2,3-b]pyridin-4-yl}-piperidin-3-yl)-carbamic acid tert-butyl ester (320 mg, 0.58 mmol) in MeOH (10 mL) was added hydrochloric acid solution, 3.0 M in MeOH (2 mL) at 0° C. After addition the reaction mixture was stirred at 50° C. for 3 hours and then concentrated in vacuo. The residue was partitioned between saturated aqueous sodium carbonate (15 mL) and 20% MeOH in DCM (100 mL). The organics were separated, washed with H₂O, saturated aqueous sodium chloride and dried over anhydrous Na₂SO₄. The solvent was removed in vacuo and the crude material purified by flash column chromatography to give the title compound as an off white solid, 105 mg, 73%.

LC/MS: RT=2.14 Min (270 nm), m/z=446 [M+H]. Total run time 7.5 min (long pos), HP1100.

¹H NMR (d₆ DMSO): δ 1.15-1.25 (m, 1H), 1.40-1.51 (m, 1H), 1.67-1.76 (m, 2H), 2.25 (br s, 2H), 2.82-2.94 (m, 2H), 3.00-3.08 (m, 2H), 3.19-3.25 (m, 1H), 3.85 (s, 3H), 5.41 (s, 2H), 7.25-7.40 (m, 5H), 7.71 (s, 1H), 8.01 (s, 1H), 8.07 (s, 1H), 8.54 (s, 1H), 9.71 (br s, 1H), 11.22 (br s, 1H).

Example 33: 1-Benzyl-1H-pyrazole-4-carboxylic acid [4-((R)-3-amino-piperidin-1-yl)-5-methyl-1H-pyrrolo[2,3-b]pyridin-3-yl]-amide

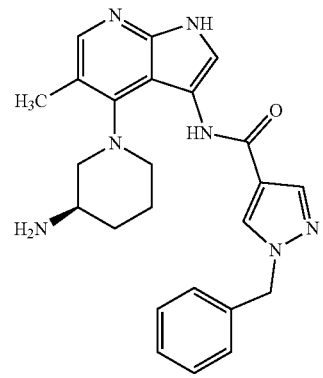 [SMILES: Cc1cnc2[nH]cc(NC(=O)c3cnn(Cc4ccccc4)c3)c2c1N1CCC[C@@H](N)C1]

The title compound was prepared from ((R)-1-{3-[(1-benzyl-1H-pyrazole-4-carbonyl)-amino]-5-bromo-1H-pyrrolo[2,3-b]pyridin-4-yl}-piperidin-3-yl)-carbamic acid tert-butyl ester, the product of Step 1, Example 53.

((R)-1-{3-[(1-benzyl-1H-pyrazole-4-carbonyl)-amino]-5-bromo-1H-pyrrolo[2,3-b]pyridin-4-yl}-piperidin-3-yl)-carbamic acid tert-butyl ester (48.0 mg, 0.08 mMmol), methylboronic acid (8.70 mg, 0.15 mMmol). Pd(dppf)Cl₂ (7.0 mg, 0.01 mMmol) and K₂CO₃ (22.1 mg, 0.16 mMmol) and THF (4.5 mL)/H₂O (0.5 mL) were charged to a microwave vial and degassed. The contents were heated under microwave irradiation at 120° C. for 2 hours. The reaction mixture was partitioned between EtOAc and H₂O, then the organic layer was separated and the aqueous extracted with another portion of EtOAc. The combined organics were washed with H₂O, saturated aqueous sodium chloride, dried (MgSO₄) and solvent removed in vacuo. The crude product was purified by automated column chromatography eluting with iso-hexane to 15% EtOAc/iso-hexane (gradient). Fractions found to contain pure material were combined and solvent removed in vacuo to afford ((R)-1-{3-[(1-benzyl-1H-pyrazole-4-carbonyl)-amino]-5-methyl-1H-pyrrolo[2,3-b]pyridin-4-yl}-piperidin-3-yl)-carbamic acid tert-butyl ester. This was taken up in DCM (5 mL) and trifluoroacetic acid (0.05 mL, 0.6 mMmol) was added drop wise and the reaction was allowed to stir for 2 hours at RT. Trifluoroacetic acid (0.05 mL, 0.6 mMmol) was added and the reaction was stirred for a further 1 hour at RT. The volatiles were removed in vacuo and residue was partitioned between DCM and H₂O. The organic layer was separated and washed with saturated aqueous sodium chloride, dried (MgSO₄) and the volatiles removed in vacuo. The residue was purified by preparative HPLC at pH9, taken up in acetone and filtered through a plug of potassium carbonate. The filtrate was concentrated in vacuo to afford the title compound as a solid, 4 mg, 11.5%.

LC/MS: RT=1.61 Min (270 nm), m/z=430 [M+H]. Total run time 3.75 min (short pos/neg), HP1100.

¹H NMR (d₆ MeOH) δ 1.11-1.23 (m, 1H), 1.50-1.64 (m, 1H), 1.69-1.76 (m, 1H), 1.78-1.87 (m, 1H), 2.44 (s, 3H), 2.83-2.97 (m, 2H), 3.08-3.23 (m, 2H), 5.42 (s, 2H), 7.28-7.41 (m, 5H), 7.62 (s, 1H), 7.93 (s, 1H), 8.04 (s, 1H), 8.24 (s, 1H) 5 protons not seen Example 34: 1-Benzyl-1H-pyrazole-4-carboxylic acid [5-(4-piperidin-1-ylmethyl-phenyl)-1H-pyrrolo[2,3-b]pyridin-3-yl]-amide

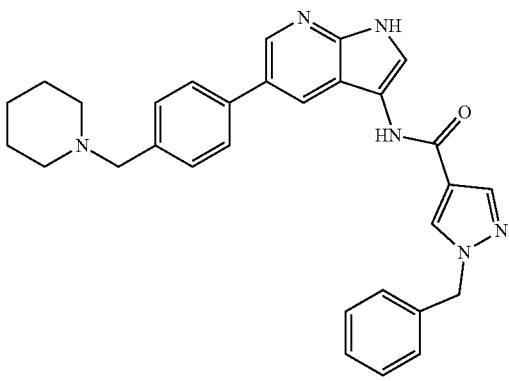 [SMILES: O=C(Nc1c[nH]c2ncc(-c3ccc(CN4CCCCC4)cc3)cc12)c1cnn(Cc2ccccc2)c1]

The title compound was made according to the route outlined in Scheme 3. The title compound was prepared from Example 1.

Step 1: Preparation of 1-Benzyl-1H-pyrazole-4-carboxylic acid [5-(4-formyl-phenyl)-1H-pyrrolo[2,3-b]pyridin-3-yl]-amide 1-Benzyl-1H-pyrazole-4-carboxylic acid (5-bromo-1H-pyrrolo[2,3-b]pyridin-3-yl)-amide (100 mg, 0.25 mmol), 4-formylphenylboronic acid (41.6 mg, 0.28 mmol), $K_2CO_3$ (103.7 mg, 0.75 mmol) and Pd(dppf)Cl$_2$ (18.3 mg, 0.025 mmol) were combined in THF/$H_2O$ (2.1 mL:0.23 mL) and thoroughly degassed. The reaction mixture was heated at 120° C. for 1 hour under microwave irradiation. The reaction was diluted with EtOAc, washed with $H_2O$, the aqueous was extracted again with EtOAc and the combined organics were washed with saturated aqueous sodium chloride, dried (MgSO$_4$) and solvent removed in vacuo to afford a brown gum. This crude material was purified by automated column chromatography, eluting with DCM to 7% MeOH/DCM (gradient). Fractions found to contain pure material were combined and solvent removed in vacuo to afford the desired product as a pale yellow solid, 76.5 mg, 71.9%.

Step 2: Preparation of Title compound: 1-Benzyl-1H-pyrazole-4-carboxylic acid [5-(4-piperidin-1-ylmethyl-phenyl)-1H-pyrrolo[2,3-b]pyridin-3-yl]-amide 1-Benzyl-1H-pyrazole-4-carboxylic acid [5-(4-formyl-phenyl)-1H-pyrrolo[2,3-b]pyridin-3-yl]-amide (76.5 mg, 0.18 mmol) and piperidine (0.05 mL, 0.54 mmol) were stirred in THF (6 mL) at RT for 10 minutes. NaBH(OAc)$_3$ (190.8 mg, 0.90 mmol) was added and the reaction was stirred at RT 18 hours. The reaction mixture was quenched by the addition of saturated aqueous NaHCO$_3$ and extracted with EtOAc (2×30 mL). The combined organic extracts were washed with saturated aqueous sodium chloride, dried (MgSO$_4$) and concentrated in vacuo to afford a yellow gum. Crude material was purified by automated column chromatography, eluting with DCM to 16% MeOH/DCM (gradient). Fractions found to contain product were combined and solvent removed in vacuo to afford the title compound as a cream solid, 35.2 mg, 39.5%.

LC/MS: RT=1.90 Min (270 nm), m/z=491.5 [M+H]. Total run time 3.75 min (short pos/neg), HP1100.

$^1$H NMR (d$_6$ DMSO): δ 1.39-1.41 (m, 2H), 1.48-1.52 (m, 4H), 2.32-2.35 (m, 4H), 3.47 (s, 2H), 5.41 (s, 2H), 7.29-7.34 (m, 3H), 7.36-7.41 (m, 4H), 7.64 (d, 2H), 7.82 (d, 1H), 8.10 (s, 1H), 8.47 (s, 1H), 8.49 (d, 1H), 8.53 (d, 1H), 9.90 (s, 1H), 11.49 (d, 1H)

Example 35: 1-Benzyl-1H-pyrazole-4-carboxylic acid [5-(4-{[(2-methoxy-ethyl)-methyl-amino]-methyl}-phenyl)-1H-pyrrolo[2,3-b]pyridin-3-yl]-amide

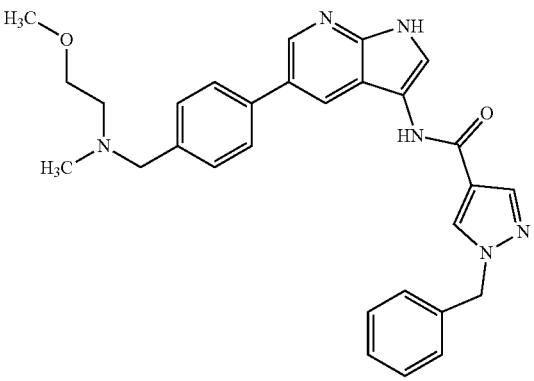 [SMILES: COCCN(C)Cc1ccc(-c2cnc3[nH]cc(NC(=O)c4cnn(Cc5ccccc5)c4)c3c2)cc1]

The title compound was prepared as described in Example 34, Step 1 and the following change to the described protocol for Step 2.

Step 2: 1-Benzyl-1H-pyrazole-4-carboxylic acid [5-(4-{[(2-methoxy-ethyl)-methyl-amino]-methyl}-phenyl)-1H-pyrrolo[2,3-b]pyridin-3-yl]-amide 1-Benzyl-1H-pyrazole-4-carboxylic acid [5-(4-formyl-phenyl)-1H-pyrrolo[2,3-b]pyridin-3-yl]-amide (50 mg, 0.12 mmol) was dissolved in DMF (5 mL) at rtp. To this was added (2-methoxy-ethyl)-methyl-amine (158.6 mg, 1.78 mmol) and AcOH (0.050 mL). The solution was then evacuated and backfilled with N2. 10% Palladium on charcoal (25.3 mg) was added then the reaction was evacuated and backfilled with N2 once more, then evacuated and backfilled with H$_2$. The reaction was then stirred under H$_2$ at 45° C. for 16 hours. To the reaction mixture was added a further 15 eq of amine and 50 uL of AcOH and the reaction was heated at 45° C. under H$_2$ for a further 24 hours. The catalyst was separated via filtration and the filter cake washed with a further portion of DMF (1 mL). The filtrate was concentrated in vacuo and the residue purified by preparative HPLC first at pH4 and then pH9 to furnish the title compound, 7.9 mg, 13.5% as a brown solid.

LC/MS: RT=1.91 Min (254 nm), m/z=495 [M+H]. Total run time 3.75 min (short pos/neg), HP1100.

$^1$H NMR (d$_6$ DMSO): δ 2.19 (s, 3H), 2.54 (t, 2H), 3.24 (s, 3H), 3.47 (t, 2H), 3.55 (s, 2H), 5.41 (s, 2H), 7.27-7.35 (m, 7H), 7.66 (m, 2H), 7.82 (d, 1H), 8.10 (d, 1H), 8.47 (s, 1H), 8.50 (d, 1H), 8.53 (d, 1H), 9.91 (s, 1H), 11.49 (br d, 1H)

Example 36: 1-Benzyl-1H-pyrazole-4-carboxylic acid [5-(4-pyrrolidin-1-ylmethyl-phenyl)-1H-pyrrolo[2,3-b]pyridin-3-yl]-amide

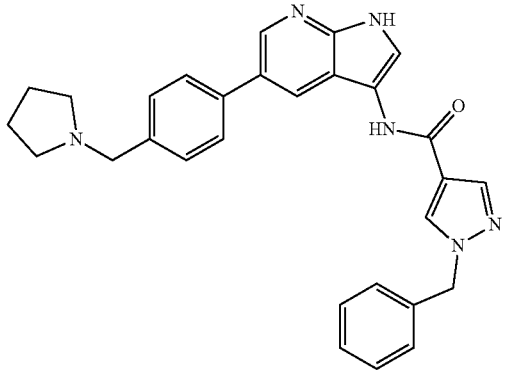 [SMILES: O=C(Nc1c[nH]c2ncc(-c3ccc(CN4CCCC4)cc3)cc12)c1cnn(Cc2ccccc2)c1]

The title compound was prepared as described in Example 34, substituting pyrrolidine (25.6 mg, 0.36 mmol) for piperidine in Step 2. It was isolated as a formate salt, 21 mg, 37.1%, following purification by preparative HPLC at pH 4.

LC/MS: RT=1.87 Min (270 nm), m/z=477 [M+H]. Total run time 3.75 min (short pos/neg), HP1100.

$^1$H NMR (d$_6$ DMSO): δ 1.69-1.76 (m, 4H), 5.41 (s, 2H), 7.28-7.45 (m, 7H), 7.65-7.68 (m, 2H), 7.82 (d, 1H), 8.10 (s, 1H), 8.23 (s, 1H), 8.47 (s, 1H), 8.49-8.51 (m, 1H), 8.53-8.55 (m, 1H), 9.92 (s, 1H), 11.49 (br d, 1H) 6 protons not seen

Example 37: 1-Benzyl-1H-pyrazole-4-carboxylic acid {5-[4-(4-fluoro-piperidin-1-ylmethyl)-phenyl]-1H-pyrrolo[2,3-b]pyridin-3-yl}-amide

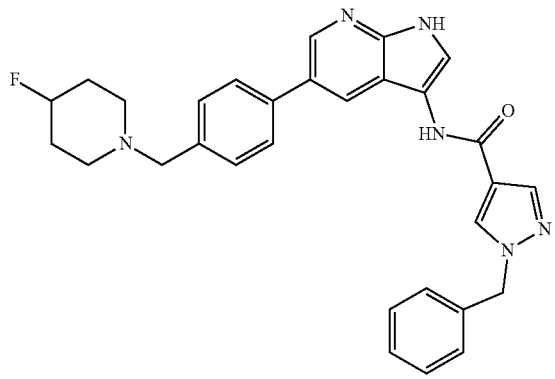 [SMILES: O=C(Nc1c[nH]c2ncc(-c3ccc(CN4CCC(F)CC4)cc3)cc12)c1cnn(Cc2ccccc2)c1]

The title compound was prepared as described in Example 34, substituting 4-fluoro-piperidine hydrochloride (99.4 mg, 0.71 mmol) for piperidine in Step 2. It was isolated as a white solid, 21 mg, 34%, following purification by automated column chromatography eluting with DCM to 8% MeOH/DCM (gradient) and saturation with acetonitrile.

LC/MS: RT=1.93 Min (270 nm), m/z=509 [M+H]. Total run time 3.75 min (short pos), HP1100.

$^1$H NMR (d$_6$ DMSO): δ 1.67-1.92 (m, 4H), 2.32 (m, 2H), 2.52 (m, 2H), 3.52 (s, 2H), 4.61-4.76 (m, 1H), 5.41 (s, 2H), 7.29-7.42 (m, 7H), 7.66 (m, 2H), 7.82 (s, 1H), 8.10 (s, 1H), 8.47-8.53 (m, 3H), 9.90 (s, 1H), 11.49 (br s, 1H)

Example 38: 1-Benzyl-1H-pyrazole-4-carboxylic acid [5-(4-dimethylaminomethyl-phenyl)-1H-pyrrolo[2,3-b]pyridin-3-yl]-amide

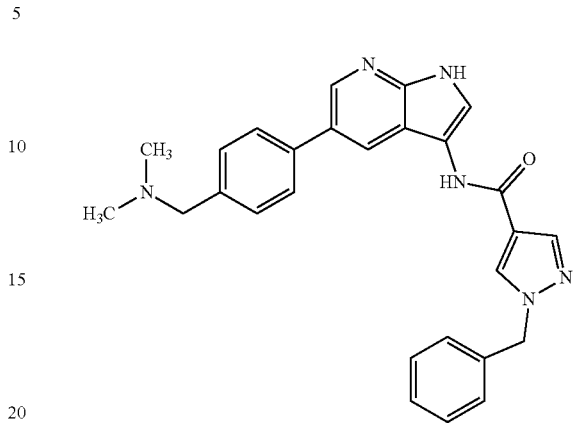

The title compound was prepared as described in Example 35, substituting dimethylamine solution, 2.0M in THF (1.07 mL, 2.14 mmol) for (2-methoxy-ethyl)-methyl-amine in Step 2. It was isolated as a yellow solid, containing 0.5 equivalents of formate salt, 4.4 mg, 13.7%, following purification by preparative HPLC at pH 9.

LC/MS: RT=1.84 Min (254 nm), m/z=451 [M+H]. Total run time 3.75 min (short pos/neg), HP1100.

$^1$H NMR (d$_6$ DMSO): δ 2.18 (s, 6H), 3.45 (s, 2H), 5.41 (s, 2H), 7.28-7.42 (m, 7H), 7.67 (m, 2H), 7.82 (d, 1H), 8.10 (d, 1H), 8.22 (s, 0.5H—formate), 8.47 (s, 1H), 8.50 (d, 1H), 8.54 (d, 1H), 9.91 (s, 1H), 11.49 (br d, 1H)

Example 39: 1-Benzyl-1H-pyrazole-4-carboxylic acid {5-[4-(3-fluoro-piperidin-1-ylmethyl)-phenyl]-1H-pyrrolo[2,3-b]pyridin-3-yl}-amide

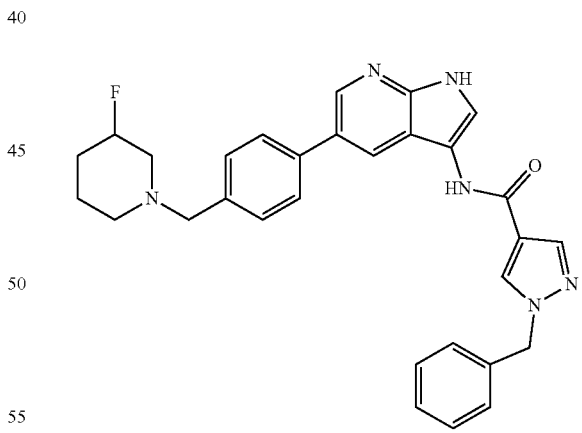

The title compound was prepared as described in Example 34, substituting 3-fluoro-piperidine hydrochloride (99.4 mg, 0.71 mmol) for piperidine in Step 2. It was isolated as a white solid, 17 mg, 28%, following purification by automated column chromatography eluting with DCM to 10% MeOH/DCM (gradient) and saturation with acetonitrile.

LC/MS: RT=1.91 Min (270 nm), m/z=509 [M+H]. Total run time 3.75 min (short pos), HP1100.

$^1$H NMR (d$_6$ DMSO): δ 1.44-1.56 (m, 2H), 1.68-1.87 (m, 2H), 2.24-2.44 (m, 2H), 2.66-2.75 (m, 2H), 3.56 (s, 2H), 4.55-4.71 (m, 1H), 5.41 (s, 2H), 7.29-7.42 (m, 7H), 7.66 (m, 2H), 7.82 (s, 1H), 8.10 (s, 1H), 8.47-8.53 (m, 3H), 9.90 (s, 1H), 11.49 (br s, 1H)

Example 40: 1-Benzyl-1H-pyrazole-4-carboxylic acid [5-(4-methylaminomethyl-phenyl)-1H-pyrrolo[2,3-b]pyridin-3-yl]-amide

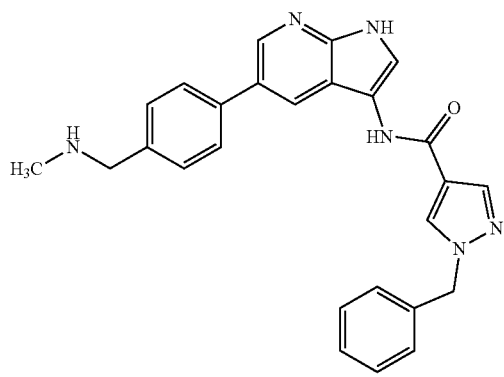 [SMILES: CNCc1ccc(-c2cnc3[nH]cc(NC(=O)c4cnn(Cc5ccccc5)c4)c3c2)cc1]

The title compound was prepared as described in Example 35, substituting methylamine solution, 2.0M in THF (1.07 mL, 2.14 mmol) for (2-methoxy-ethyl)-methyl-amine in Step 2. It was isolated as a pink solid, 4 mg, 12.9%, following purification by preparative HPLC at pH 4.

LC/MS: RT=1.83 Min (254 nm), m/z=437 [M+H]. Total run time 3.75 min (short pos/neg), HP1100.

$^1$H NMR (d$_6$ DMSO): δ 2.37 (s, 3H), 3.83 (s, 2H), 5.41 (s, 2H), 7.28-7.41 (m, 5H), 7.48 (m, 2H), 7.69 (m, 2H), 7.82 (d, 1H), 8.10 (s, 1H), 8.36 (s, 1H), 8.49 (s, 1H), 8.52 (d, 1H), 8.55 (d, 1H), 9.96 (s, 1H), 11.52 (br d, 1H)

Example 41: 1-Benzyl-1H-pyrazole-4-carboxylic acid [5-(4-morpholin-4-ylmethyl-phenyl)-1H-pyrrolo[2,3-b]pyridin-3-yl]-amide

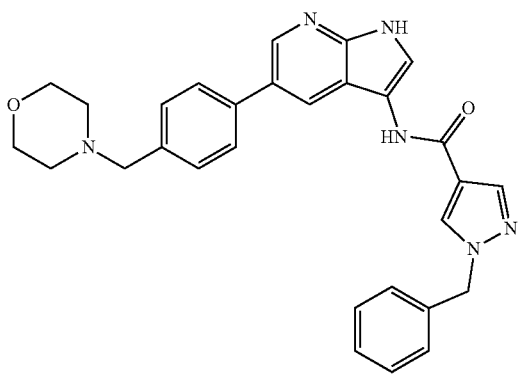 [SMILES: O=C(Nc1c[nH]c2ncc(-c3ccc(CN4CCOCC4)cc3)cc12)c1cnn(Cc2ccccc2)c1]

The title compound was prepared as described in Example 34, substituting morpholine (51.7 mg, 0.59 mmol) for piperidine in Step 2 It was isolated as an off white solid, 28.4 mg, 48.6%, following purification by column chromatography eluting with DCM—5% MeOH/DCM (gradient) and preparative HPLC at pH4.

LC/MS: RT=1.86 Min (254 nm), m/z=493 [M+H]. Total run time 3.75 min (short pos/neg), HP1100.

$^1$H NMR (d$_6$ DMSO): δ 2.38 (m, 4H), 3.51 (s, 2H), 3.59 (m, 4H), 5.41 (s, 2H), 7.28-7.45 (m, 7H), 7.67 (m, 2H), 7.81 (d, 1H), 8.09 (s, 1H), 8.47 (s, 1H), 8.49 (d, 1H), 8.53 (d, 1H), 9.91 (s, 1H), 11.49 (br d, 1H)

Example 42: 1-Benzyl-1H-pyrazole-4-carboxylic acid {5-[4-(3,3-difluoro-pyrrolidin-1-ylmethyl)-phenyl]-1H-pyrrolo[2,3-b]pyridin-3-yl}-amide

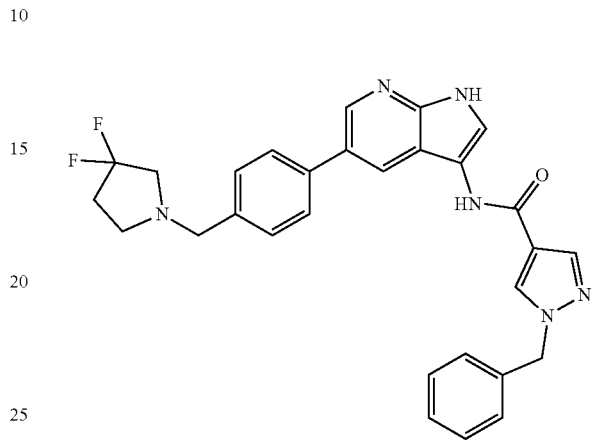

The title compound was prepared as described in Example 34, substituting 3,3-difluoropyrrolidine hydrochloride (102.2 mg, 0.71 mmol) for piperidine in Step 2. It was isolated as a white solid, 22 mg, 36.2%, following purification by automated column chromatography eluting with DCM to 10% MeOH/DCM (gradient) and trituration with acetonitrile.

LC/MS: RT=2.17 Min (270 nm), m/z=513 [M+H]. Total run time 3.75 min (short pos), HP1100.

$^1$H NMR (d$_6$ DMSO): δ 2.26 (m, 2H), 2.72 (t, 2H), 2.88 (t, 2H), 3.67 (s, 2H), 5.41 (s, 2H), 7.29-7.44 (m, 7H), 7.69 (m, 2H), 7.82 (s, 1H), 8.10 (s, 1H), 8.47-8.53 (m, 3H), 9.90 (s, 1H), 11.50 (br s, 1H)

Example 43: 1-Benzyl-1H-pyrazole-4-carboxylic acid [5-(3-dimethylaminomethyl-phenyl)-1H-pyrrolo[2,3-b]pyridin-3-yl]-amide

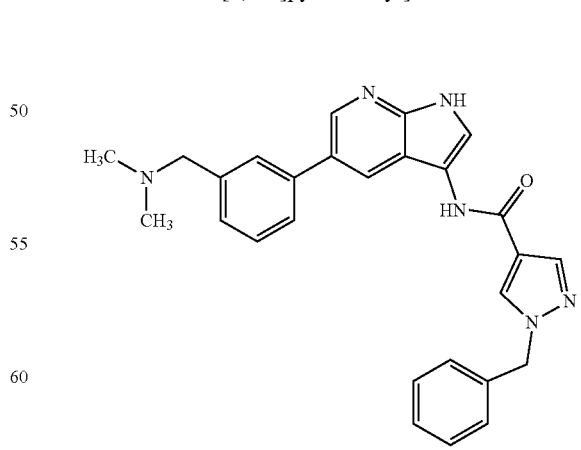

The title compound was prepared according to the route outlined in Scheme 4. The title compound was prepared from Example 1.

Step 1: Preparation of 1-Benzyl-1H-pyrazole-4-carboxylic acid [5-bromo-1-(toluene-4-sulfonyl)-1H-pyrrolo[2,3-b]pyridin-3-yl]-amide To a solution of 1-benzyl-1H-pyrazole-4-carboxylic acid (5-bromo-1H-pyrrolo[2,3-b]pyridin-3-yl)-amide 93.5 g, 8.83 mmol) in DCM (75 ml) was added tetrabutylammonium hydrogen sulphate 0.45 g, 1.32 mmol), aqueous sodium hydroxide solution (50%, w/v, 7 mL) and tosyl chloride (2.02 g, 10.6 mmol). The reaction mixture was stirred at RT for 4 hours and then diluted with DCM. It was washed with aqueous 1M HCl, saturated aqueous bicarbonate, saturated aqueous sodium chloride, dried (MgSO$_4$) and concentrated in vacuo. The residue was purified via automated column chromatography eluting with iso-hexane to 75% EtOAc/iso-hexane (gradient). This furnished the desired compound as a brown foam, 3.51 g, 61.4%.

Step 2: Preparation of 1-Benzyl-1H-pyrazole-4-carboxylic acid [5-(3-formyl-phenyl)-1-(toluene-4-sulfonyl)-1H-pyrrolo[2,3-b]pyridin-3-yl]-amide 1-Benzyl-1H-pyrazole-4-carboxylic acid [5-bromo-1-(toluene-4-sulfonyl)-1H-pyrrolo[2,3-b]pyridin-3-yl]-amide (595 mg, 1.08 mmol), 3-formylphenylboronic acid (195 mg, 1.3 mmol), K$_2$CO$_3$ (448 mg, 3.24 mmol) and Pd(dppf)Cl$_2$ (39.6 mg, 0.05 mmol) were combined in THF/H$_2$O (10 mL/1 mL) and thoroughly degassed. The reaction mixture was heated at 120° C. for 1 hour under microwave irradiation. The reaction was diluted with EtOAc, washed with H$_2$O, the aqueous was extracted again with EtOAc and the combined organics were washed with saturated aqueous sodium chloride, dried (MgSO$_4$) and solvent removed in vacuo to afford a brown gum. This crude material was purified by automated column chromatography, eluting with iso-hexane to 50% EtOAc/iso-hexane to EtOAc (gradient). Fractions found to contain pure material were combined and solvent removed in vacuo to afford the desired product as a yellow solid, 420 mg, 67.5%.

Step 3: Preparation of 1-benzyl-1H-pyrazole-4-carboxylic acid [5-(3-dimethylaminomethyl-phenyl)-1-(toluene-4-sulfonyl)-1H-pyrrolo[2,3-b]pyridin-3-yl]-amide To a solution of 1-benzyl-1H-pyrazole-4-carboxylic acid [5-(3-formyl-phenyl)-1-(toluene-4-sulfonyl)-1H-pyrrolo[2,3-b]pyridin-3-yl]-amide (100 mg, 0.17 mmol) in MeOH (1 mL) was added 4 Å molecular sieves followed by dimethylamine, 2.0M solution in THF (4 mL, 8 mmol) and the reaction stirred for 3 hours at RT. Sodium triacetoxyborohydride (72.1 mg, 0.34 mmol) was added and the reaction stirred 18 hours at RT. The inorganic material was separated via filtration and the filtrate was diluted with DCM. The solution was washed with aqueous saturated sodium bicarbonate solution, dried (MgSO$_4$) and concentrated in vacuo. The residue was purified using automated column chromatography eluting with DCM to 10% MeOH/DCM. Fractions containing pure compound were combined and concentrated in vacuo to give the desired compound as a colourless glass, 61 mg, 58.0%.

Step 4: Preparation of Title compound: 1-benzyl-1H-pyrazole-4-carboxylic acid [5-(3-dimethylaminomethyl-phenyl)-1H-pyrrolo[2,3-b]pyridin-3-yl]-amide 1-Benzyl-1H-pyrazole-4-carboxylic acid [5-(3-dimethylaminomethyl-phenyl)-1-(toluene-4-sulfonyl)-1H-pyrrolo[2,3-b]pyridin-3-yl]-amide (61 mg, 0.10 mmol) was dissolved in a mixture of THF (2 mL) and MeOH (1 mL) and potassium hydroxide (26.6 mg, 0.474 mmol) in the minimum volume of H$_2$O was added. After stirring at RT for 18 hours the reaction mixture was diluted with H$_2$O and stirring continued. After 1 hour the solids were separated via filtration and the filter cake was washed with H$_2$O prior to drying in vacuo at 40° C. This furnished the title compound as a yellow solid, 15 mg, 33.2%.

LC/MS: RT=0.99 Min (230 nm), m/z=451 [M+H]. Total run time 1.9 min (super short pos), HP1200.

$^1$H NMR (d$_6$ DMSO): δ 2.18 (s, 6H), 3.47 (s, 2H), 5.42 (s, 2H), 7.25-7.46 (m, 7H), 7.58-7.63 (m, 2H), 7.84 (s, 1H), 8.10 (s, 1H), 8.47 (s, 1H), 8.50-8.53 (m, 2H), 9.95 (br s, 1H), 11.50 (br s, 1H)

Example 44: 1-Benzyl-1H-pyrazole-4-carboxylic acid {5-[3-(3-fluoro-piperidin-1-ylmethyl)-phenyl]-1H-pyrrolo[2,3-b]pyridin-3-yl}-amide

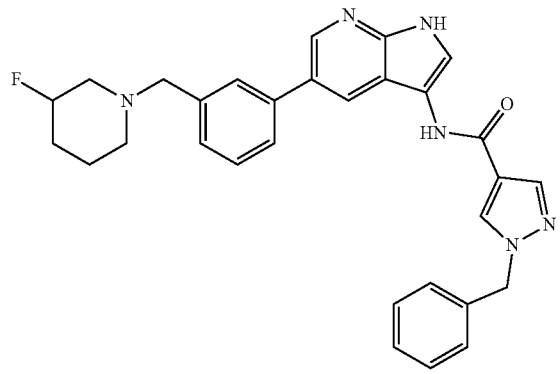 [SMILES: O=C(Nc1c[nH]c2ncc(-c3cccc(CN4CCCC(F)C4)c3)cc12)c1cnn(Cc2ccccc2)c1]

The title compound was prepared as described in Example 43, substituting 3-fluoropiperidine hydrochloride (47.5 mg, 0.34 mmol) for piperidine in Step 3. It was isolated as a yellow powder, 11.7 mg, 18.1%, following purification by preparative HPLC at pH9.

LC/MS: RT=1.04 Min (230 nm), m/z=509 [M+H]. Total run time 1.9 min (super short pos), HP1200.

$^1$H NMR (d$_6$ DMSO): δ 1.40-1.60 (m, 2H), 1.67-1.90 (m, 2H), 2.24-2.32 (m, 1H), 2.36-2.48 (m, 2H), 2.66-2.76 (m, 1H), 3.60 (s, 2H), 4.54-4.74 (m, 1H), 5.42 (s, 2H), 7.28-7.40 (m, 6H), 7.45 (dd, 1H), 7.58-7.62 (m, 2H), 7.84 (d, 1H), 8.10 (s, 1H), 8.47 (s, 1H), 8.50 (d, 1H), 8.52 (d, 1H), 9.96 (s, 1H), 11.51 (br d, 1H)

Example 45: 1-Benzyl-1H-pyrazole-4-carboxylic acid {5-[3-(3,3-difluoro-piperidin-1-ylmethyl)-phenyl]-1H-pyrrolo[2,3-b]pyridin-3-yl}-amide

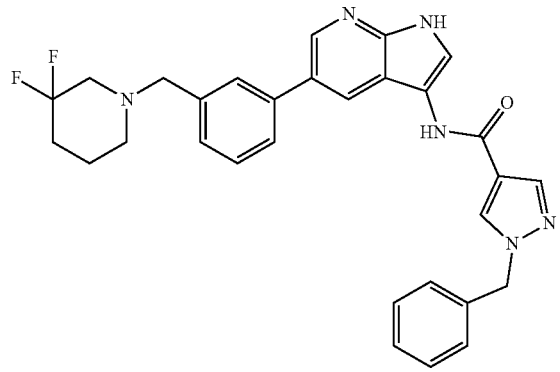 [SMILES: O=C(Nc1c[nH]c2ncc(-c3cccc(CN4CCCC(F)(F)C4)c3)cc12)c1cnn(Cc2ccccc2)c1]

The title compound was prepared as described in Example 43, substituting 3,3-difluoropiperidine hydrochloride (124 mg, 0.79 mmol) for piperidine and sodium cyanoborohydride (13.1 mg, 0.21 mmol) for sodium triacetoxyborohydride in Step 3.

Step 4: Preparation of Title compound: 1-Benzyl-1H-pyrazole-4-carboxylic acid {5-[3-(3,3-difluoro-piperidin-1-ylmethyl)-phenyl]-1H-pyrrolo[2,3-b]pyridin-3-yl}-amide 1-Benzyl-1H-pyrazole-4-carboxylic acid [5-[3-(3,3-difluoro-piperidin-1-ylmethyl)-phenyl]-1-(toluene-4-sulfonyl)-1H-pyrrolo[2,3-b]pyridin-3-yl]-amide (100 mg, 0.147 mmol), potassium carbonate (138 mg, 1 mmol) and MeOH (4 mL) were combined in a microwave vial and heated under microwave irradiation at 100° C. for 30 minutes. The reaction mixture was diluted with $H_2O$ and extracted with a mixture of DCM/IPA (3.1). The organics were washed with saturated aqueous sodium chloride, dried (MgSO4) and concentrated in vacuo. The residue was taken up in the minimum amount of MeOH and then $Et_2O$ was added until the solution started to go cloudy. This was left to stand for 1 hour then the crystals were filtered off and dried in vacuo at 40° C. to furnish the title compound as yellow crystals, 30.3 mg, 38.6%.

LC/MS: RT=1.17 Min (230 nm), m/z=527 [M+H]. Total run time 1.9 min (super short pos), HP1200.

$^1$H NMR (d$_6$ DMSO): δ 1.62-1.71 (m, 2H), 1.80-1.95 (m, 2H), 2.42-2.48 (m, 2H), 2.61-2.70 (m, 2H), 3.67 (s, 2H), 5.41 (s, 2H), 7.28-7.40 (m, 6H), 7.47 (dd, 1H), 7.59-7.63 (m, 2H), 7.83 (d, 1H), 8.10 (s, 1H), 8.47 (s, 1H), 8.49 (d, 1H), 8.52 (d, 1H), 9.94 (s, 1H), 11.52 (br d, 1H)

Example 46: 1-Benzyl-1H-pyrazole-4-carboxylic acid [5-(3-azetidin-1-ylmethyl-phenyl)-1H-Pyrrolo[2,3-b]pyridin-3-yl]-amide

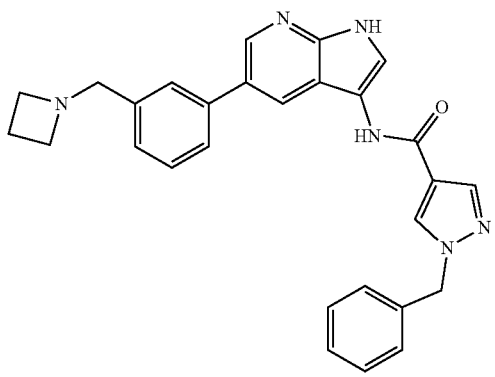 [SMILES: O=C(Nc1c[nH]c2ncc(-c3cccc(CN4CCC4)c3)cc12)c1cnn(Cc2ccccc2)c1]

The title compound was prepared as described in Example 45, substituting azetidine (38.7 mg, 0.68 mmol) for piperidine in Step 3. In Step 4 the product precipitated after diluting with $H_2O$ and was collected via filtration, washed with $H_2O$, $Et_2O$ and dried in vacuo at 40° C. to furnish the title compound as an off white solid, 26.7 mg, 25.6%.

LC/MS: RT=1.00 Min (230 nm), m/z=463.2 [M+H]. Total run time 1.9 min (super short pos), HP1200.

$^1$H NMR (d$_6$ DMSO): δ 1.94-2.02 (m, 2H), 3.12-3.18 (m, 4H), 3.60 (s, 2H), 5.42 (s, 2H), 7.22-7.46 (m, 7H), 7.54-7.60 (m, 2H), 7.83 (s, 1H), 8.10 (s, 1H), 8.46-8.53 (m, 3H), 9.8-10.2 (br s, 1H), 11-12 (br s, 1H)

Example 47: 1-Benzyl-1H-pyrazole-4-carboxylic acid {5-[3-(3,3-difluoro-azetidin-1-ylmethyl)-phenyl]-1H-pyrrolo[2,3-b]pyridin-3-yl}-amide

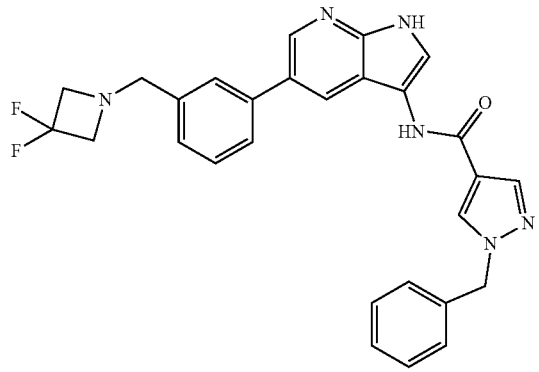 [SMILES: O=C(Nc1c[nH]c2ncc(-c3cccc(CN4CC(F)(F)C4)c3)cc12)c1cnn(Cc2ccccc2)c1]

The title compound was prepared as described in Example 45, substituting 3,3-difluoroazetidine hydrochloride (114 mg, 0.88 mmol) for piperidine and sodium cyanoborohydride (13.1 mg, 0.21 mmol) for sodium triacetoxyborohydride in Step 3. In Step 4 the product precipitated after diluting with $H_2O$ and was collected via filtration, washed with $H_2O$, $Et_2O$ and dried in vacuo at 40° C. to furnish the title compound as a cream powder, 23.4 mg, 38.8%.

LC/MS: RT=1.15 Min (230 nm), m/z=499.2 [M+H]. Total run time 1.9 min (super short pos), HP1200.

$^1$H NMR (d$_6$ DMSO): δ 3.64 (t, 4H), 3.81 (s, 2H), 5.42 (s, 2H), 7.28-7.41 (m, 6H), 7.45 (dd, 1H), 7.59-7.65 (m, 2H), 7.84 (s, 1H), 8.10 (s, 1H), 8.47 (s, 1H), 8.50 (d, 1H), 8.53 (d, 1H), 9.95 (br s, 1H), 11.51 (br s, 1H)

Example 48: 1-Benzyl-1H-pyrazole-4-carboxylic acid [5-(5-pyrrolidin-1-ylmethyl-thiophen-2-yl)-1H-pyrrolo[2,3-b]pyridin-3-yl]-amide

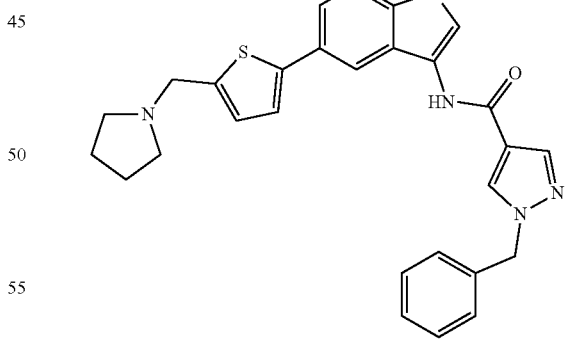

The title compound was prepared as described in Example 43, substituting 5-formyl-2-thiopheneboronic acid 67.1 mg, 0.43 mmol) for 3-formylphenylboronic acid, 2M aqueous sodium carbonate 76.3 mg, 0.72 mmol) for $K_2CO_3$, tetrakis (19.6 mg, 0.017 mmol) for Pd(dppf)Cl$_2$ and 1,4-dioxane/THF (4 mL:2 mL) for THF/$H_2O$ (10:1) in Step 2. The reaction mixture was heated at 150° C. for 2 hours under microwave irradiation. The reaction was diluted with 3:1 DCM/IPA, washed with saturated aqueous sodium chloride, dried (MgSO$_4$) and concentrated in vacuo. The residue was dissolved in the minimum amount of DCM and Et$_2$O was added to precipitate the desired, deprotected, Suzuki product, 1-benzyl-1H-pyrazole-4-carboxylic acid [5-(5-formyl-thiophen-2-yl)-1H-pyrrolo[2,3-b]pyridin-3-yl]-amide, 68 mgs, 43.8%. In Step 3 pyrrolidine (45.3 mg, 0.64 mmol) was substituted for piperidine and sodium cyanoborohydride (15 mg, 0.24 mmol) for sodium triacetoxyborohydride. The title compound was isolated as a white solid, 5 mg, 6.5%, following purification by automated column chromatography eluting with DCM to 20% MeOH/DCM (gradient), preparative HPLC at pH4 and finally trituration with Et$_2$O LC/MS: RT=0.94 Min (230 nm), m/z=483 [M+H]. Total run time 1.9 min (super short pos), HP1200.

$^1$H NMR (d$_6$ DMSO): δ 1.68-1.76 (m, 4H), 3.79 (s, 2H), 5.42 (s, 2H), 6.95 (d, 1H), 7.27-7.41 (m, 6H), 7.82 (s, 1H), 8.10 (s, 1H), 8.44 (d, 1H), 8.48 (s, 1H), 8.55 (d, 1H), 9.94 (br s, 1H), 11.53 (br s, 1H) 4 protons not seen Example 49: 1-Benzyl-1H-pyrazole-4-carboxylic acid [5-(5-pyrrolidin-1-ylmethyl-thiophen-3-yl)-1H-pyrrolo[2,3-b]pyridin-3-yl]-amide

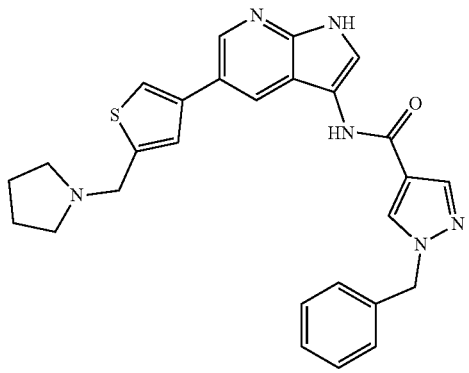 [SMILES: O=C(Nc1c[nH]c2ncc(-c3csc(CN4CCCC4)c3)cc12)c1cnn(Cc2ccccc2)c1]

The title compound was prepared as described in Example 43, substituting 5-formyl-3-thiopheneboronic acid (67.1 mg, 0.43 mmol) for 3-formylphenylboronic acid, 2M aqueous sodium carbonate (76.3 mg, 0.72 mmol) for K$_2$CO$_3$, tetrakis (19.6 mg, 0017 mmol) for Pd(dppf)Cl$_2$ and 1,4-dioxane (4 mL) for THF/H$_2$O (10:1) in Step 2. The reaction mixture was heated at 150° C. for 20 minutes under microwave irradiation. The reaction was diluted with DCM washed with saturated aqueous sodium chloride, dried (MgSO$_4$) and concentrated in vacuo.

The residue was dissolved in the minimum amount of DCM and Et$_2$O was added to precipitate the desired Suzuki product, 142 mgs, 64.9% as a brown powder. In Step 3 pyrrolidine (34.2 mg, 0.48 mmol) was substituted for piperidine and sodium cyanoborohydride (11.3 mg, 0.18 mmol) for sodium triacetoxyborohydride. In Step 4 potassium carbonate (83.2 mg, 0.6 mmol) and MeOH (4 mL) were combined in a microwave vial and heated under microwave irradiation at 100° C. for 30 minutes. The reaction mixture was diluted with H$_2$O and the precipitate was collected via filtration, washed with H$_2$O, Et$_2$O and dried in vacuo at 40° C. to furnish the title compound as a cream powder, 12.8 mg, 22%.

LC/MS: RT=0.94 Min (230 nm), m/z=483 [M+H]. Total run time 1.9 min (super short pos), HP1200.

$^1$H NMR (d$_6$ DMSO): δ 1.68-1.76 (m, 4H), 3.82 (s, 2H), 5.42 (s, 2H), 7.28-7.42 (m, 6H), 7.68 (d, 1H), 7.78 (s, 1H), 8.10 (s, 1H), 8.46 (d, 1H), 8.48 (s, 1H), 8.59 (d, 1H), 9.83 (br s, 1H), 11-12 (br s, 1H) 4 protons not seen Example 50: 1-Benzyl-1H-pyrazole-4-carboxylic acid {5-[5-(3,3-difluoro-azetidin-1-ylmethyl)-thiophen-3-yl]-1H-pyrrolo[2,3-b]pyridin-3-yl}-amide

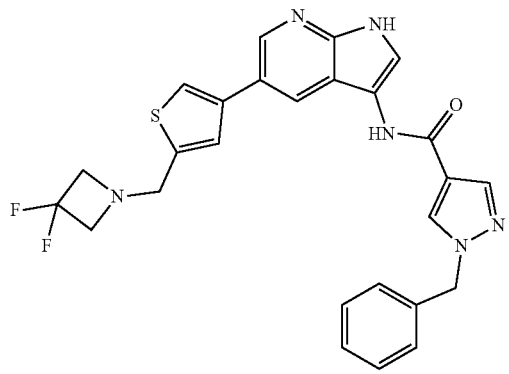 [SMILES: O=C(Nc1c[nH]c2ncc(-c3csc(CN4CC(F)(F)C4)c3)cc12)c1cnn(Cc2ccccc2)c1]

The title compound was prepared as described in Example 49, substituting 3,3-difluoro-azetidine hydrochloride (94.5 mg, 0.73 mmol) for pyrrolidine in Step 3.

It was isolated as a cream powder, 27.5 mg, 53.4%, following the same procedure described in Step 4.

LC/MS: RT=1.19 Min (230 nm), m/z=505 [M+H]. Total run time 1.9 min (super short pos), HP1200.

$^1$H NMR (d$_6$ DMSO): δ 3.67 (t, 4H), 3.96 (s, 2H), 5.42 (s, 2H), 7.28-7.41 (m, 5H), 7.44-7.46 (m, 1H), 7.72 (d, 1H), 7.78 (d, 1H), 8.10 (d, 1H), 8.45 (d, 1H), 8.47 (s, 1H), 8.59 (d, 1H), 9.88 (br s, 1H), 11.47 (br d, 1H)

Example 51: 1-Benzyl-1H-pyrazole-4-carboxylic acid [5-(3-pyrrolidin-1-ylmethyl-phenyl)-1H-pyrrolo[2,3-b]pyridin-3-yl]-amide

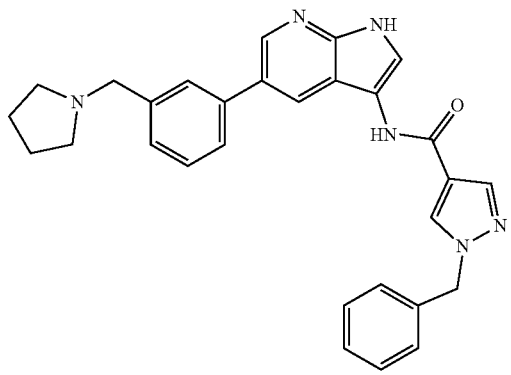 [SMILES: O=C(Nc1c[nH]c2ncc(-c3cccc(CN4CCCC4)c3)cc12)c1cnn(Cc2ccccc2)c1]

The title compound was prepared as described in Example 43, substituting pyrrolidine (30 mg, 0.45 mmol) for dimethylamine, 2.0M solution in THF in Step 3. In Step 4 potassium carbonate (71.9 mg, 0.52 mmol) and MeOH (3 mL) were combined in a microwave vial and heated under microwave irradiation at 100° C. for 30 minutes. The reaction mixture was concentrated to half volume in vacuo. H$_2$O was added to the residue and the precipitate was collected via filtration, washed with H$_2$O, Et$_2$O and dried in vacuo at 40° C. to furnish the title compound as a cream powder, 38 mg, 76.8%.

LC/MS: RT=1.04 Min (230 nm), m/z=477 [M+H]. Total run time 1.9 min (super short pos), HP1200.

¹H NMR (d₆ DMSO): δ 1.66-1.74 (m, 4H), 2.42-2.50 (m, 4H), 3.65 (s, 2H), 5.42 (s, 2H), 7.28-7.45 (m, 7H), 7.56-7.64 (m, 2H), 7.83 (s, 1H), 8.10 (s, 1H), 8.47 (s, 1H), 8.49-8.52 (m, 2H), 9.8-10.12 (br s, 1H), 11.12 (br s, 1H)

Example 52: 1-Benzyl-1H-pyrazole-4-carboxylic acid [4-((R)-3-amino-piperidin-1-yl)-5-fluoro-1H-pyrrolo[2,3-b]pyridin-3-yl]-amide

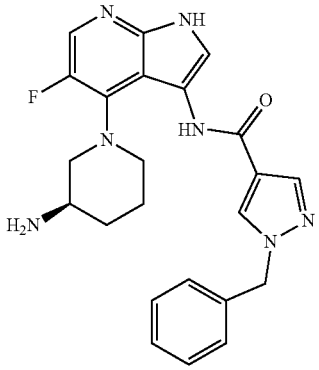 [SMILES: N[C@@H]1CCCN(c2c(F)cnc3[nH]cc(NC(=O)c4cnn(Cc5ccccc5)c4)c23)C1]

The title compound was prepared according to an analogous route to that outlined in Scheme 2.

The title compound was prepared as described in Example 6, substituting N-fluorobis(phenylsulphonyl)amine (1.08 g, 3.42 mmol) for carbon tetrabromide in Step 3, and the desired intermediate was isolated as a white solid, 134 mg, 63.4%. The crude material from Step 8 was purified by automated column chromatography, eluting with DCM—16% MeOH/DCM (gradient) and then preparative HPLC at pH 4. The title compound was isolated as a white solid, 34.3 mg, 46.6%.

LC/MS: RT=1.70 Min (270 nm), m/z=434.5 [M+H]. Total run time 3.75 min (short pos/neg), HP1100.

¹H NMR (d₆ DMSO): δ 1.33-1.38 (m, 2H), 1.60-1.63 (m, 1H), 1.74-1.76 (m, 1H), 2.98-3.14 (m, 4H), 3.46-3.48 (m, 1H), 5.41 (s, 2H), 7.24-7.26 (m, 2H), 7.31-7.39 (m, 3H), 7.52 (s, 1H), 8.07 (s, 1H), 8.09 (d, 1H), 8.48 (s, 1H), 9.70 (s, 1H), 11.70 (br s, 1H) 2 protons not seen Example 53: 1-Benzyl-1H-pyrazole-4-carboxylic acid [4-((R)-3-amino-piperidin-1-yl)-5-phenyl-1H-pyrrolo[2,3-b]pyridin-3-yl]-amide

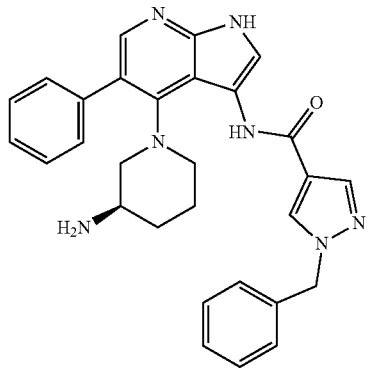 [SMILES: N[C@@H]1CCCN(c2c(-c3ccccc3)cnc3[nH]cc(NC(=O)c4cnn(Cc5ccccc5)c4)c23)C1]

The title compound was prepared according to the route outlined in Scheme 3.

The title compound was prepared from 1-benzyl-1H-pyrazole-4-carboxylic acid (5-bromo-4-fluoro-1H-pyrrolo[2,3-b]pyridin-3-yl)-amide, the product of Step 7 in Example 6.

Step 1: Preparation of ((R)-1-{3-[(1-Benzyl-1H-pyrazole-4-carbonyl)-amino]-5-bromo-1H-pyrrolo[2,3-b]pyridin-4-yl}-piperidin-3-yl)-carbamic acid tert-butyl ester 1-Benzyl-1H-pyrazole-4-carboxylic acid (5-bromo-4-fluoro-1H-pyrrolo[2,3-b]pyridin-3-yl)-amide (0.445 g, 1.07 mmol). (R)-piperidin-3-yl-carbamic acid tert-butyl ester (1.08 g, 5.37 mmol) and n-butanol (15 mL) were combined in a microwave vial. The contents were heated at 160° C. for 6 hours under microwave irradiation and then the reaction mixture was diluted with EtOAc. The solution was washed with H₂O, saturated aqueous sodium chloride, dried (MgSO₄) and concentrated in vacuo to afford a brown gum. This crude material was purified by automated column chromatography, eluting with iso-hexane-50% EtOAc/iso-hexane-EtOAc (gradient). Fractions found to contain pure product were combined and concentrated in vacuo to afford the desired compound as a yellow powder, 443.2 mg, 69.4%.

Step 2: Preparation of Title compound: 1-Benzyl-1H-pyrazole-4-carboxylic acid [4-((R)-3-amino-piperidin-1-yl)-5-phenyl-1H-pyrrolo[2,3-b]pyridin-3-yl]-amide Phenylboronic acid (17.9 mg, 0.15 mmol), ((R)-1-{3-[(1-Benzyl-1H-pyrazole-4-carbonyl)-amino]-5-bromo-1H-pyrrolo[2,3-b]pyridin-4-yl}-piperidin-3-yl)-carbamic acid tert-butyl ester (48.4 mg, 0.08 mmol), K₂CO₃ (34.6 mg, 0.25 mmol), Pd(dppf)Cl₂ (8.0 mg, 0.01 mmol) and THF/H₂O (4.5 mL:0.5 mL) were combined in a microwave vial and thoroughly degassed. The reaction mixture was heated at 100° C. for 1 hour under microwave irradiation and then it was diluted with EtOAc. The organic layer was separated and the aqueous extracted with another portion of EtOAc. The combined organics were washed with H₂O, saturated aqueous sodium chloride, dried (MgSO₄) and solvent removed in vacuo to afford a brown gum. This material was taken up in DCM (10 mL) and cooled in an ice bath followed by drop wise addition of TFA (0.03 mL, 0.4 mmol). Stirring was continued for 4 hours at RT and the solvents removed in vacuo. The crude material was purified by automated column chromatography, eluting with DCM—15% MeOH/DCM. Fractions found to contain pure material were combined and solvent removed in vacuo to afford the title compound as a solid, 22 mg, 55%.

LC/MS: RT=1.82 Min (270 nm), m/z=492 [M+H]. Total run time 3.75 min (short pos/neg), HP1100.

¹H NMR (d₆ DMSO): δ ☐ 1.35-1.45 (m, 2H), 1.56-1.67 (m, 1H), 2.25-2.37 (m, 1H), 2.76-3.04 (m, 3H), 3.13-3.22 (m, 1H), 5.40 (s, 2H), 7.18-7.82 (m, 11H), 7.89 (br s, 1H), 8.05 (s, 1H), 8.42 (s, 1H), 9.53 (s, 1H), 11.74 (s, 1H)

Example 54: 1-Benzyl-1H-pyrazole-4-carboxylic acid [4-((R)-3-amino-piperidin-1-yl)-5-cyano-1H-pyrrolo[2,3-b]pyridin-3-yl]-amide

Example 55: 1-Benzyl-1H-pyrazole-4-carboxylic acid {5-[3-(2-morpholin-4-yl-ethoxy)-phenyl]-1H-pyrrolo[2,3-b]pyridin-3-yl}-amide

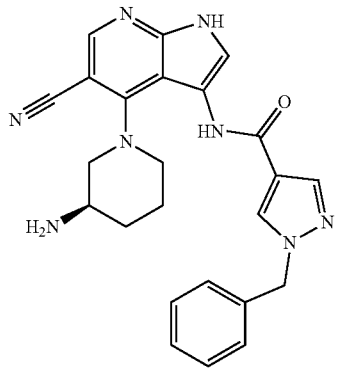 [SMILES: N#Cc1cnc2[nH]cc(NC(=O)c3cnn(Cc4ccccc4)c3)c2c1N1CCC[C@@H](N)C1]

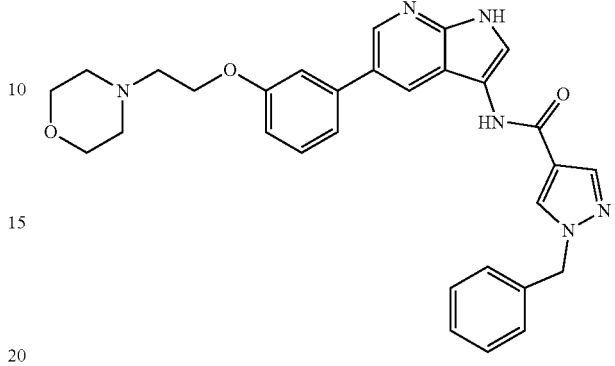

The title compound was prepared from ((R)-1-{3-[(1-benzyl-1H-pyrazole-4-carbonyl)-amino]-5-bromo-1H-pyrrolo[2,3-b]pyridin-4-yl}-piperidin-3-yl)-carbamic acid tert-butyl ester, the product of Step 1, Example 53.

((R)-1-{3-[(1-benzyl-1H-pyrazole-4-carbonyl)-amino]-5-bromo-1H-pyrrolo[2,3-b]pyridin-4-yl}-piperidin-3-yl)-carbamic acid tert-butyl ester (21 mg, 0.04 mmol), dicyanozinc (7.5 mg, 0.06 mmol), Pd(PPh$_3$)$_4$ (6.1 mg, 0.01 mmol) and DMF (5 mL) were combined in a microwave vial and degassed. The contents were heated under microwave irradiation at 12° C. for 1 hour. A further portion of dicyano zinc (2.1 mg, 0.018 mmol) and Pd(PPh$_3$)$_4$ (2.0 mg) were added and degassed. The contents were heated under microwave irradiation at 120° C. for 2 hours. The reaction mixture was partitioned between EtOAc and H$_2$O, then the organic layer was separated and the aqueous extracted with another portion of EtOAc. The combined organics were washed with H$_2$O, saturated aqueous sodium chloride, dried (MgSO$_4$) and solvent removed in vacuo to afford a brown gum. The crude product was purified by automated column chromatography eluting with iso-hexane—50% EtOAc/iso-hexane-EtOAc (gradient). Fractions found to contain pure material were combined and solvent removed in vacuo to afford ((R)-1-{3-[(1-benzyl-1H-pyrazole-4-carbonyl)-amino]-5-cyano-1H-pyrrolo[2,3-b]pyridin-4-yl}-piperidin-3-yl)-carbamic acid tert-butyl ester. This material was taken up in hydrochloric acid solution, 1.25 M in MeOH (5 mL) and irradiated in a microwave for 1 hour at 80° C. The volatiles were removed in vacuo and the residue was taken up in the minimum volume of MeOH and loaded onto a SCX2 ion exchange column that had been primed with MeOH. The column was washed with DCM, MeOH and the title compound was eluted using ammonia solution, 3.5M in MeOH. This solution was concentrated in vacuo to afford the title compound as a white solid, 3 mg, 19.3%.

LC/MS: RT=1.67 Min (270 nm), m/z=441 [M+H]. Total run time 3.75 min (short pos/neg), HP1100.

$^1$H NMR (d$_4$ MeOH): δ 1.35-1.98 (m, 4H), 3.18-3.26 (m, 1H), 3.47-3.56 (m, 1H), 3.84-3.90 (m, 1H), 5.41 (s, 2H), 7.24-7.40 (m, 5H), 7.43 (s, 1H), 8.08 (s, 1H), 8.26 (s, 1H), 8.36 (s, 1H) 6 protons not seen The title compound was prepared according to the route outlined in Scheme 5. The title compound was prepared from 1-benzyl-1H-pyrazole-4-carboxylic acid [5-bromo-1-(toluene-4-sulfonyl)-1H-pyrrolo[2,3-b]pyridin-3-yl]-amide, the product of Step 1, Example 43.

Step 1: Preparation of 1-Benzyl-1H-pyrazole-4-carboxylic acid [5-(4,4,5,5-tetramethyl-[1,3,2]dioxaborolan-2-yl)-1-(toluene-4-sulfonyl)-1H-pyrrolo[2,3-b]pyridin-3-yl]-amide 3-(4,4,5,5-tetramethyl-1,3,2-dioxaborolan-2-yl)phenol (408 mg, 1.85 mmol), 1-benzyl-1H-pyrazole-4-carboxylic acid [5-bromo-1-(toluene-4-sulfonyl)-1H-pyrrolo[2,3-b] pyridin-3-yl]-amide (850 mg, 1.54 mmol), K$_2$CO$_3$ (640 mg, 4.63 mmol), Pd(dppf)Cl$_2$ (56.5 mg, 0.077 mmol) and THF/H$_2$O (12 mL:1.2 mL) were combined in a microwave vial and thoroughly degassed. The reaction mixture was heated at 120° C. for 1 hour under microwave irradiation and then it was diluted with EtOAc. The organic layer was separated and the aqueous extracted with another portion of EtOAc. The combined organics were washed with H$_2$O, saturated aqueous sodium chloride, dried (MgSO$_4$) and solvent removed in vacuo. The crude product was purified by automated column chromatography eluting with iso-hexane to 50% EtOAc/iso-hexane to EtOAc (gradient). Fractions found to contain pure material were combined and solvent removed in vacuo to afford the desired compound as a yellow glass, 518 mg, 59.5%.

Step 2: Preparation of 1-Benzyl-1H-pyrazole-4-carboxylic acid [5-[3-(2-morpholin-4-yl-ethoxy)-phenyl]-1-(toluene-4-sulfonyl)-1H-pyrrolo[2,3-b]pyridin-3-yl]-amide 1-Benzyl-1H-pyrazole-4-carboxylic acid [5-(3-hydroxy-phenyl)-1-(toluene-4-sulfonyl)-1H-pyrrolo[2,3-b]pyridin-3-yl]-amide (80 mg, 0.14 mmol) and 4-(2-chloroethyl)morpholine hydrochloride (37.0 mg, 0.2 mmol) were combined in anhydrous DMF (3 mL) and to this was added Cs$_2$CO$_3$ (138.7 mg, 0.43 mmol). The reaction was heated at 60° C. for 3 hours and then allowed to cool to RT. The reaction mixture was diluted with H$_2$O and extracted with DCM (×2). The combined organic phases were washed saturated aqueous sodium chloride (×4), dried (MgSO$_4$) and concentrated in vacuo. The crude material was purified via automated column chromatography eluting with DCM to 10% MeOH/DCM (gradient) to furnish the desired compound as a yellow glass, 50 mg, 52.1%.

Step 3. Preparation of title compound: 1-Benzyl-1H-pyrazole-4-carboxylic acid {5-[3-(2-morpholin-4-yl-ethoxy)-phenyl]-1H-pyrrolo[2,3-b]pyridin-3-yl}-amide 1-Benzyl-1H-pyrazole-4-carboxylic acid [5-[3-(2-morpholin-4-yl-ethoxy)-phenyl]-1-(toluene-4-sulfonyl)-1H-pyrrolo[2,3-b]pyridin-3-yl]-amide (50 mg, 0.07 mmol) potassium carbonate (51.1 mg, 037 mmol) and MeOH (4 mL) were combined in a microwave vial and heated under microwave irradiation at 100° C. for 30 minutes. The reaction mixture was reduced to half volume in vacuo and diluted with $H_2O$. The mixture was stirred for 1 hour at RT and the precipitate was collected via filtration, washed with $H_2O$, $Et_2O$ and dried in vacuo at 40° C. This afforded the title compound as a pale yellow powder, 20 mg, 51.8%.

LC/MS: RT=1.02 Min (230 nm), m/z=523 [M+H]. Total run time 1.9 min (super short pos), HP1200.

$^1$H NMR ($d_6$ DMSO): δ 2.72 (t, 2H), 3.56-3.61 (m, 4H), 4.18 (t, 2H), 5.42 (s, 2H), 6.92-6.96 (m, 1H), 7.24-7.42 (m, 8H), 7.83 (s, 1H), 8.10 (s, 1H), 8.47 (s, 1H), 8.51 (d, 1H), 8.55 (d, 1H), 9.90 (br s, 1H), 11.3-11.7 (br s, 1H) 4 protons not seen.

Example 56: 1-Benzyl-1H-pyrazole-4-carboxylic acid {5-[3-(3-dimethylamino-2,2-dimethyl-propoxy-phenyl]-1H-pyrrolo[2,3-b]pyridin-3-yl}-amide

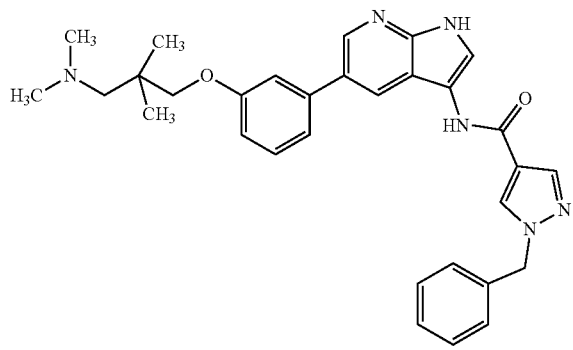 [SMILES: CN(C)CC(C)(C)COc1cccc(-c2cnc3[nH]cc(NC(=O)c4cnn(Cc5ccccc5)c4)c3c2)c1]

Preparation of (3-chloro-2,2-dimethyl-propyl)-dimethyl-amine hydrochloride

To a solution of 3-dimethylamino-2,2-dimethyl-propan-1-ol (5 g, 38.1 mmol) in toluene (100 mL) was added DMF (1 drop) followed by thionyl chloride (5 g, 41.9 mmol) drop wise at RT. After addition the reaction was heated at reflux for 3 hours and then allowed to cool to RT. The solvent was removed in vacuo and toluene (50 mL) was added and removed in vacuo. This process was repeated three more times. Toluene (50 mL) was added and the solids broken up by sonication for 10 minutes. The solid was collected via filtration, washed well with toluene, iso-hexane and dried in vacuo. This afforded the desired compound as a light brown solid, 6.68 g, 94%.

The title compound was prepared as described in Example 55, substituting (3-chloro-2,2-dimethyl-propyl)-dimethyl-amine hydrochloride (30.1 mg, 0.16 mmol) for 4-(2-chloroethyl)morpholine hydrochloride in Step 2, except heating was conducted for 18 hours at 60° C. It was isolated as a pale yellow powder, 6.5 mg, 33.7%, following the same procedure described in Step 3.

LC/MS: RT=1.10 Min (230 nm), m/z=523.2 [M+H]. Total run time 1.9 min (super short pos), HP1200.

$^1$H NMR ($d_6$ DMSO): δ 0.98 (s, 6H), 2.22 (s, 6H), 2.26 (s, 2H), 3.78 (s, 2H), 5.42 (s, 2H), 6.92-6.96 (m, 1H), 7.22-7.42 (m, 8H), 7.85 (s, 1H), 8.10 (s, 1H), 8.47 (s, 1H), 8.51-8.56 (m, 2H), 9.92 (br s, 1H), 11.50 (br s, 1H)

Example 57: 1-Benzyl-1H-pyrazole-4-carboxylic acid {5-[3-(3-morpholin-4-yl-propoxyl-phenyl]-1H-pyrrolo[2,3-b]pyridin-3-yl}-amide

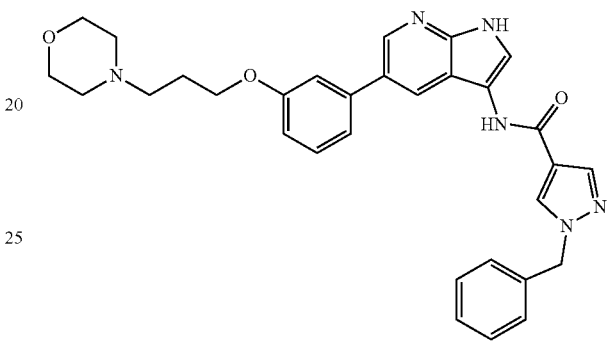

The title compound was prepared as described in Example 55, substituting 4-(3-chloropropyl)morpholine (31.9 mg, 0.195 mmol) for 4-(2-chloroethyl)morpholine in Step 2, except heating was conducted for 18 hours at 60° C. It was isolated as a powder, 8 mg, 20.2%, following the same procedure described in Step 3 and extra purification via preparative HPLC at pH4.

LC/MS: RT=1.06 Min (230 nm), m/z=537.2 [M+H]. Total run time 1.9 min (super short pos), HP1200.

$^1$H NMR ($d_6$ DMSO): δ 1.91 (quintet, 2H), 2.33-2.40 (m, 4H), 2.44 (t, 2H), 3.53-3.60 (m, 4H), 4.10 (t, 2H), 5.42 (s, 2H) 6.90-6.96 (m, 1H), 7.20-7.42 (m, 8H), 7.84 (s, 1H), 8.10 (s, 1H), 8.48 (s, 1H), 8.51-8.56 (m, 2H), 9.92 (br s, 1H), 11.51 (br s, 1H)

Example 58: 1-Benzyl-1H-pyrazole-4-carboxylic acid {5-[3-(1-methyl-piperidin-3-ylmethoxy)-phenyl]-1H-pyrrolo[2,3-b]pyridin-3-yl}-amide

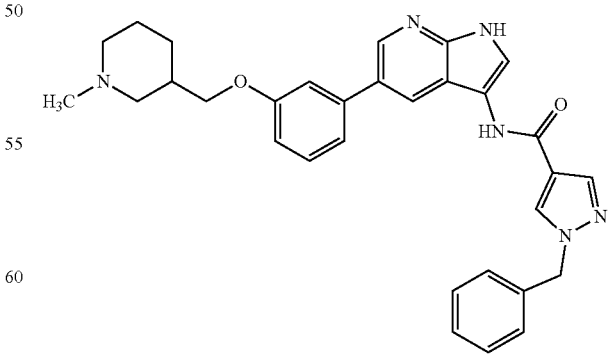

The title compound was prepared as described in Example 55, substituting 3-bromomethyl-1-methyl-piperidine (40.7 mg, 0.21 mmol) for 4-(2-chloroethyl)morpholine hydrochloride in Step 2, except heating was conducted for 18 hours at 70° C. It was isolated as a white powder, 8.8 mg, 38%, following the same procedure described in Step 3.

LC/MS: RT=1.01 Min (230 nm), m/z=521 [M+H]. Total run time 1.9 min (super short pos), HP1200.

$^1$H NMR (d$_6$ DMSO): δ 1.03-1.14 (m, 1H), 1.44-1.56 (m, 1H), 1.60-1.68 (m, 1H), 1.70-1.84 (m, 2H), 1.84-1.94 (m, 1H), 1.98-2.06 (m, 1H), 2.15 (s, 3H), 2.59-2.66 (m, 1H), 2.80-2.86 (m, 1H), 3.88-3.98 (m, 2H), 5.42 (s, 2H), 6.90-6.96 (m, 1H), 7.22-7.42 (m, 8H), 7.83 (s, 1H), 8.10 (s, 1H), 8.48 (s, H), 8.53 (dd, 2H), 9.91 (br s, 1H), 11.5 (br s, 1H).

Example 59: 1-Benzyl-1H-pyrazole-4-carboxylic acid {5-[3-(oxetan-3-yloxy-phenyl]-1H-pyrrolo[2,3-b]pyridin-3-yl}-amide

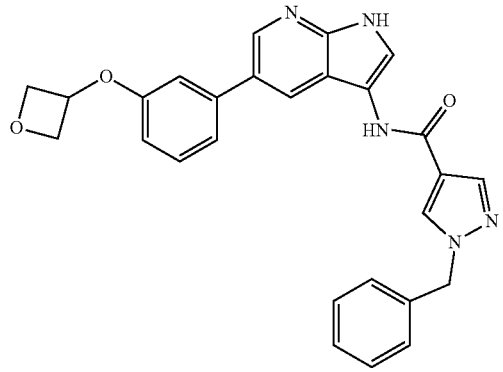 [SMILES: O=C(Nc1c[nH]c2ncc(-c3cccc(OC4COC4)c3)cc12)c1cnn(Cc2ccccc2)c1]

The title compound was prepared as described in Example 55, substituting 3-iodo-oxetane (35.9 mg, 0.195 mmol) for 4-(2-chloroethyl)morpholine hydrochloride in Step 2, except heating was conducted for 18 hours at 60° C. It was isolated as a beige powder, 4 mg, 10.9%, following the same procedure described in Step 3, and extra purification via automated column chromatography eluting with DCM to 10% MeOH/DCM (gradient).

LC/MS: RT=1.17 Min (230 nm), m/z=466.2 [M+H]. Total run time 1.9 min (super short pos), HP1200.

$^1$H NMR (d$_6$ DMSO): δ 4.59 (dd, 2H), 4.97 (dd, 2H), 5.37-5.43 (m, 3H) 6.74-6.78 (m, 1H), 7.12-7.14 (m, 1H), 7.28-7.44 (m, 7H), 7.82 (d, 1H), 8.10 (s, 1H), 8.47 (s, 1H), 8.51 (d, 1H), 8.54 (d, 1H), 9.90 (br s, 1H), 11.52 (br d, 1H).

Example 60: 1-Benzyl-1H-pyrazole-4-carboxylic acid {5-[3-(2-pyrrolidin-1-yl-ethoxy)-phenyl]-1H-pyrrolo[2,3-b]pyridin-3-yl}-amide

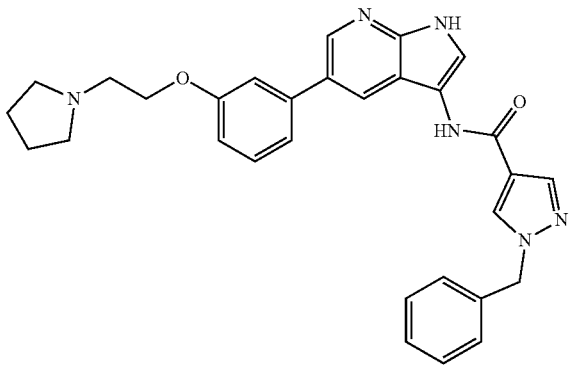 [SMILES: O=C(Nc1c[nH]c2ncc(-c3cccc(OCCN4CCCC4)c3)cc12)c1cnn(Cc2ccccc2)c1]

The title compound was prepared according to the route outlined in Scheme 6.

The title compound was prepared from 1-benzyl-1H-pyrazole-4-carboxylic acid [5-bromo-1-(toluene-4-sulfonyl)-1H-pyrrolo[2,3-b]pyridin-3-yl]-amide, the product of Step 1 in Example 43.

Step 1. Preparation of 1-Benzyl-1H-pyrazole-4-carboxylic acid [5-(4,4,5,5-tetramethyl-[1,3,2]dioxaborolan-2-yl)-1-(toluene-4-sulfonyl)-1H-pyrrolo[2,3-b]pyridin-3-yl]-amide 1-benzyl-1H-pyrazole-4-carboxylic acid [5-bromo-1-(toluene-4-sulfonyl)-1H-pyrrolo[2,3-b]pyridin-3-yl]-amide (215 mg, 0.39 mmol), bis(pinacolato)diboron (218.2 mg, 0.86 mmol), sodium acetate (96.1 mg, 1.17 mmol) and DMF (2 mL) were combined in a microwave vial. The contents were degassed by sparging with N$_2$ then Pd(dppf)Cl$_2$ (14.3 mg, 0.02 mmol) was added and the mixture heated under microwave irradiation at 140° C. for 1 hour. Bis(pinacolato)diboron (78.9 mg, 0.31 mmol) was added and the contents were degassed by sparging with N$_2$Pd(dppf)Cl$_2$ (7.1 mg, 0.01 mmol) was added and the reaction was heated under microwave irradiation at 140° C. for 30 minutes. The reaction mixture was diluted with DCM and washed with saturated aqueous sodium chloride (×4), dried (MgSO$_4$) and solvent removed in vacuo. The crude product was purified by automated column chromatography eluting with iso-hexane to 50% EtOAc/iso-hexane to EtOAc (gradient) to afford the desired compound as a yellow gum, 185 mg, 79.3%.

Step 2: Preparation of 1-[2-(3-Bromo-phenoxy)-ethyl]-pyrrolidine

3-Bromophenol (5 g, 28.9 mmol), 1-(2-chloroethyl)pyrrolidine hydrochloride (5.9 g, 34.7 mmol) were stirred in DMF (100 mL). Cesium carbonate (18.83 g, 57.8 mmol) was added and the reaction was heated at 100° C. for 4 hours. The reaction was cooled and the solvent removed in vacuo. The residue was taken up in EtOAc, washed with H$_2$O, saturated aqueous sodium chloride (×4), dried (MgSO$_4$) and concentrated in vacuo. The crude material was purified via flash chromatography eluting with 50% EtOAc/iso-hexane and then 67% EtOAc/iso-hexane to afford the desired compound as a brown oil, 1.24 g, 15.9%.

Step 3: Preparation of 1-Benzyl-1H-pyrazole-4-carboxylic acid [5-[3-(2-pyrrolidin-1-yl-ethoxy)-phenyl]-1-(toluene-4-sulfonyl)-1H-pyrrolo[2,3-b]pyridin-3-yl]-amide The title compound was prepared as described in Example 55, substituting 1-benzyl-1H-pyrazole-4-carboxylic acid [5-(4,4,5,5-tetramethyl-[1,3,2]dioxaborolan-2-yl)-1-(toluene-4-sulfonyl)-1H-pyrrolo[2,3-b]pyridin-3-yl]-amide (72 mg, 0.12 mmol) for 3-(4,4,5,5-tetramethyl-1,3,2-dioxaborolan-2-yl)phenol and 1-[2-(3-bromo-phenoxy)-ethyl]-pyrrolidine 65.1 mg, 0.24 mmol) for 1-benzyl-1H-pyrazole-4-carboxylic acid [5-bromo-1-(toluene-4-sulfonyl)-1H-pyrrolo[2,3-b]pyridin-3-yl]-amide, in Step 1. The crude product was purified by automated column chromatography eluting with DCM to 10% MeOH/DCM (gradient) to afford the desired compound as a beige glass, 38 mg, 47.9%.

Step 4: Preparation of Title compound: 1-Benzyl-1H-pyrazole-4-carboxylic acid {5-[3-(2-pyrrolidin-1-yl-ethoxy)-phenyl]-1H-pyrrolo[2,3-b]pyridin-3-yl}-amide The title compound was prepared as described in Example 55, substituting 1-benzyl-1H-pyrazole-4-carboxylic acid [5-[3-(2-pyrrolidin-1-yl-ethoxy)-phenyl]-1-(toluene-4-sulfonyl)-1H-pyrrolo[2,3-b]pyridin-3-yl]-amide (38 mg, 0.058 mmol) for 1-benzyl-1H-pyrazole-4-carboxylic acid [5-[3-(2-morpholin-4-yl-ethoxy)-phenyl]-1-(toluene-4-sulfonyl)-1H-pyrrolo[2,3-b]pyridin-3-yl]-amide, in Step 3. Following the usual work up, and trituration of the solid obtained with acetonitrile, the title compound was isolated as a beige powder, 8.6 mg, 29.5%.

LC/MS: RT=0.99 Min (230 nm), m/z=507 [M+H]. Total run time 1.9 min (super short pos), HP1200.

$^1$H NMR (d$_6$ DMSO): δ 1.64-1.73 (m, 4H), 2.82 (t, 2H), 4.15 (t, 2H), 5.42 (s, 2H), 6.92-6.96 (m, 1H), 7.24-7.42 (m, 8H), 7.83 (s, 1H), 8.10 (s, 1H), 8.48 (s, 1H), 8.51 (d, 1H), 8.55 (d, 1H), 9.91 (br s, 1H), 11.34-11.64 (br s, 1H) 4 protons not seen Example 61: 1-Benzyl-1H-pyrazole-4-carboxylic acid [4-((3R,4R)-3-amino-4-cyclopropyl-piperidin-1-yl)-5-bromo-1H-pyrrolo[2,3-b]pyridin-3-yl]-amide

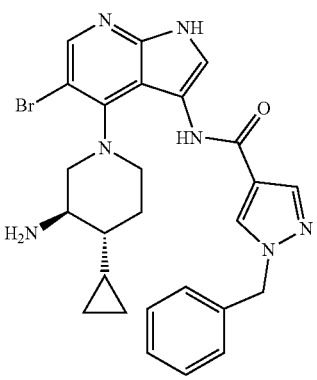 [SMILES: N[C@H]1CN(c2c(Br)cnc3[nH]cc(NC(=O)c4cnn(Cc5ccccc5)c4)c23)CC[C@@H]1C1CC1]

The title compound was prepared according to the route outlined in Scheme 2. The title compound was prepared from the product of Step 7, in Example 6, 1-benzyl-1H-pyrazole-4-carboxylic acid (5-bromo-4-fluoro-1H-pyrrolo[2,3-b]pyridin-3-yl)-amide and ((3R,4R)-4-cyclopropyl-piperidin-3-yl)-phosphoramidic acid diethyl ester.

Preparation of ((3R,4R)-4-cyclopropyl-piperidin-3-yl)-phosphoramidic acid diethyl ester Step 1: Preparation of 3,6-dihydro-2H-pyridine-1-carboxylic acid benzyl ester 1,2,3,6-tetrahydropyridine (5.24 g, 63 mmol) was stirred in DCM (30 mL) and cooled to 0° C. Et$_3$N (9.6 g, 95 mmol) was added followed by benzyl chloroformate (11.3 g, 66.2 mmol) drop wise. After addition the reaction was stirred at 5° C. for 30 minutes and then at RT for 2 hours. The reaction mixture was washed with saturated aqueous Na$_2$CO$_3$, dried (MgSO$_4$) and concentrated in vacuo. Crude material was purified by automated column chromatography, eluting with iso-Hexane to 10% EtOAc/iso-Hexane (gradient) Fractions found to contain product were combined and solvent removed in vacuo to afford the title compound as a colourless oil, 9.8 g, 71.6%.

Step 2: Preparation of 7-Oxa-3-aza-bicyclo[4.1.0]heptane-3-carboxylic acid benzyl ester To a solution of 7-Oxa-3-aza-bicyclo[4.1.0]heptane-3-carboxylic acid benzyl ester (6.86 g, 31.6 mmol) in DCM (65 mL) at 0° C. was added m-CPBA (8.28 g, 48 mmol) portion wise. After addition the reaction was maintained at 5° C. for 20 minutes and then at RT for 4 hours. The reaction mixture was diluted with Et$_2$O (150 mL), washed with 1N NaOH solution (2×50 mL), sat sodium thiosulphate solution (2×50 mL) and saturated aqueous sodium chloride. The organics were dried (MgSO$_4$) and concentrated in vacuo Crude material was purified by automated column chromatography, eluting with iso-hexane to 10% EtOAc/iso-Hexane (gradient). Fractions found to contain product were combined and solvent removed in vacuo to afford the desired compound as a colourless gum, 5.88 g, 79.8%

Step 3: Preparation of 4-Azido-3-hydroxy-piperidine-1-carboxylic acid benzyl ester and 3-azido-4-hydroxy-piperidine-1-carboxylic acid benzyl ester 7-Oxa-3-aza-bicyclo[4.1.0]heptane-3-carboxylic acid benzyl ester (3.35 g, 14.3 mmol) was dissolved in MeOH/H$_2$O 5:1 (48 mL) and ammonium chloride (0.77 g, 14.3 mmol) was added followed by sodium azide (1.87 g, 28.7 mmol). The reaction mixture was heated at 65° C. for 18 hours. The MeOH was removed in vacuo and the residue diluted with H$_2$O (15 mL) and extracted with Et$_2$O (×2). The combined organics were washed with saturated aqueous sodium chloride, dried (MgSO$_4$) and concentrated in vacuo to give the desired mixture of regioisomers, 3.84 g, 96.9%, as a colourless oil. The mixture contained a 3:1 ratio (3:1) of 4-azido-3-hydroxy-piperidine-1-carboxylic acid benzyl ester to 3-azido-4-hydroxy-piperidine-1-carboxylic acid benzyl ester.

Step 4: Preparation of 4-Azido-3-(toluene-4-sulfonyloxy)-piperidine-1-carboxylic acid benzyl ester and 3-azido-4-(toluene-4-sulfonyloxy)-piperine-1-carboxylic acid benzyl ester 4-Azido-3-hydroxy-piperidine-1-carboxylic acid benzyl ester and 3-azido-4-hydroxy-piperidine-1-carboxylic acid benzyl ester (3.84 g, 13.9 mmol) were dissolved in DCM (18 mL) and pyridine (2.97 g, 37.53 mmol) was added. The solution was cooled to 0'C and p-toluenesulfonyl chloride (5.56 g, 29.2 mmol) in DCM (7 mL) was added drop wise. The reaction was allowed to stir at RT for 68 hours. Pyridine (1.96 g, 24.8 mmol) and p-toluenesulfonyl chloride (1 g, 5.25 mmol) were added and the reaction was stirred at RT for 24 hrs. The reaction mixture was concentrated in vacuo to give a white solid that was dissolved in EtOAc and washed with saturated aqueous sodium chloride, dried (MgSO$_4$) and concentrated in vacuo. The crude material was purified via automated column chromatography eluting with iso-hexane to 50% EtOAc/iso-hexane (gradient) to give the desired mixture of regioisomers, 5.62 g, 94%, as a colourless oil. The mixture contained a ratio (77:23) of 4-azido-3-

(toluene-4-sulfonyloxy)-piperidine-1-carboxylic acid benzyl ester to 3-azido-4-(toluene-4-sulfonyloxy)-piperidine-1-carboxylic acid benzyl ester.

Step 5: Preparation of 4-Amino-3-(toluene-4-sulfonyloxy)-piperidine-1-carboxylic acid benzyl ester and 3-amino-4-(toluene-4-sulfonyloxy)-piperidine-1-carboxylic acid benzyl ester Sodium borohydride (300 mg, 7.93 mmol) was added in portions to a solution of copper(II)sulphate pentahydrate (1.04 g, 4.15 mmol) in MeOH (20 mL) at 0'C. After 5 minutes a solution of 4-azido-3-(toluene-4-sulfonyloxy)-piperidine-1-carboxylic acid benzyl ester and 3-azido-4-(toluene-4-sulfonyloxy)-piperidine-1-carboxylic acid benzyl ester (3.57 g, 8.29 mmol) in MeOH (10 mL) was added drop wise, followed by sodium borohydride (600 mg, 15.86 mmol) in portions. After addition stirring was continued at 0° C. for 1 hour. The reaction mixture was filtered through a plug of celite and concentrated in vacuo. The residue was taken up in DCM then washed with $H_2O$, saturated aqueous ammonium chloride, saturated aqueous sodium chloride, dried ($MgSO_4$) and concentrated in vacuo. The desired mixture of regioisomers was obtained as a colourless oil, 2.77 g, 83.3%.

Step 6: Preparation of 4-(Diethoxy-phosphorylamino)-3-(toluene-4-sulfonyloxy)-piperidine-1-carboxylic acid benzyl ester and 3-(diethoxy-phosphorylamino)-4-(toluene-4-sulfonyloxy)-piperidine-1-carboxylic acid benzyl ester To a solution of 4-amino-3-(toluene-4-sulfonyloxy)-piperidine-1-carboxylic acid benzyl ester and 3-amino-4-(toluene-4-sulfonyloxy)-piperidine-1-carboxylic acid benzyl ester 2.77 g, 6.84 mmol) in DCM (22 mL) was added triethylamine (1.38 g, 13.68 mmol) and the solution cooled to 0° C. Diethyl chlorophosphate (1.3 g, 7.52 mmol) was added and the mixture allowed to attain RT over 30 minutes. Diethyl chlorophosphate (0.24 g 1.38 mmol) was added and stirred for 30 minutes at RT. The reaction was diluted with $H_2O$ and the organics separated, washed with saturated aqueous sodium chloride, dried ($MgSO_4$) and concentrated in vacuo. EtOAc was added to the residue and the crystals formed were collected via filtration and dried in vacuo to afford the desired compound, 0.604 g, 16.4%. The filtrate was concentrated in vacuo and the residue purified via automated column chromatography eluting with EtOAc to afford more of the desired compound, 2.76 g, 74.8%, as a colorless oil.

Step 7: Preparation of 7-(Diethoxy-phosphoryl)-3,7-diaza-bicyclo[4.1.0]heptane-3-carboxylic acid benzyl ester To a solution of 4-(diethoxy-phosphorylamino)-3-(toluene-4-sulfonyloxy)-piperidine-1-carboxylic acid benzyl ester and 3-(diethoxy-phosphorylamino)-4-(toluene-4-sulfonyloxy)-piperidine-1-carboxylic acid benzyl ester (2.6 g, 4.81 mmol) in THF (25 mL) at 0° C. was added sodium hydride, 60% dispersion in mineral oil, (288.6 mg, 7.21 mmol) in portions. The reaction was stirred for 30 minutes then diluted with $H_2O$. The mixture was extracted with EtOAc (×2) and the combined organics were washed with saturated aqueous sodium chloride, dried ($MgSO_4$) and concentrated in vacuo. The residue was purified via automated column chromatography eluting with EtOAc to give the desired compound as a colourless oil, 1.34 g, 76.5%.

Step 8: Preparation of (3R,4R)-4-Cyclopropyl-3-(diethoxy-phosphorylamino)-piperidine-1-carboxylic acid benzyl ester To a suspension of copper(I)iodide (38.8 mg, 0.2 mmol) in THF (10 mL) at −30° C. was added cyclopropylmagnesium bromide, 0.5M in THF (16.3 mL, 8.15 mmol) drop wise. This was stirred for 15 minutes, then 7-(diethoxy-phosphoryl)-3,7-diaza-bicyclo[4.1.0]heptane-3-carboxylic acid benzyl ester (750 mg, 2.04 mmol) in THF (5 mL) was added drop wise at −30° C. The reaction was warmed to RT over 2 hours, and diluted with EtOAc and $H_2O$ and the resultant emulsion filtered through celite. The filtrate was transferred to a separating funnel. The organics were separated and the aqueous extracted with EtOAc. The combined organics were washed with saturated aqueous sodium chloride, dried ($MgSO_4$) and concentrated in vacuo. The resultant yellow oil was purified via automated column chromatography eluting with EtOAc, to afford the desired compound as a gum, 321 mg, 38.4%, that solidified on standing.

Step 9: Preparation of ((3R,4R)-4-Cyclopropyl-piperidin-3-yl)-phosphoramidic acid diethyl ester (3R,4R)-4-Cyclopropyl-3-(diethoxy-phosphorylamino)-piperidine-1-carboxylic acid benzyl ester (321 mg, 0.78 mmol) was dissolved in MeOH (5 mL) and palladium on charcoal, 10% (20 mg) was added under a stream of $N_2$. This was then evacuated and back filled with nitrogen three times, before finally evacuating and connecting to a hydrogen atmosphere. The reaction mixture was shaken under hydrogen for 5 hours. The reaction was evacuated and back filled with nitrogen three times. The mixture was filtered through a pad of celite and the filtrate concentrated in vacuo to give the desired amine, ((3R,4R)-4-cyclopropyl-piperidin-3-yl)-phosphoramidic acid diethyl ester, as a colourless oil, 232 mg.

Preparation of title compound: 1-Benzyl-1H-pyrazole-4-carboxylic acid [4-((3R,4R)-3-amino-4-cyclopropyl-piperidin-1-yl)-5-bromo-1H-pyrrolo[2,3-b]pyridin-3-yl]-amide 1-Benzyl-1H-pyrazole-4-carboxylic acid (5-bromo-4-fluoro-1H-pyrrolo[2,3-b]pyridin-3-yl)-amide (90 mg, 0.22 mmol), ((3R,4R)-4-cyclopropyl-piperidin-3-yl)-phosphoramidic acid diethyl ester (230 mg, 0.83 mmol) and 1-butanol (5 mL) were combined in a sealed tube and heated at 3140-ES-085 at 160° C. for 60 hours. The reaction mixture was concentrated in vacuo and the residue was purified via automated column chromatography eluting with DCM to 25% MeOH/DCM (gradient). The material obtained was further purified by preparative HPLC at pH4. The material obtained was taken up in DCM/IPA (3:1), washed with saturated aqueous sodium hydrogen bicarbonate, dried ($MgSO_4$) and concentrated in vacuo. The residue was dried in vacuo at 40° C. o/n to afford the desired title compound as a golden brown powder, 3.3 mg, 2.84%.

LC/MS: RT=1.03 Min (230 nm), m/z=534 [M+H]. Total run time 1.9 min (super short pos), HP1200.

¹H NMR (d₆ DMSO): δ 0.16-0.07 (m, 1H), 0.15-0.25 (m, 2H), 0.30-0.46 (m, 3H), 1.31-1.44 (m, 1H), 1.64-1.76 (m, 1H), 2.71-2.81 (m, 1H), 2.92-3.03 (m, 1H), 5.40 (s, 2H), 7.20-7.38 (m, 5H), 7.62 (s, 1H), 8.04 (s, 1H), 8.18 (s, 1H), 8.46 (s, 1H), 9.63 (br s, 1H), 11.56-11.94 (br s, 1H) 5 protons not seen Example 62: 1-Benzyl-1H-pyrazole-4-carboxylic acid [5-(2-fluoro-4-pyrrolidin-1-ylmethyl-phenyl)-1H-pyrrolo[2,3-b]pyridin-3-yl]-amide

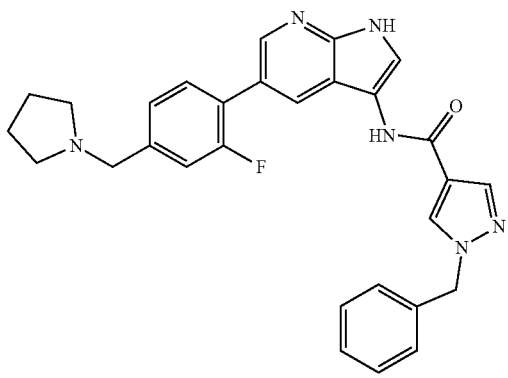 [SMILES: O=C(Nc1c[nH]c2ncc(-c3ccc(CN4CCCC4)cc3F)cc12)c1cnn(Cc2ccccc2)c1]

The title compound was prepared by an analogous route to the one outlined in Scheme 4.

The title compound was prepared as described in Example 43, substituting 2-fluoro-4-formyl boronic acid (109 mg, 0.65 mmol) for 3-formylphenylboronic acid, saturated aqueous sodium hydrogen carbonate (2 mL) for K₂CO₃ and MeCN (4 mL) for THF/H₂O in Step 2. The reaction was heated at 130° C. for 2 hours under microwave irradiation. The reaction was diluted with DCM, washed with H₂O, the aqueous was extracted again with DCM and the combined organics were washed with saturated aqueous sodium chloride, dried (MgSO₄) and solvent removed in vacuo to afford a brown gum. This crude material was purified by automated column chromatography, eluting with iso-hexane to 90% EtOAc/iso-hexane—EtOAc (gradient). Fractions found to contain pure material were combined and solvent removed in vacuo to afford the desired Suzuki product as a yellow glass, 108 mg, 50%.

In Step 3, pyrrolidine 925.2 mg, 0.35 mmol) was substituted for dimethylamine, 2.0M solution in THF and sodium cyanoborohydride (16.7 mg, 0.27 mmol) was substituted for sodium triacetoxyborohydride.

The title compound was isolated as a white powder, 16.6 mg, 68.1%, following the usual protocol for deprotection of the tosyl group.

LC/MS: RT=1.00 Min (230 nm), m/z=495 [M+H]. Total run time 1.9 min (super short pos), HP1200.

¹H NMR (d₆ DMSO): δ 1.69-1.75 (m, 4H), 2.45-2.49 (m, 4H), 3.64 (s, 2H), 5.45 (s, 2H), 7.24-7.40 (m, 7H), 7.59-7.55 (m, 1H), 7.83 (s, 1H), 8.08 (s, 1H), 8.37-8.39 (m, 1H), 8.40-8.42 (m, 1H), 8.46 (br s, 1H), 9.93 (br s, 1H), 11.56 (br s, 1H)

Example 63: 1-Benzyl-1H-pyrazole-4-carboxylic acid [5-(3-pyrrolidin-1-yl-phenyl)-1H-pyrrolo[2,3-b]pyridin-3-yl]-amide

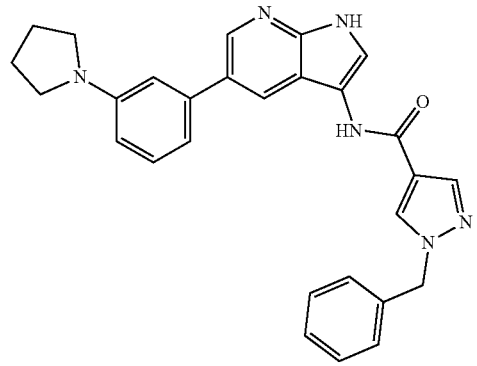 [SMILES: O=C(Nc1c[nH]c2ncc(-c3cccc(N4CCCC4)c3)cc12)c1cnn(Cc2ccccc2)c1]

The title compound was prepared according to the route outlined in Scheme 4. The title compound was prepared as described in Example 43, substituting 1-[3-(4,4,5,5-tetramethyl-1,3,2-dioxaborolan-2-yl)phenyl]pyrrolidine (59.6 mg, 0.22 mmol) for 3-formylphenylboronic acid in Step 2 Subsequent deprotection as described for Example 43, Step 4, furnished the title compound as a brown powder, 54.2 mg, 62.4%.

LC/MS: RT=1.33 Min (230 nm), m/z=463 [M+H]. Total run time 1.9 min (super short pos), HP1200.

¹H NMR (d₆ DMSO): δ 1.94-2.02 (m, 4H), 5.41 (s, 2H), 6.52-6.57 (dd, 1H), 6.77-6.80 (m, 1H), 6.87-6.91 (d, 1H), 7.24-7.41 (m, 6H), 7.82 (s, 1H), 8.10 (s, 1H), 8.45-8.48 (m, 2H), 8.50-8.52 (d, 1H), 9.91 (s, 1H), 11.47 (br s, 1H) 4 protons not seen Example 64: 1-Benzyl-1H-pyrazole-4-carboxylic acid [5-(1-methyl-11H-pyrazol-4-yl)-1H-pyrrolo[2,3-b]pyridin-3-yl]-amide

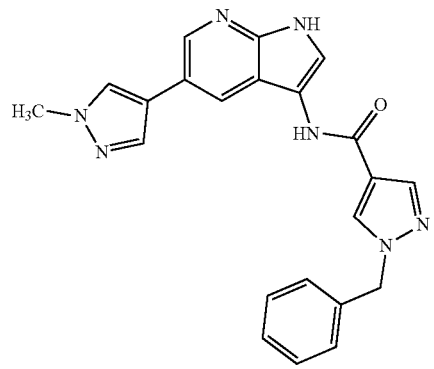 [SMILES: Cn1cc(-c2cnc3[nH]cc(NC(=O)c4cnn(Cc5ccccc5)c4)c3c2)cn1]

The title compound was prepared according to the route outlined in Scheme 4. The title compound was prepared as described in Example 43, substituting 1-methyl-4-(4,4,5,5- tetramethyl-1,3,2-dioxaborolan-2-yl)-1H-pyrazole (41.6 mg, 0.2 mmol) for 3-formylphenylboronic acid, aqueous sodium carbonate solution, 2M (0.18 mL, 0.36 mmol), tetrakis(triphenylphosphine)palladium(0) (10.5 mg, 9.1 μMol) for Pd(dppf)Cl₂, 1,4-dioxane (2 mL) for THF/H₂O (10:1) and heating at 150° C. for 20 minutes under microwave irradiation, in Step 2. Subsequent deprotection as described for Example 43, Step 4, furnished the title compound as a yellow powder, 32.6 mg, 52.6%.

LC/MS: RT=1.01 Min (230 nm), m/z=398 [M+H]. Total run time 1.9 min (super short pos), HP1200.

¹H NMR (d₆ DMSO): δ 3.88 (s, 3H), 5.41 (s, 2H), 7.27-7.41 (m, 5H), 7.72 (s, 1H), 7.84 (d, 1H), 8.09 (s, 1H), 8.12 (s, 1H), 8.27-8.30 (d, 1H), 8.45-8.48 (m, 2H), 9.85 (s, 1H), 11.40 (br s, 1H)

Example 65: 1-Benzyl-1H-pyrazole-4-carboxylic acid (5-pyridin-4-yl-1H-pyrrolo[2,3-b]pyridin-3-yl)-amide

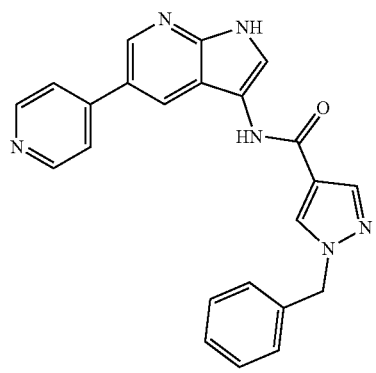 [SMILES: O=C(Nc1c[nH]c2ncc(-c3ccncc3)cc12)c1cnn(Cc2ccccc2)c1]

The title compound was prepared from Example 1.

1-Benzyl-1H-pyrazole-4-carboxylic acid (5-bromo-1H-pyrrolo[2,3-b]pyridin-3-yl)-amide (75 mg, 0.19 mmol), pyridine-4-boronic acid (34.9 mg, 0.28 mmol), K₃PO₄, 2M aqueous solution (0.19 mL, 0.38 mmol) and Pd(dppf)Cl₂ (13.3 mg, 0.02 mmol) were combined in 1,4-dioxane (2 mL) and thoroughly degassed. The reaction mixture was heated at 120° C. for 1 hour under microwave irradiation and then it was partitioned between saturated aqueous sodium hydrogen carbonate and EtOAc. The organic layer was separated and the aqueous extracted with another portion of EtOAc. The combined organics were washed with H₂O, saturated aqueous sodium chloride, dried (MgSO₄) and solvent removed in vacuo. This crude material was purified by flash chromatography, eluting with DCM then 4% MeOH/DCM then 7% MeOH/DCM. Fractions found to contain pure material were combined and solvent removed in vacuo to afford the desired product as a beige solid, 30.9 mg, 41.4%.

LC/MS: RT=1.80 Min (254 nm), m/z=395 [M+H]. Total run time 3.75 min (short pos/neg), HP1100.

¹H NMR (d₆ DMSO): δ 5.42 (s, 2H), 7.29-7.41 (m, 5H), 7.78 (m, 2H), 7.85 (d, 1H), 8.10 (d, 1H), 8.48 (s, 1H), 8.63-8.80 (m, 4H), 9.96 (s, 1H), 11.67 (br d, 1H)

Example 66: 1-Benzyl-1H-pyrazole-4-carboxylic acid (5-pyridin-3-yl-1H-pyrrolo[2,3-b]pyridin-3-yl)-amide

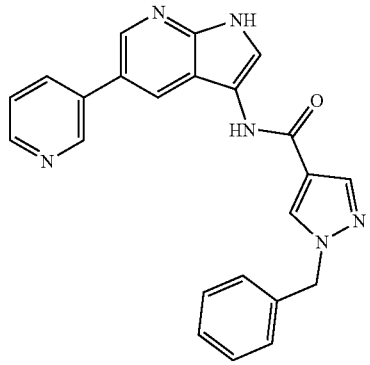 [SMILES: O=C(Nc1c[nH]c2ncc(-c3cccnc3)cc12)c1cnn(Cc2ccccc2)c1]

The title compound was prepared from Example 1, using exactly the same protocol as Example 65 but substituting pyridine-3-boronic acid (75 mg, 0.19 mmol) for pyridine-4-boronic acid. The title compound was isolated as a beige solid, 24.8 mg, 33.2%.

LC/MS: RT=1.93 Min (254 nm), m/z=395 [M+H]. Total run time 3.75 min (short pos/neg), HP1100.

¹H NMR (d₆ DMSO): δ 5.41 (s, 2H), 7.28-7.41 (m, 5H), 7.49-7.54 (m, 1H), 7.85 (d, 1H), 8.10 (d, 1H), 8.11-8.15 (m, 1H), 8.47 (s, 1H), 8.55-8.60 (m, 3H), 8.94 (dd, 1H), 9.91 (s, 1H), 11.59 (br d, 1H)

Example 67: 1-(3-Methoxy-benzyl)-1H-pyrazole-4-carboxylic acid (5-bromo-1H-pyrrolo[2,3-b]pyridin-3-yl)-amide

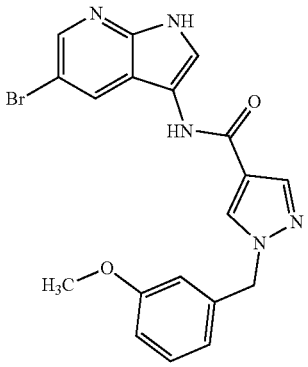 [SMILES: COc1cccc(Cn2cc(C(=O)Nc3c[nH]c4ncc(Br)cc34)cn2)c1]

The title compound was prepared according to the route outlined in Scheme 1, and using the methodology described for Example 1, substituting 1-(3-methoxy-benzyl)-1H-pyrazole-4-carboxylic acid (120.8 mg, 0.52 mmol) for 1-benzyl-1H-pyrazole-4-carboxylic acid in Step 1. The title compound was isolated as a pale brown solid, 73.6 mg, 36.6%.

LC/MS: RT=2.35 Min (254 nm), m/z=426.3 [M+H]. Total run time 3.75 min (short pos/neg), HP1100.

¹H NMR (d₆ DMSO): δ 3.75 (s, 3H), 5.37 (s, 2H), 6.83-6.90 (m, 3H), 7.29 (t, 1H), 7.84 (d, 1H), 8.08 (s, 1H), 8.28 (d, 1H), 8.44 (s, 1H), 8.48 (d, 1H), 9.88 (s, 1H), 11.69 (s, 1H)

Example 68: 1-(2-Fluoro-benzyl-1H-pyrazole-4-carboxylic acid (5-bromo-1H-pyrrolo[2,3-b]pyridin-3-yl)-amide

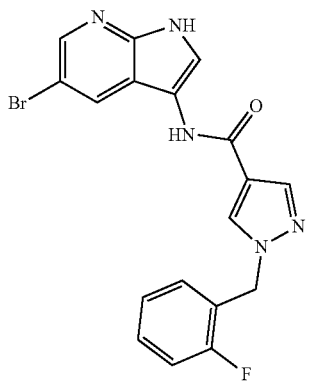 [SMILES: O=C(Nc1c[nH]c2ncc(Br)cc12)c1cnn(Cc2ccccc2F)c1]

The title compound was prepared according to the route outlined in Scheme 1, and using the methodology described for Example 1, substituting 1-(2-fluoro-benzyl)-1H-pyrazole-4-carboxylic acid (114.5 mg, 0.52 mmol), prepared in a similar way to 1-(-fluoro-benzyl)-1H-pyrazole-4-carboxylic acid as described in Example 17, for 1-benzyl-1H-pyrazole-4-carboxylic acid in Step 1. In Step 3, the product precipitated following dilution of the reaction mixture with H$_2$O. It was separated via filtration, washed well with H$_2$O and Et$_2$O then dried in vacuo at 40° C. to afford the title compound as a pale orange solid, 93.1 mg, 47.7%.

LC/MS: RT=2.27 Min (254 nm), m/z=414.3 [M+H]. Total run time 3.75 min (short pos/neg), HP1100.

$^1$H NMR (d$_6$ DMSO): δ 5.47 (s, 2H), 7.20-7.32 (m, 3H), 7.41 (q, 1H), 7.84 (d, 1H), 8.07 (s, 1H), 8.28 (d, 1H), 8.44 (s, 1H), 8.48 (d, 1H), 9.89 (s, 1H), 11.70 (s, 1H)

Example 69: 1-(2-Cyano-benzyl))-1H-pyrazole-4-carboxylic acid (5-bromo-1H-pyrrolo[2,3-b]pyridin-3-yl)-amide

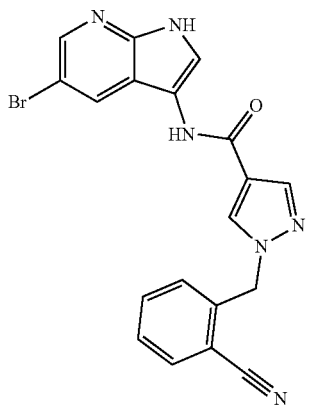 [SMILES: N#Cc1ccccc1Cn1cc(C(=O)Nc2c[nH]c3ncc(Br)cc23)cn1]

The title compound was prepared according to the route outlined in Scheme 1, and using the methodology described for Example 1, substituting 1-(2-cyano-benzyl)-1H-pyrazole-4-carboxylic acid (118.2 mg, 0.52 mmol), prepared in a similar way to 1-(-fluoro-benzyl)-1H-pyrazole-4-carboxylic acid as described in Example 17, for 1-benzyl-1H-pyrazole-4-carboxylic acid in Step 1. In Step 3, following the usual aqueous work up, the crude material was triturated in Et$_2$O, filtered, washed with Et$_2$O and dried in vacuo at 40° C. to afford the title compound as a solid, 54.8 mg, 27.7%.

LC/MS: RT=2.20 Min (254 nm), m/z=423.3 [M+H]. Total run time 3.75 min (short pos/neg), (HP1100.

$^1$H NMR (d$_6$ DMSO): δ 5.62 (s, 2H), 7.36 (d, 1H), 7.56 (td, 1H), 7.73 (td, 1H), 7.84 (d, 1H), 7.91 (dd: 1H), 8.12 (s, 1H), 8.28 (d, 1H), 8.48 (d, 1H), 8.50 (s, 1H), 9.93 (s, 1H), 11.71 (br s, 1H)

Example 70: 1-(1H-pyrrol-2-ylmethyl)-1H-pyrazole-4-carboxylic acid (5-bromo-1H-pyrrolo[2,3-b]pyridin-3-yl)-amide

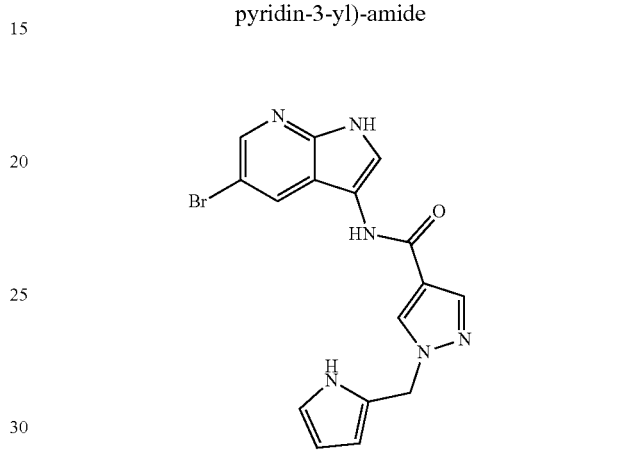

The title compound was prepared according to the route outlined in Scheme 1, and using the methodology described for Example 1, substituting potassium 1-(1H-pyrrol-2-ylmethyl)-1H-pyrazole-4-carboxylate (61.2 mg, 0.32 mmol) for 1-benzyl-1H-pyrazole-4-carboxylic acid in Step 1. In Step 3, following the usual aqueous work up, the crude material was purified via automated column chromatography eluting with DCM to 20% MeOH/DCM (gradient). Fractions found to contain product were combined and solvent removed in vacuo and the residue further purified via preparative HPLC at pH 9 to afford the title compound as white solid, 15.4 mg, 12.5%.

Preparation of potassium 1-(1H-pyrrol-2-ylmethyl)-1H-pyrazole-4-carboxylate

Step 1: Preparation of 1-methanesulfonyl-1H-pyrrole-2-carbaldehyde

A solution of pyrrole carboxaldehyde (1.0 g, 10.5 mmol) in THF (20 mL) was added drop wise to a suspension of sodium hydride, 60% dispersion in mineral oil (484 mg, 12.1 mmol) and THF (60 mL) and the mixture stirred for 15 mins at RT. Methane sulfonyl chloride (1.69 g, 14.72 mmol) was added drop wise and the reaction was stirred for a further 1 hour at RT. The reaction was diluted with H$_2$O and concentrated under reduced pressure. The residual aqueous was extracted with DCM (×5) and the combined extracts were then washed successively with saturated aqueous sodium bicarbonate, H$_2$O and with saturated aqueous sodium chloride. The organics were dried over MgSO$_4$ and concentrated under reduced pressure to afford an oil that was purified by automated flash chromatography eluting with of iso-hexane to 30% EtOAc/iso-hexane (gradient). Fractions found to contain pure product were combined and solvent removed in vacuo to afford the title compound as a colourless oil, 1.3 g, 71.4%.

Step 2: Preparation of (1-methanesulfonyl-1H-pyrrol-2-yl)-MeOH

1-Methanesulfonyl-1H-pyrrole-2-carbaldehyde (1.3 g, 7.51 mmol) was stirred in a mixture of DCM (180 mL) and MeOH (63 ml) at 0° C. Sodium borohydride (428 mg, 11.3 mmol) was added in portions and the reaction mixture was left to stir at 0° C. for 1.5 hours. The reaction mixture was diluted with DCM (80 mL) and oxalic acid, 5% aqueous solution (200 mL) was added drop wise and stirring continued at 0° C. for a further 15 minutes, before allowing the reaction mixture to warm to RT. The organic layer was separated, washed with $H_2O$ (2×250 ml), dried over $MgSO_4$ and concentrated under reduced pressure to afford the title compound as pink crystals, 0.865 g, 65.8%.

Step 3: Preparation of 1-(1-methanesulfonyl-1H-pyrrol-2-ylmethyl)-1H-pyrazole-4-carboxylic acid ethyl ester DIPEA (1.29 mL, 7.41 mmol) was added to a solution of (1-methanesulfonyl-1H-pyrrol-2-yl)-MeOH (865 mg, 4.94 mmol) in DCM (27 mL) and cooled to 0° C. Methanesulfonyl chloride (0.57 mL, 7.41 mmol) was added drop wise and the reaction was stirred at 0° C. for 20 minutes and RT for 30 minutes. The reaction mixture was diluted with DCM and washed successively with ice cold $H_2O$, cold 10% aqueous hydrochloric acid solution and followed by saturated aqueous sodium hydrogen bicarbonate. The organics were dried over $MgSO_4$ and concentrated under reduced pressure (low temperature) to afford 2-chloromethyl-1-methanesulfonyl-1H-pyrrole as an orange oil which was used immediately as the compound can polymerise on standing. A solution of 2-chloromethyl-1-methanesulfonyl-1H-pyrrole (1.02 g, 5.27 mmol) in acetone (11 mL) was added to a suspension of 1H-pyrazole-4-carboxylic acid ethyl ester (703 mg, 5.02 mmol) and potassium carbonate (2.78 g, 20.1 mmol) in acetone (10 mL). Stirring was continued for 70 hours at RT and then the reaction mixture was filtered and the filter cake washed through with EtOAc. The filtrate was concentrated under reduced pressure and the residue was taken up in EtOAc, washed with $H_2O$, dried ($MgSO_4$) and concentrated under reduced pressure. The crude material was purified by automated flash chromatography eluting with iso-hexane to EtOAc/iso-hexane to EtOAc (gradient). Fractions containing pure product were combined and concentrated in vacuo to afford the desired compound as an orange oil that solidified on standing, 442 mg, 29.6%. Fractions containing product and an impurity were combined and concentrated in vacuo and the residue further purified via SCX-2 ion exchange column giving a further 359 mg, 24.1%, of title compound as an off white solid.

Step 4. Preparation of Potassium 1-(1H-pyrrol-2-ylmethyl)-1H-pyrazole-4-carboxylate 1-(1-Methanesulfonyl-1H-pyrrol-2-ylmethyl)-1H-pyrazole-4-carboxylic acid ethyl ester (801 mg, 2.69 mmol) was dissolved in a mixture of MeOH:THF (1:1, 20 mL) and a solution of potassium hydroxide (301.8 mg, 5.38 mmol) in $H_2O$ (2 mL) was added. The reaction mixture was then refluxed for 4 hours, cooled and concentrated in vacuo. The residue was dried in a dessicator at 60° C. for 18 hours to give the title compound as a solid, 860 mg, 93.5%. It was assumed by the recovery, and reaction stoichiometry to be predominantly the desired title compound with 2 equivalents of KOH present and it was used without further purification.

Step 5: Preparation of title compound: 1-(1H-pyrrol-2-ylmethyl)-1H-pyrazole-4-carboxylic acid (5-bromo-1H-pyrrolo[2,3-b]pyridin-3-yl)-amide 5-Bromo-1H-pyrrolo[2,3-b]pyridin-3-ylamine (101.8 mg, 0.48 mmol) and potassium 1-(1H-pyrrol-2-ylmethyl)-1H-pyrazole-4-carboxylate (61.2 mg, 0.179 mmol) were stirred in DMF (4 mL) and triethylamine (97 mg, 0.13 ml, 0.96 mmol) was added followed by HATU (183 mg, 0.48 mmol). The reaction mixture was left to stir at RT for 72 hours and diluted with EtOAc. The organics were separated and the aqueous extracted with a further portion of EtOAc. The combined extracts were washed with saturated aqueous sodium chloride (×3), dried ($MgSO_4$) and concentrated in vacuo. The crude material was purified automated flash chromatography eluting with DCM to 20% MeOH/DCM (gradient). Fractions containing product were combined and concentrated in vacuo and the residue was further purified by preparative HPLC at pH9 to afford the title compound as a white solid, 15.4 mg, 22.3%.

LC/MS: RT=1.09 Min (254 nm), m/z=386.0 [M+H]. Total run time 1.9 min (super short pos), HP1200.

$^1$H NMR ($d_6$ DMSO): δ 5.28 (s, 2H), 6.00 (m, 1H), 6.13 (s, 1H), 6.75 (m, 1H), 7.83 (d, 1H), 8.04 (s, 1H), 8.23 (s, 1H), 8.27 (d, 1H), 8.47 (d, 1H), 9.88 (s, 1H), 11.03 (s, 1H), 11.69 (s, 1H)

Example 71: 1-(4-Fluoro-benzyl)-1H-pyrazole-4-carboxylic acid (5-bromo-1H-pyrrolo[2,3-b]pyridin-3-yl)-amide

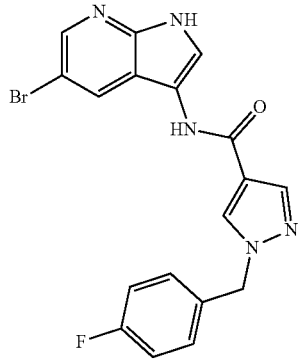

The title compound was prepared according to the route outlined in Scheme 1, and using the methodology described for Example 1, substituting 1-(4-fluoro-benzyl)-1H-pyrazole-4-carboxylic acid (45.7 mg, 0.21 mmol), as described in Example 17, for 1-benzyl-1H-pyrazole-4-carboxylic acid in Step 1. The title compound was isolated as a brown solid, 26.7 mg, 34.2%.

LC/MS: RT=2.26 Min (270 nm), m/z=416.3 [M+H]. Total run time 3.75 min (short pos/neg), HP1100.

$^1$H NMR ($d_6$ DMSO): δ 5.40 (s, 2H), 7.19-7.23 (m, 2H), 7.35-7.38 (m, 2H), 7.84 (d, 1H), 8.08 (s, 1H), 8.28 (d, 1H), 8.45 (s, 1H), 8.48 (d, 1H), 9.88 (s, 1H), 11.69 (br s, 1H)

Example 72: 1-Benzyl-1H-pyrazole-4-carboxylic acid (5-methyl-1H-pyrrolo[2,3-b]pyridin-3-yl)-amide

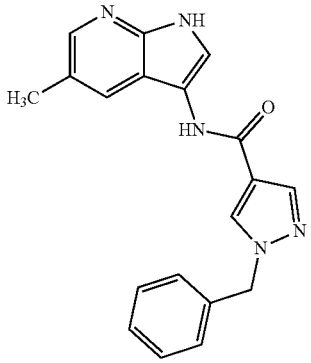 [SMILES: Cc1cnc2[nH]cc(NC(=O)c3cnn(Cc4ccccc4)c3)c2c1]

The title compound was prepared according to an analogous route to that outlined in Scheme 1, and using the methodology described for Example 1, substituting 5-methyl-1H-pyrrolo[2,3-b]pyridine (1.06 g, 8.02 mmol) for 5-bromo-1H-pyrrolo[2,3-b]pyridine in Step 1. In Step 2, the methodology from Example 6, Step 6, substituting 5-methyl-3-nitro-1H-pyrrolo[2,3-b]pyridine (1.42 g, 8.02 mmol) for 5-bromo-4-fluoro-3-nitro-1H-pyrrolo[2,3-b]pyridine, was used. The title compound was isolated as a cream solid, 22.7 mg, 20.2%, following the protocol described for Example 1, Step 3, substituting 5-methyl-1H-pyrrolo[2,3-b]pyridin-3-ylamine (50 mg, 0.34 mmol) for 5-bromo-1H-pyrrolo[2,3-b]pyridin-3-ylamine. LC/MS: RT=2.04 Min (270 nm), m/z=332.4 [M+H]. Total run time 3.75 min (short pos/neg), HP1100.

$^1$H NMR ($d_6$ DMSO): δ 2.38 (s, 3H), 5.40 (s, 2H), 7.29-7.40 (m, 5H), 7.69 (d, 1H), 7.97-7.98 (m, 1H), 8.06-8.08 (m, 2H), 8.44 (s, 1H), 9.80 (s, 1H), 11.25 (br s, 1H)

Example 73: 1-Benzyl-1H-pyrazole-4-carboxylic acid (5-chloro-1H-pyrrolo[2,3-b]pyridin-3-yl)-amide

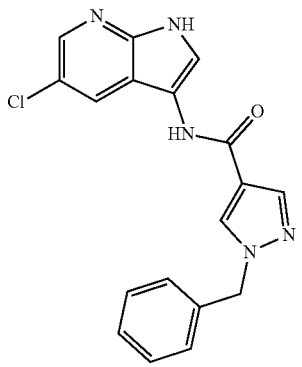 [SMILES: O=C(Nc1c[nH]c2ncc(Cl)cc12)c1cnn(Cc2ccccc2)c1]

The title compound was prepared according to an analogous route to that outlined in Scheme 1, and using the methodology described for Example 1, in Steps 1 and 2, substituting 5-chloro-1H-pyrrolo[2,3-b]pyridine (400 mg, 2.62 mmol) for 5-bromo-1H-pyrrolo[2,3-b]pyridine in Step 1.

Step 3: Preparation of title compound: 1-Benzyl-1H-pyrazole-4-carboxylic acid (5-chloro-1H-pyrrolo[2,3-b]pyridin-3-yl)-amide 5-Chloro-1H-pyrrolo[2,3-b]pyridin-3-ylamine (37.4 mg, 0.22 mmol), HATU (95.1 mg, 0.2 mmol) and acetonitrile (5 mL) were combined in a microwave vial, 1-Benzyl-1H-pyrazole-4-carboxylic acid (49.6 mg, 0.25 mmol) and DIPEA (0.09 mL, 0.50 mmol) were added, and contents degassed. The reaction was then heated at 80° C. under microwave irradiation for 1 hour. The reaction was partitioned between EtOAc and H$_2$O and the organics separated. The aqueous was extracted with a further portion of EtOAc and the combined extracts were washed with H$_2$O, saturated aqueous sodium chloride, dried (MgSO$_4$) and concentrated in vacuo. The crude material was purified by automated column chromatography eluting with 30% EtOAc/isohexane to 100% EtOAc. Fractions containing pure material were combined, concentrated in vacuo to afford the desired compound as a brown powder, 24 mg, 30.6%.

LC/MS: RT=2.19 Min (270 nm), m/z=352 [M+H]. Total run time 3.75 min (short pos/neg), HP1100.

$^1$H NMR ($d_6$ DMSO): δ 5.42 (s, 2H), 7.29-7.41 (m, 5H), 7.86 (s, 1H), 8.09 (s, 1H), 8.23 (s, 1H), 8.35 (s, 1H), 8.46 (s, 1H), 9.89 (s, 1H), 11.70 (s, 1H)

Example 74: 1-(4-Fluoro-benzyl)-1H-pyrazole-4-carboxylic acid (5-chloro-1H-pyrrolo[2,3-b]pyridin-3-yl)-amide

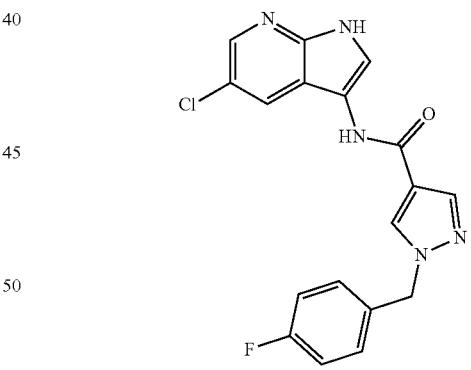

The title compound was prepared according to an analogous route to that outlined in Scheme 1, and using the methodology described for Example 73, in Step 1.

Step 2: Preparation of 5-chloro-1H-pyrrolo[2,3-b]pyridin-3-ylamine

Tin (II) chloride dihydrate (8.57 g, 38 mmol) was added in portions to a mixture of 5-chloro-3-nitro-1H-pyrrolo[2,3-b]pyridine (1.5 g, 7.59 mmol) in 6N HCl (60 mL) at 5° C. and the reaction was stirred at RT for 2 hours. The reaction mixture was cooled and diluted with H$_2$O (300 mL) then basified to pH8 by the careful addition of 50% aqueous NaOH solution. The mixture was then extracted with DCM/IPA (3:1, 4×150 mL) and the combined extracts were washed with saturated aqueous sodium chloride, dried (MgSO₄) and solvent removed in vacuo to afford the title compound as a green solid, 1.25 g, 98.2%.

Step 3: Preparation of title compound: 1-(4-fluoro-benzyl)-1H-pyrazole-4-carboxylic acid (5-chloro-1H-pyrrolo[2,3-b]pyridin-3-yl)-amide 5-Chloro-1H-pyrrolo[2,3-b]pyridin-3-ylamine (40.0 mg, 0.24 mmol) was stirred in DMF (3.0 mL), with Et₃N (0.07 mL, 0.48 mmol) and 1-(4-fluoro-benzyl)-1H-pyrazole-4-carboxylic acid (57.8 mg, 0.26 mmol), which was prepared in Example 17 HATU (91.3 mg, 0.24 mmol) was added and the reaction was stirred at RT for 2 hours. The reaction mixture was diluted with H₂O, and extracted with EtOAc (3×30 mL). The combined extracts were washed with saturated aqueous sodium bicarbonate, saturated aqueous sodium chloride (4×60 mL), dried (MgSO₄) and solvent removed in vacuo. The crude material was purified by automated column chromatography, eluting with DCM to 5% MeOH/DCM (gradient). Fractions containing pure product were combined and concentrated in vacuo to afford the title compound as a pale brown solid, 58.7 mg, 66.5%.

LC/MS: RT=2.23 Min (270 nm), m/z=370.3 [M+H]. Total run time 3.75 min (short pos/neg), HP1100.

¹H NMR (d₆ DMSO): δ 5.40 (s, 2H), 7.19-7.23 (m, 2H), 7.35-7.39 (m, 2H), 7.85 (d, 1H), 8.08 (s, 1H), 8.21 (d, 1H), 8.33 (d, 1H), 8.44 (s, 1H), 9.88 (s, 1H), 11.69 (br s, 1H)

Example 75: 1-(3-methoxy-benzyl)-1H-pyrazole-4-carboxylic acid (5-chloro-1H-pyrrolo[2,3-b]pyridin-3-yl)-amide

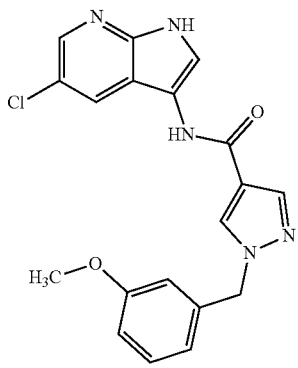 [SMILES: COc1cccc(Cn2cc(C(=O)Nc3c[nH]c4ncc(Cl)cc34)cn2)c1]

The title compound was prepared according to an analogous route to that outlined in Scheme 1, and using the methodology described for Example 74, substituting 1-(3-methoxy-benzyl)-1H-pyrazole-4-carboxylic acid (72.8 mg, 0.31 mmol) for 1-(4-fluoro-benzyl)-1H-pyrazole-4-carboxylic acid in Step 3. The title compound was isolated as a white solid, 24 mg, 21.1% following trituration with EtOAc.

LC/MS: RT=2.42 Min (254 nm), m/z=382 [M+H]. Total run time 3.75 min (short pos/neg), HP1100.

¹H NMR (d₆ DMSO): δ 3.75 (s, 3H), 5.38 (s, 2H), 6.88 (m, 3H), 7.30 (t, 7.83, 1H), 7.87 (s, 1H), 8.09 (s, 1H), 8.23 (s, 1H), 8.35 (s, 1H), 8.44 (s, 1H), 9.88 (s, 1H), 11.71 (s, 1H)

Example 76: 1-Benzyl-1H-pyrazole-4-carboxylic acid {6-[3-((S)-1-methyl-pyrrolidin-2-ylmethoxy)-phenyl]-1H-pyrrolo[2,3-b]pyridin-3-yl}-amide

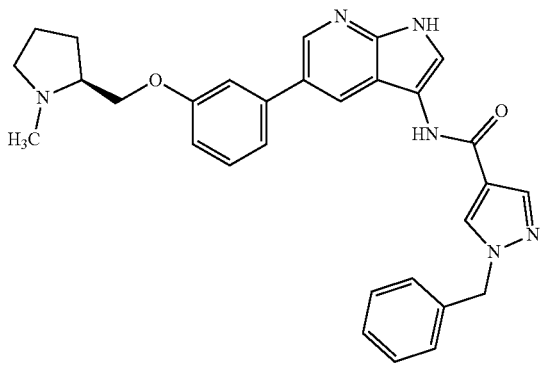 [SMILES: CN1CCC[C@H]1COc1cccc(-c2cnc3[nH]cc(NC(=O)c4cnn(Cc5ccccc5)c4)c3c2)c1]

The title compound was prepared according an analogous route to that outlined in Scheme 6.

The title compound was prepared from 1-benzyl-1H-pyrazole-4-carboxylic acid [5-bromo-1-(toluene-4-sulfonyl)-1H-pyrrolo[2,3-b]pyridin-3-yl]-amide, the product of Step 1 in Example 43.

Step 1: Preparation of (S)-1-methyl-2-[3-(4,4,5,5-tetramethyl-[1,3,2]dioxaborolan-2-yl)-phenoxymethyl]-pyrrolidine To a solution of 4-3-(4,4,5,5-tetramethyl-[1,3,2]dioxaborolan-2-yl)-phenol (150 mg, 0.68 mmol), (S)-(−)-1-methyl-2-pyrrolidineMeOH (117.8 mg, 1.02 mmol) and triphenylphosphine (268.2 mg, 1.02 mmol) in THF (3 mL) was added DIAD (206.7 mg, 2 mL, 1.02 mmol) drop wise at 0° C. The resulting solution was stirred at room temperature for 36 hours and the reaction mixture concentrated in vacuo. The crude material was purified by automated column chromatography eluting iso-hexane to 50% EtOAc/iso-hexane (gradient). The title compound was isolated as a white solid, 220 mg, 100%.

Step 2-Preparation of title compound: 1-Benzyl-1H-pyrazole-4-carboxylic acid {5-[3-((S)-1-methyl-pyrrolidin-2-ylmethoxy)-phenyl]-1H-pyrrolo[2,3-b]pyridin-3-yl}-amide 1-benzyl-1H-pyrazole-4-carboxylic acid [5-bromo-1-(toluene-4-sulfonyl)-1H-pyrrolo[2,3-b]pyridin-3-yl]-amide (115 mg, 0.21 mmol), (S)-1-methyl-2-[3-(4,4,5,5-tetramethyl-[1,3,2]dioxaborolan-2-yl)-phenoxymethyl]-pyrrolidine (99.4 mg, 0.31 mmol), potassium carbonate (86.6 mg, 0.63 mmol), THF (4 mL) and H₂O (0.4 mL) were combined in a microwave vial. The mixture was degassed, Pd(dppf)Cl₂ (7.64 mg, 0.01 mmol) added and the reaction heated at 130° C. for 1 hour under microwave irradiation. The reaction mixture was diluted with DCM and washed with saturated aqueous sodium chloride. The organics were separated, dried (MgSO₄) and concentrated in vacuo. The crude material was purified via automated column chromatography eluting with DCM to 10% MeOH/DCM (gradient) This afforded a mixture of two compounds, 1-benzyl-1H-pyrazole-4-carboxylic acid [5-[3-((S)-1-methyl-pyrrolidin-2-yl-methoxy)-phenyl]-1-(toluene-4-sulfonyl)-1H-pyrrolo[2,3-b]pyridin-3-yl]-amide and 1-benzyl-1H-pyrazole-4-carboxylic acid [5-[3-(1-methyl-piperidin-3-yloxy)-phenyl]-1-(toluene-4-sulfonyl)-1H-pyrrolo[2,3-b]pyridin-3-yl]-amide as a brown glass. This was taken up in MeOH (5 mL) and transferred to a microwave vial. $K_2CO_3$ (100.9 mg, 0.73 mmol) was added and the contents heated at 80° C. for 30 minutes under microwave irradiation. The reaction mixture was concentrated in vacuo to one quarter of volume and diluted with $H_2O$. Upon standing a precipitate formed, which was filtered off and washed with $H_2O$ and then $Et_2O$. The powder was dried and purified via automated column chromatography eluting with DCM to 19% MeOH/DCM (gradient), to give the title compound as a white powder, 7 mg, 6.6%. Example 77 (below), 1-benzyl-1H-pyrazole-4-carboxylic acid {5-[3-(1-methyl-piperidin-3-yloxy)-phenyl]-1H-pyrrolo[2,3-b]pyridin-3-yl}-amide, was also isolated from the same column as a solid, 8 mg, 7.6%.

LC/MS: RT=1.00 Min (230 nm), m/z=507 [M+H]. Total run time 1.9 min (super short pos), HP1200.

$^1$H NMR ($d_6$ DMSO): δ 1.62-1.81 (m, 3H), 1.96-2.08 (m, 1H), 2.96-3.12 (m, 1H), 3.9-4.15 (m, 2H), 5.42 (s, 2H), 6.93-6.98 (m, 1H), 7.22-7.42 (m, 8H), 7.82-7.85 (m, 1H), 8.10 (s, 1H), 8.48 (s, 1H), 8.51-8.57 (m, 2H), 9.92 (br s, 1H), 11.51 (br s, 1H) 5 protons not seen Example 77: 1-Benzyl-1H-pyrazole-4-carboxylic acid {5-[3-(1-methyl-piperidin-3-yloxy)-phenyl]-1H-pyrrolo[2,3-b]pyridin-3-yl}-amide

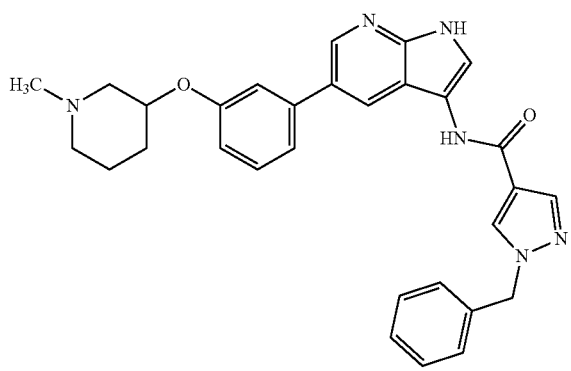 [SMILES: CN1CCCC(Oc2cccc(-c3cnc4[nH]cc(NC(=O)c5cnn(Cc6ccccc6)c5)c4c3)c2)C1]

The title compound was isolated from the crude reaction mixture as described in Example 76, Step 2, as a solid, 8 mg, 7.6%.

LC/MS: RT=1.00 Min (230 nm), m/z=507 [M+H]. Total run time 1.9 min (super short pos), HP1200.

$^1$H NMR ($d_6$ DMSO): δ 1.31-1.42 (m, 1H), 1.50-1.62 (s, 1H), 1.67-1.76 (m, 1H), 1.95-2.10 (m, 3H), 2.19 (s, 3H), 2.86-2.92 (m, 1H), 4.46-4.54 (m, 1H), 5.41 (s, 2H), 6.94-6.98 (m, 1H), 7.22-7.41 (m, 8H), 7.82-7.84 (d, 1H), 8.10 (s, 1H), 8.48 (s, 1H), 8.51-8.55 (m, 2H), 9.91 (br s, 1H), 11.50 (br s, 1H) 1 proton not seen Example 78: 1-Benzyl-1H-pyrazole-4-carboxylic acid {5-[4-(3-dimethylamino-propoxy)-phenyl]-1H-pyrrolo[2,3-b]pyridin-3-yl}-amide

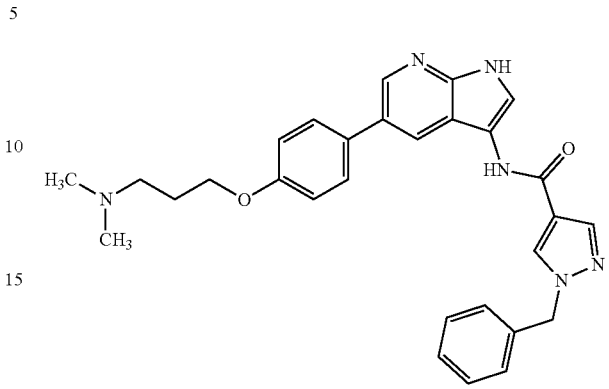

The title compound was prepared from 1-benzyl-1H-pyrazole-4-carboxylic acid [5-bromo-1-(toluene-4-sulfonyl)-1H-pyrrolo[2,3-b]pyridin-3-yl]-amide, the product of Step 1 in Example 43.

Step 1: Preparation of 1-Benzyl-1H-pyrazole-4-carboxylic acid [5-(4-hydroxy-phenyl)-1-(toluene-4-sulfonyl)-1H-pyrrolo[2,3-b]pyridin-3-yl]-amide 1-Benzyl-1H-pyrazole-4-carboxylic acid [5-bromo-1-(toluene-4-sulfonyl)-1H-pyrrolo[2,3-b]pyridin-3-yl]-amide (1.0 g, 1.82 mmol), 4-hydroxyphenylboronic acid (0.3 g, 2.18 mmol) and $K_2CO_3$ (0.75 g, 5.45 mmol) were combined in THF/$H_2O$ (14 mL:1.4 mL) and thoroughly degassed. Pd(dppf)$Cl_2$ (0.067 mg, 0.09 mmol) was added and the mixture degassed again before heating at 12000 for 1 hour under microwave irradiation, 4-Hydroxyphenylboronic acid (0.15 g, 1.09 mmol) was added and the mixture degassed again before heating at 120° C. for 2 hours and at 140° C. for 1 hour under microwave irradiation. The reaction was diluted with saturated aqueous sodium hydrogen bicarbonate (100 mL) and extracted with EtOAc (2×100 mL). The combined organics were washed with saturated aqueous sodium chloride, dried (MgSO$_4$) and solvent removed in vacuo. The crude material was purified by flash chromatography, eluting with DCM to 50% EtOAc/DCM (gradient). Fractions found to contain product were combined and solvent removed in vacuo. The residue was triturated using the minimum amount of ethanol to afford the desired compound as a as a white solid, 0.33 g, 32.6%.

Step 2: Preparation of: 1-Benzyl-1H-pyrazole-4-carboxylic acid [5-[4-(3-dimethylamino-propoxy)-phenyl]-1-(toluene-4-sulfonyl)-1H-pyrrolo[2,3-b]pyridin-3-yl]-amide 1-Benzyl-1H-pyrazole-4-carboxylic acid [5-bromo-1-(toluene-4-sulfonyl)-1H-pyrrolo[2,3-b]pyridin-3-yl]-amide (100 mg, 0.18 mmol) was stirred in DMF (4 mL) with $K_2CO_3$ (73.6 mg, 0.53 mmol). To this was added (3-chloropropyl)-dimethylamine hydrochloride (36.5 mg, 0.23 mmol)

and the reaction was then heated at 50° C. for 16 hours. The reaction was then cooled, concentrated in vacuo, and the residue partitioned between saturated aqueous sodium hydrogen carbonate (30 mL) and EtOAc (40 mL). The organics were separated and the aqueous extracted with another portion of EtOAc (40 mL). The combined organics were washed with saturated aqueous sodium chloride, dried over MgSO$_4$ and concentrated in vacuo. The crude material was purified by flash chromatography eluting with DCM then 10% MeOH/DCM and finally 6% ammonia solution, 7N in MeOH/EtOAc. The fractions containing product were combined and concentrated in vacuo to afford the title compound as a yellow solid, 67 mg, 58.2%.

Step 3. Preparation of title compound: 1-Benzyl-1H-pyrazole-4-carboxylic acid {5-[4-(3-dimethyl-amino-propoxy)-phenyl]-1H-pyrrolo[2,3-b]pyridin-3-yl}-amide 1-Benzyl-1H-pyrazole-4-carboxylic acid [5-[4-(3-dimethylamino-propoxy)-phenyl]-1-(toluene-4-sulfonyl)-1H-pyrrolo[2,3-b]pyridin-3-yl]-amide (67 mg, 0.10 mmol), K$_2$CO$_3$ (71.4 mg, 0.52 mmol) and MeOH (2 mL) were combined in a microwave vial and heated at 100° C. for 30 minutes. The mixture was concentrated in vacuo and the crude material was purified by preparative HPLC at pH 9 and then at pH 4 to afford the title compound as a pale orange solid, 0.8 mg, 1.6%.

LC/MS: RT=1.98 Min (254 nm), m/z=495 [M+H]. Total run time 3.75 min (short pos/neg). HP1100.

$^1$H NMR (d$_6$ DMSO): δ 1.87 (m, 2H), 2.16 (s, 6H), 2.37 (t, 2H), 4.04 (t, 2H), 5.41 (s, 2H), 7.04 (m, 2H), 7.27-7.41 (m, 5H), 7.62 (m, 2H), 7.80 (d, 1H), 8.10 (s, 1H), 8.40 (br s, 1H), 8.43-8.50 (m, 3H), 9.92 (s, 1H), 11.45 (d, 1H)

Example 79: 1-Benzyl-1H-pyrazole-4-carboxylic acid {5-[1-(2-diethylamino-ethyl)-1H-pyrazol-4-yl]-1H-pyrrolo[2,3-b]pyridin-3-yl}-amide

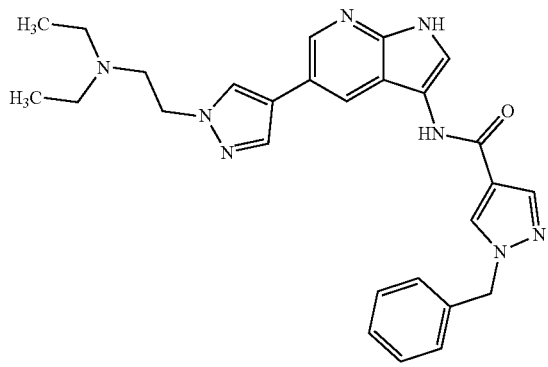 [SMILES: CCN(CC)CCn1cc(-c2cnc3[nH]cc(NC(=O)c4cnn(Cc5ccccc5)c4)c3c2)cn1]

The title compound was prepared according to the route outlined in Scheme 6. The title compound was prepared from 1-benzyl-1H-pyrazole-4-carboxylic acid [5-(4,4,5,5-tetramethyl-[1,3,2]dioxaborolan-2-yl)-1-(toluene-4-sulfonyl)-1H-pyrrolo[2,3-b]pyridin-3-yl]-amide, the product of Step 1 in Example 60.

Step 1: Preparation of [2-(4-Bromo-pyrazol-1-yl)-ethyl]-diethyl-amine

Cs$_2$CO$_3$ (1.66 g, 5.1 mmol) was added to a solution of 4-bromopyrazole (0.25 g, 1.7 mmol) in DMF (2 mL) and the mixture stirred for 10 minutes, 2-Bromo-N,N-diethylethyl-amine hydrobromide (0.577 g, 2.21 mmol) was added and the reaction heated at 70° C. 18 hours. The reaction was diluted with H$_2$O and extracted with DCM/IPA (4:1) (×2). The organics were combined, washed with saturated aqueous sodium chloride (×4), dried (MgSO4) and concentrated in vacuo to afford the title compound as a pale yellow oil, 275 mg, 65.7%.

Step 2: Preparation of 1-benzyl-1H-pyrazole-4-carboxylic acid [5-[1-(2-diethylamino-ethyl)-1H-pyrazol-4-yl]-1-(toluene-4-sulfonyl)-1H-pyrrolo[2,3-b]pyridin-3-yl]-amide 1-Benzyl-1H-pyrazole-4-carboxylic acid [5-(4,4,5,5-tetramethyl-[1,3,2]dioxaborolan-2-yl)-1-(toluene-4-sulfonyl)-1H-pyrrolo[2,3-b]pyridin-3-yl]-amide (90 mg, 0.15 mmol), [2-(4-Bromo-pyrazol-1-yl)-ethyl]-diethyl-amine (74.2 mg, 0.3 mmol), K$_2$CO$_3$) 62.5 mg, 0.45 mmol) THF (4 mL) and H$_2$O (0.4 mL) were combined in a microwave vial and degassed. Pd(dppf)Cl$_2$ (5.5 mg, 0.01 mmol) was added and the contents degassed again before heating at 130° C. for 1 hour under microwave irradiation. The mixture was degassed and a further portion of Pd(dppf)Cl$_2$ (5.5 mg, 0.01 mmol) was added and degassed before heating at 130° C. for 30 minutes. The reaction mixture was diluted with DCM and the organics separated. The aqueous was extracted with another portion of DCM and the combined organics were washed with saturated aqueous sodium chloride, dried over MgSO$_4$ and concentrated in vacuo. The crude material was purified by automated column chromatography eluting with DCM to 15% MeOH/DCM (gradient) to afford the title compound, 24 mg, 25.1%.

Step 3-Preparation of title compound: 1-Benzyl-1H-pyrazole-4-carboxylic acid {5-[1-(2-diethylamino-ethyl)-1H-pyrazol-4-yl]-1H-pyrrolo[2,3-b]pyridin-3-yl}-amide 1-Benzyl-1H-pyrazole-4-carboxylic acid [5-(4,4,5,5-tetramethyl-[1,3,2]dioxaborolan-2-yl)-1-(toluene-4-sulfonyl)-1H-pyrrolo[2,3-b]pyridin-3-yl]-amide (90 mg, 0.15 mmol). [2-(4-Bromo-pyrazol-1-yl)-ethyl]-diethyl-amine (24 mg, 0.038 mmol), K$_2$CO$_3$ (104.1 mg, 0.75 mmol) and MeOH (3 mL) were combined in a microwave vial and heated at 80° C. for 30 minutes. The reaction mixture was concentrated in vacuo to one quarter volume and diluted with H$_2$O. After standing for 2 hrs the solid was separated via filtration, washed with H$_2$O then Et$_2$O and dried in vacuo to afford the title compound as a grey powder, 7 mg, 38.2%.

LC/MS: RT=0.92 Min (230 nm), m/z=483 [M+H]. Total run time 1.9 min (super short pos), HP1200.

$^1$H NMR (d$_6$ DMSO): δ 0.90-0.95 (t, 6H), 2.79-2.84 (t, 2H), 4.14-4.19 (t, 2H), 5.41 (s, 2H), 7.28-7.41 (m, 5H), 7.72 (s, 1H), 7.85 (s, 1H), 8.09 (s, 1H), 8.16 (s, 1H), 8.27-8.30 (m, 1H), 8.45-8.49 (m, 2H), 9.86 (br s, 1H), 11.39 (br s, 1H) 4 protons not seen

Example 80: 1-Benzyl-1H-pyrazole-4-carboxylic acid {5-[1-(2-pyrrolidin-1-yl-ethyl)-1H-pyrazolo-4-yl]-1H-pyrrolo[2,3-b]pyridin-3-yl}-amide

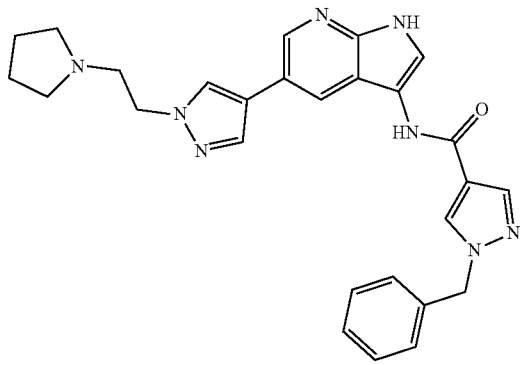 [SMILES: O=C(Nc1c[nH]c2ncc(-c3cnn(CCN4CCCC4)c3)cc12)c1cnn(Cc2ccccc2)c1]

The title compound was prepared according to the route outlined in Scheme 6, and using the methodology described for Example 79, substituting 1-(2-chloro-ethyl)-pyrrolidine hydrochloride (376.1 mg, 2.21 mmol) for 2-bromo-N,N-diethylethylamine hydrobromide in Step 1. The title compound was isolated as a dark powder, 10 mg, 13.8%.

LC/MS: RT=1.15 Min (230 nm), m/z=481 [M+H]. Total run time 1.9 min (super short pos), HP1200.

$^1$H NMR (d$_6$ DMSO): δ 1.63-1.69 (m, 4H), 2.83-2.88 (t, 2H), 4.21-4.26 (t, 2H), 5.41 (s, 2H), 7.28-7.41 (m, 5H), 7.72 (s, 1H), 7.84-7.86 (s, 1H), 8.09 (s, 1H), 8.18 (s, 1H) 8.28-8.31 (m, 1H), 8.45-8.49 (m, 2H), 9.87 (br s, 1H), 11.40 (br s, 1H) 4 protons not seen

Example 81: 1-Pyridin-4-ylmethyl-1H-pyrazole-4-carboxylic acid [4-((R)-3-amino-piperidin-1-yl)-5-methoxy-1H-pyrrolo[2,3-b]pyridin-3-yl]-amide

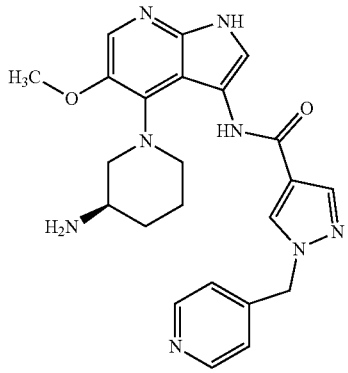 [SMILES: COc1cnc2[nH]cc(NC(=O)c3cnn(Cc4ccncc4)c3)c2c1N1CCC[C@@H](N)C1]

The title compound was prepared according to an analogous route to that outlined in Scheme 2.

It was prepared from 4-fluoro-5-methoxy-1H-pyrrolo[2,3-b]pyridin-3-ylamine, the product of Step 7, in Example 31.

Step 1: Preparation of 1-pyridin-4-ylmethyl-1H-pyrazole-4-carboxylic acid 4-bromomethyl pyridine hydrochloride (3.58 g, 14.17 mmol) was added to a suspension of ethyl 1H-pyrazole-4-carboxylate (1.89 g, 14.17 mmol) and cesium carbonate (10.43 g, 32 mmol) in acetone (50 mL), under a nitrogen atmosphere, and the suspension stirred for 18 hours at RT. The reaction was diluted with H$_2$O and then extracted with EtOAc (×2). The combined extracts were washed with H$_2$O, saturated aqueous sodium chloride solution, dried (MgSO$_4$) and concentrated in vacuo. The residue was stirred in MeOH (50 mL) and a solution of sodium hydroxide (0.896 g, 22.4 mmol) H$_2$O (15 mL) was added. The reaction mixture was heated at reflux for 3 hours and then cooled to RT The solvent was removed in vacuo and the residue diluted with a little H$_2$O. The pH of the mixture was adjusted to 4 by the careful addition of aqueous hydrochloric acid solution, 1.0M. After stirring for 10 mins the solids were separated via filtration, washed well with H$_2$O and dried in vacuo to yield the desired title compound as a solid, 0.449 g. The filtrate was extracted with EtOAc (×6) and combined extracts were washed with saturated aqueous sodium chloride, dried over MgSO$_4$ and concentrated in vacuo to furnish a further crop of the title compound, 0.736 g.

This gave a total of 1.185 g, 78%.

Step 2: Preparation of 1-pyridin-4-ylmethyl-1H-pyrazole-4-carboxylic acid (5-chloro-4-fluoro-1H-pyrrolo[2,3-b]pyridin-3-yl)-amide 4-fluoro-5-methoxy-1H-pyrrolo[2,3-b]pyridin-3-ylamine (97 mg, 0.54 mmol) was stirred in DMF (5 mL). Et$_3$N 109 mg, 150 uL, 1.08 mmol) and 1-pyridin-4-ylmethyl-1H-pyrazole-4-carboxylic acid (119.7 mg, 0.59 mmol) were added followed by HATU (224.3 mg, 0.54 mmol). The reaction was stirred at RT for 18 hrs and then diluted with H$_2$O (20 mL). The solution was extracted with EtOAc (2×50 mL) and 10% MeOH in DCM (2×50 mL). The combined organic extracts were dried over MgSO$_4$ and concentrated in vacuo. The residue was triturated with EtOAc to give the title compound as a pale brown solid 125 mg, 63.7%.

Step 3: Preparation of title compound: 1-pyridin-4-ylmethyl-1H-pyrazole-4-carboxylic acid [4-((R)-3-amino-piperidin-1-yl)-5-methoxy-1H-pyrrolo[2,3-b]pyridin-3-yl]-amide 1-pyridin-4-ylmethyl-1H-pyrazole-4-carboxylic acid (5-chloro-4-fluoro-1H-pyrrolo[2,3-b]pyridin-3-yl)-amide (125 mg, 0.34 mmol), (R)-piperidin-3-yl-carbamic acid tert-butyl ester (341.7 mg, 1.71 mmol) and "BuOH (5 mL) were combined in a microwave vial and heated under microwave irradiation at 160° C. for 6 hours. The solvent was removed in vacuo and the residue was taken up in DCM (5 mL). TFA (3 mL) was added and the reaction mixture was stirred at RT for 18 hrs. The reaction was concentrated in vacuo and taken up in DCM prior to loading onto a SCX-2 ion exchange column. The column was washed with DCM, MeOH and the compound of interest was eluted with ammonia solution 7 N in MeOH that had been diluted to 0.5N using DCM. Fractions containing product were combined and concentrated in vacuo. The material was further purified by automated column chromatography eluting with DCM to 5% ammonia solution 7N in MeOH/5% MeOH/DCM. The fractions containing pure product were combined and concentrated in vacuo to afford the title compound as a pale orange solid 22 mg, 14%.

LC/MS: RT=1.35 Min (270 nm), m/z=447 [M+H]. Total run time 3.75 min (short pos), HP1100.

$^1$H NMR (d$_6$ DMSO): δ 1.18 (m, 1H), 1.44-1.76 (m, 5H), 2.85 (m, 2H), 3.03 (m, 2H), 3.21 (d, 1H), 3.86 (s, 3H), 5.50 (s, 2H), 7.16 (m, 2H), 7.71 (s, 1H), 8.06 (m, 2H), 8.55 (m, 2H), 8.63 (s, 1H), 9.76 (br s, 1H), 11.22 (br s, 1H)

Example 82: 1-Pyridin-3-ylmethyl-1H-pyrazole-4-carboxylic acid [4-((R)-3-amino-piperidin-1-yl)-5-methoxy-1H-pyrrolo[2,3-b]pyridin-3-yl]-amide

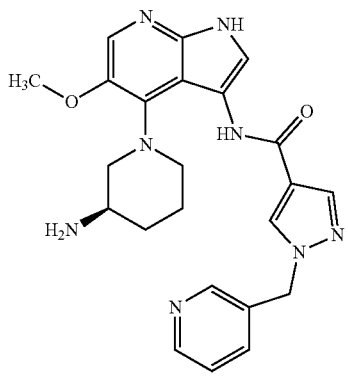 [SMILES: COc1cnc2[nH]cc(NC(=O)c3cnn(Cc4cccnc4)c3)c2c1N1CCC[C@@H](N)C1]

The title compound was prepared according to an analogous route to that outlined in Scheme 2, and using the methodology described for Example 81, substituting 1-pyridin-3-ylmethyl-1H-pyrazole-4-carboxylic acid (119.7 mg, 0.59 mmol) for 1-pyridin-4-ylmethyl-1H-pyrazole-4-carboxylic acid in Step 1. The title compound was isolated as an off white solid, 48 mg, 26.6%.

LC/MS: RT=1.50 Min (270 nm), m/z=447 [M+H]. Total run time 3.75 min (short pos). HP1100.

$^1$H NMR (d$_6$ DMSO): δ 1.2 (m, 1H), 1.41-1.75 (m, 5H), 2.85 (m, 2H), 3.03 (t, 2H), 3.21 (d, 1H), 3.86 (s, 3H), 5.47 (s, 2H), 7.40 (dd, 1H), 7.67-7.72 (m, 2H), 8.04 (m, 2H), 8.52-8.62 (m, 3H), 9.74 (br s, 1H), 11.20 (br s, 1H)

Example 83: 1-Pyridin-2-ylmethyl-1H-pyrazole-4-carboxylic acid [4-((R)-3-amino-piperidin-1-yl)-5-methoxy-1H-pyrrolo[2,3-b]pyridin-3-yl]-amide

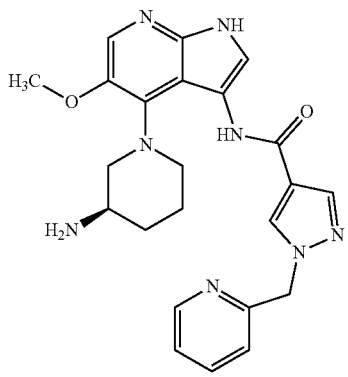 [SMILES: COc1cnc2[nH]cc(NC(=O)c3cnn(Cc4ccccn4)c3)c2c1N1CCC[C@@H](N)C1]

The title compound was prepared according to an analogous route to that outlined in Scheme 2, and using the methodology described for Example 81, substituting 1-pyridin-2-ylmethyl-1H-pyrazole-4-carboxylic acid (119.7 mg, 0.59 mmol) for 1-pyridin-4-ylmethyl-1H-pyrazole-4-carboxylic acid in Step 1. The title compound was isolated as an off white solid, 56 mg, 34%.

LC/MS: RT=1.60 Min (270 nm), m/z=447 [M+H]. Total run time 3.75 min (short pos), HP1100.

$^1$H NMR (d$_6$ DMSO): δ 1.2 (m, 1H), 1.48-1.77 (m, 5H), 2.86 (m, 2H), 3.05 (m, 2H), 3.21 (d, 1H), 3.86 (s, 3H), 5.52 (s, 2H), 7.14 (d, 1H), 7.33 (dd, 1H), 7.74 (s, 1H), 7.81 (t, 1H), 8.02 (s, 1H), 8.07 (s, 1H), 8.56 (m, 2H), 9.78 (br s, 1H), 11.21 (br s, 1H)

Example 84: 1-Pyridin-3-ylmethyl-1H-pyrazole-4-carboxylic acid [4-((R)-amino-piperidin-1-yl)-5-chloro-1H-pyrrolo[2,3-b]pyridin-3-yl]-amid

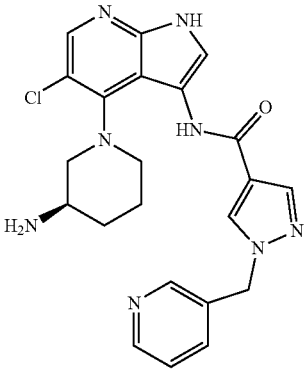

The title compound was prepared according to an analogous route to that outlined in Scheme 2, using the methodology described for Example 24, substituting 1-pyridin-3-ylmethyl-1H-pyrazole-4-carboxylic acid (344.5 mg, 1.7 mmol) for 1-benzyl-1H-pyrazole-4-carboxylic acid in Step 6. After the usual work up as described in Step 7, the crude material was taken up in DCM and loaded onto a SCX-2 ion exchange column. The column was washed with DCM, MeOH and the compound of interest was eluted with ammonia solution 7 N in MeOH that had been diluted to 0.5N using DCM. Fractions containing product were combined and concentrated in vacuo. The residue was further purified by automated column chromatography eluting with 2% Et$_3$N in DCM to 20% MeOH/2% Et$_3$N in DCM (gradient). Fractions containing pure material were combined and concentrated in vacuo to afford the title compound as a pale yellow solid, 52 mg, 21.4%.

LC/MS: RT=1.59 Min (270 nm), m/z=451 [M+H]. Total run time 3.75 min (short pos), HP1100.

$^1$H NMR (d$_6$ DMSO): δ 1.19 (m, 2H), 1.46 (m, 1H), 1.69 (m, 2H), 2.92 (m, 2H), 3.12 (m, 2H), 5.48 (s, 2H), 7.40 (dd, 1H), 7.67-(dt, 1H), 7.71 (s, 1H), 8.06 (s, 1H), 8.08 (s, 1H), 8.52-8.58 (m, 3H), 973 (br s, 1H), 11.69 (br s, 1H) 2 protons not seen

Example 85: 1-Pyridin-4-ylmethyl-1H-pyrazole-4-carboxylic acid [4-((R)-3-amino-piperidin-1-yl)-5-chloro-1H-pyrrolo[2,3-b]pyridin-3-yl]-amide

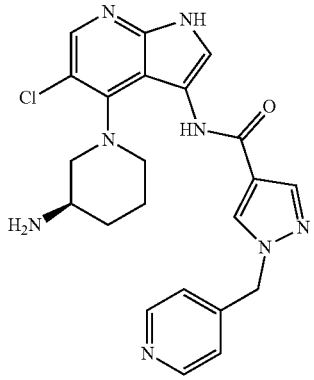 [SMILES: N[C@@H]1CCCN(c2c(Cl)cnc3[nH]cc(NC(=O)c4cnn(Cc5ccncc5)c4)c23)C1]

The title compound was prepared according to an analogous route to that outlined in Scheme 2, using the methodology described for Example 24, substituting 1-pyridin-3-ylmethyl-1H-pyrazole-4-carboxylic acid (344.5 mg, 1.7 mmol) for 1-benzyl-1H-pyrazole-4-carboxylic acid in Step 6. After the usual work up as described in Step 7, the crude material was taken up in DCM and loaded onto a SCX-2 ion exchange column. The column was washed with DCM, MeOH and the compound of interest was eluted with ammonia solution 7 N in MeOH that had been diluted to 0.5N using DCM. Fractions containing product were combined and concentrated in vacuo. The residue was further purified by automated column chromatography eluting with DCM to 12% MeOH/DCM (gradient). Fractions containing product were combined and concentrated in vacuo. The residue was further purified by preparative HPLC at pH4. Fractions containing pure material were combined and concentrated in vacuo to afford a mixture of desired compound and 1-pyridin-4-ylmethyl-1H-pyrazole-4-carboxylic acid [5-chloro-4-((R)-3-formylamino-piperidin-1-yl)-1H-pyrrolo[2,3-b]pyridin-3-yl]-amide. This material was stirred in the minimum amount of MeOH and then hydrochloric acid solution, 4M in 1,4-dioxane (2 mL) was added. The reaction was stirred at RT for 18 hours and the solvent was removed in vacuo. The residue was taken up in DCM, washed with 5% aqueous ammonia solution, dried (MgSO$_4$) and concentrated in vacuo. The residue was further purified by automated column chromatography eluting with 2% Et$_3$N in DCM to 20% MeOH/2% Et$_3$N in DCM (gradient). Fractions containing pure material were combined and concentrated in vacuo to afford the title compound as a pale yellow solid, 52 mg, 13.2%.

LC/MS: RT=1.52 Min (270 nm), m/z=451 [M+H]. Total run time 3.75 min (short pos), HP1100.

$^1$H NMR (d$_6$ DMSO): δ 1.19 (m, 2H), 1.48 (m, 1H), 1.69 (m, 2H), 2.25 (br s, 2H), 2.92 (m, 2H), 3.13 (m, 2H), 5.50 (s, 2H), 7.15 (m, 2H), 7.72 (s, 1H), 8.09 (m, 2H), 8.57 (m, 3H), 9.74 (br s, 1H), 11.71 (br s, 1H)

Example 86: 1-Pyridin-2-ylmethyl-1H-pyrazole-4-carboxylic acid [4-((R)-3-amino-piperidin-1-yl)-5-chloro-1H-pyrrolo[2,3-b]pyridin-3-yl]-amide

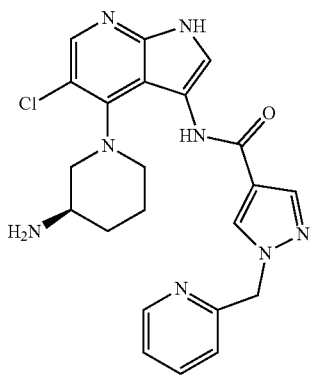 [SMILES: N[C@@H]1CCCN(c2c(Cl)cnc3[nH]cc(NC(=O)c4cnn(Cc5ccccn5)c4)c23)C1]

The title compound was prepared according to an analogous route to that outlined in Scheme 2, using the methodology described for Example 85, substituting 1-pyridin-2-ylmethyl-1H-pyrazole-4-carboxylic acid (344.5 mg, 1.7 mmol) for 1-benzyl-1H-pyrazole-4-carboxylic acid in Step 6. The title compound was isolated as a pale yellow solid, 30 mg, 12.3%.

LC/MS: RT=1.69 Min (270 nm), m/z=451 [M+H]. Total run time 3.75 min (short pos), HP1100.

$^1$H NMR (d$_6$ DMSO): δ 1.20 (m, 2H), 1.50 (m, 1H), 1.72 (m, 2H), 2.08 (br s, 2H), 2.92 (m, 2H), 3.15 (m, 2H), 5.52 (s, 2H), 7.13 (d, 1H), 7.37 (dd, 1H), 7.75 (s, 1H), 7.81 (m, 1H), 8.04 (s, 1H), 8.09 (s, 1H), 8.56 (m, 2H), 9.79 (br s, 1H), 11.68 (br s, 1H)

Example 87: 1-Pyridin-4-ylmethyl-1H-pyrazole-4-carboxylic acid [4-((R)-3-amino-piperidin-1-yl)-methyl-1H-pyrrolo[2,3-b]pyridin-3-yl]-amide

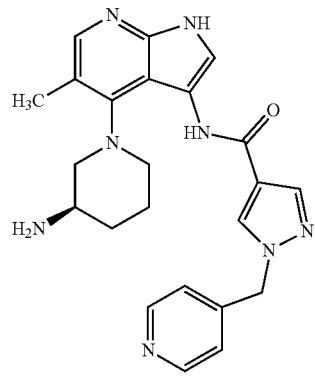 [SMILES: Cc1cnc2[nH]cc(NC(=O)c3cnn(Cc4ccncc4)c3)c2c1N1CCC[C@@H](N)C1]

The title compound was prepared according to an analogous route to that outlined in Scheme 2.

It was prepared from 4-fluoro-1-triisopropylsilanyl-1H-pyrrolo[2,3-b]pyridine, the product of Step 2, in Example 6.

Step 1: Preparation of 4-Fluoro-5-methyl-1H-pyrrolo[2,3-b]pyridine sec-Butyllithium solution, 1.4M in cyclohexane (8.76 mL, 12.26 mmol) was added drop wise to a solution of 4-fluoro-1-triisopropylsilanyl-1H-pyrrolo[2,3-b]pyridine (2.05 g, 7.01 mmol) in THF (75 mL) at −78° C. The reaction was stirred at −78° C. for 30 minutes and then methyl iodide (2.49 g, 1.09 mL, 17.52 mmol) was added drop wise and the reaction was stirred at −78° C. for a further 45 minutes. The reaction was quenched by the addition of saturated aqueous ammonium chloride (50 mL) and the reaction allowed to attain RT. The mixture was extracted with EtOAc (×3) and the combined extracts washed with saturated aqueous sodium chloride, dried (MgSO$_4$) and concentrated in vacuo. The residue was taken up in THF (50 mL) and tetrabutylammonium fluoride solution, 1.0M in THF (7.01 mL, 7.01 mmol) was added drop wise at RT. The reaction mixture was stirred at RT for 30 minutes and then partitioned between H$_2$O and EtOAc. The organic layer was separated and the aqueous was extracted with more EtOAc. The combined organic phases were washed with saturated aqueous sodium chloride, dried (MgSO$_4$) and concentrated in vacuo. The residue was stirred in DCM/iso-hexane (1:1), filtered and washed with DCM/iso-hexane (1:1) prior to drying in vacuo. This afforded the title compound as a white powder, 0.561 g, 53.3%.

Step 2: Preparation of 4-fluoro-5-methyl-3-nitro-1H-pyrrolo[2,3-b]pyridine

The title compound was prepared using the methodology described for Example 6, substituting 4-fluoro-5-methyl-1H-pyrrolo[2,3-b]pyridine (600 mg, 4 mmol) for 5-Bromo-4-fluoro-1H-pyrrolo[2,3-b]pyridine, in Step 5. The title compound was isolated as a pale yellow powder, 609 mg, 78.1%.

Step 3: Preparation of 4-fluoro-5-methyl-1H-pyrrolo[2,3-b]pyridin-3-ylamine

The title compound was prepared using the methodology described for Example 6, substituting 4-fluoro-5-methyl-3-nitro-1H-pyrrolo[2,3-b]pyridine (277 mg, 1.42 mmol) for 5-Bromo-4-fluoro-3-nitro-1H-pyrrolo[2,3-b]pyridine, in Step 6. The title compound was isolated as a brown powder, 230 mg, 98.1%.

Step 4: Preparation of 1-benzyl-1H-pyrazole-4-carboxylic acid (4-fluoro-5-methyl-1H-pyrrolo[2,3-b]pyridin-3-yl)-amide 4-Fluoro-5-methyl-1H-pyrrolo[2,3-b]pyridin-3-ylamine (230 mg, 1.39 mmol) was stirred in DMF (5 mL) with DIPEA (0.462 mL, 2.79 mmol) and 1-pyridin-4-ylmethyl-1H-pyrazole-4-carboxylic acid (270 mg, 1.33 mmol). HATU (582 mg, 153 mmol) was added and the reaction was stirred at RT for 2 hours. The reaction mixture was diluted with $H_2O$, and extracted with DCM/IPA (4:1) (×2). The combined extracts were washed with saturated aqueous sodium bicarbonate, saturated aqueous sodium chloride, dried ($MgSO_4$) and solvent removed in vacuo to afford a black residue. This was triturated with MeOH/$H_2O$ (1:1), filtered and washed with iso-hexane prior to drying in vacuo at 40° C. This afforded the title compound as a brown powder, 198 mg, 40.6%.

Step 5: Preparation of title compound: 1-pyridin-4-ylmethyl-1H-pyrazole-4-carboxylic acid [4-((R)-3-amino-piperidin-1-yl)-5-methyl-1H-pyrrolo[2,3-b]pyridin-3-yl]-amide 1-Benzyl-1H-pyrazole-4-carboxylic acid (4-fluoro-5-methyl-1H-pyrrolo[2,3-b]pyridin-3-yl)-amide (198 mg, 0.57 mmol), p-toluenesulfonic acid monohydrate (430 mg, 2.26 mmol), (R)-piperidin-3-yl-carbamic acid tert-butyl ester (565.9 mg, 2.83 mmol) and NMP (6 mL) were heated in a sealed tube at 160° C. for 7 hours. The mixture was purified by automated column chromatography eluting with DCM to 45% MeOH/DCM (gradient). The fractions containing product were combined and concentrated in vacuo. This still crude material was taken up in the minimum amount of DCM and $Et_3N$ (217.8 mg, 0.3 mL, 2.15 mmol) was added. The mixture was stirred at RT and di-tert-butyl dicarbonate (150 mg, 0.69 mmol) was added followed by DMAP (5 mg). This was stirred for 1 hour, diluted with DCM and washed with $H_2O$, saturated aqueous sodium chloride, dried ($MgSO_4$) and concentrated in vacuo. This crude material was purified via automated column chromatography eluting with DCM to 10% MeOH/DCM (gradient). The fractions containing the higher running mono boc product were combined and concentrated in vacuo. The residue was taken up in hydrochloric acid solution, 1.25M in MeOH (2 mL) and heated under microwave irradiation at 80° C. for 30 minutes. The solvent was removed in vacuo and residue taken up in minimum volume of MeOH and applied to a SCX-2 ion exchange cartridge. This was washed with MeOH and desired compound eluted with 4:1 DCM/7N $NH_3$ in MeOH and concentrated in vacuo. Acetonitrile was added to the residue and after sonication for 10 minutes a fine precipitate formed. This was pelleted in a centrifuge and, after the liquors were decanted off, the solids were washed with $Et_2O$ and filtered to give the title compound as a beige powder, 4.1 mgs, 1.7%.

LC/MS: RT=0.41 Min (230 nm), m/z=431 [M+H]. Total run time 1.9 min (super short pos), HP1200.

$^1$H NMR ($d_6$ DMSO): δ 1.11-1.22 (m, 1H), 1.43-1.54 (m, 1H) 1.64-1.77 (m, 2H), 2.36 (s, 3H), 2.78-2.85 (m, 1H), 2.85-2.93 (m, 1H), 3.00-3.05 (m, 2H), 3.17-3.24 (m, 1H), 5.51 (s, 2H), 7.13-7.16 (m, 2H), 7.68 (s, 1H), 7.93 (s, 1H), 8.07 (s, 1H), 8.54-8.57 (m, 2H), 8.59 (br s, 1H), 9.78 (br s, 1H), 11.28 (br s, 1H) 2 protons not seen

Example 88: 1-Pyridin-3-ylmethyl-1H-pyrazole-4-carboxylic acid [4-((R)-3-amino-piperidin-1-yl)-5-methyl-1H-pyrrolo[2,3-b]pyridin-3-yl]-amide

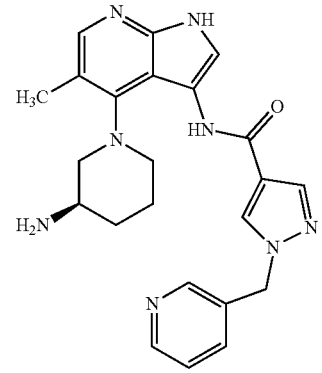 [SMILES: Cc1cnc2[nH]cc(NC(=O)c3cnn(Cc4cccnc4)c3)c2c1N1CCC[C@@H](N)C1]

The title compound was prepared using the methodology described for Example 87, substituting 1-pyridin-3-ylmethyl-1H-pyrazole-4-carboxylic acid (406 mg, 2 mmol) for 1-pyridin-4-ylmethyl-1H-pyrazole-4-carboxylic acid, in Step 4. It was isolated as a beige powder, 0.88 mgs, 0.63%.

LC/MS: RT=0.65 Min (230 nm), m/z=431 [M+H]. Total run time 1.9 min (super short pos), HP1200.

$^1$H NMR ($d_6$ DMSO): δ 1.11-1.23 (m, 1H), 1.40-1.52 (m, 1H) 1.63-1.77 (m, 2H), 2.36 (s, 3H), 2.77-2.85 (m, 1H), 2.85-2.94 (m, 1H), 2.99-3.06 (m, 2H), 3.16-3.25 (m, 1H), 5.47 (s, 2H), 7.38-7.44 (m, 1H), 7.65-7.70 (m, 2H), 7.93 (s, 1H), 8.03 (s, 1H), 8.51-8.62 (m, 3H), 9.76 (br s, 1H), 11.27 (br s, 1H) 2 protons not seen

Example 89: 1-(4-Fluoro-benzyl)-1H-pyrazole-4-carboxylic acid [4-((R)-3-amino-piperidin-1-yl)-5-methoxy-1H-pyrrolo[2,3-b]pyridin-3-yl]-amide

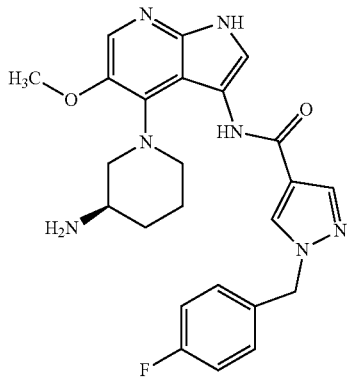 [SMILES: COc1cnc2[nH]cc(NC(=O)c3cnn(Cc4ccc(F)cc4)c3)c2c1N1CCC[C@@H](N)C1]

The title compound was prepared according to the route outlined in Scheme 7. It was made from [(R)-1-(3-amino-5-methoxy-1H-pyrrolo[2,3-b]pyridin-4-yl)-piperidin-3-yl]-carbamic acid tert-butyl ester, the product of Step 5, in Example 32.

Step 1: Preparation of [(R)-1-(3-{[1-(4-fluoro-benzyl)-1H-pyrazole-4-carbonyl]-amino}-5-methoxy-1H-pyrrolo[2,3-b]pyridin-4-yl)-piperidin-3-yl]-carbamic acid tert-butyl ester To a solution of [(R)-1-(3-amino-5-methoxy-1H-pyrrolo[2,3-b]pyridin-4-yl)-piperidin-3-yl]-carbamic acid tert-butyl ester (92 mg, 0.25 mmol), 1-(4-fluoro-benzyl)-1H-pyrazole-4-carboxylic acid (61.6 mg, 0.28 mmol) and Et$_3$N (69.6 µL, 0.5 mmol) in DMF (5 ml) was added HATU (95.1 mg, 0.25 mmol) and the reaction mixture was stirred at RT for 18 hours. The reaction mixture was concentrated in vacuo and the residue taken up in EtOAc (50 ml) It was washed with H$_2$O, saturated aqueous sodium chloride, dried (MgSO$_4$) and concentrated in vacuo. The crude material was purified by automated column chromatography eluting with 30% EtOAc/iso-hexane to EtOAc (gradient). Fractions containing pure product were combined and concentrated in vacuo to afford the title compound as a brown solid, 82 mg, 57.2%.

Step 2: Preparation of title compound: 1-(4-fluoro-benzyl)-1H-pyrazole-4-carboxylic acid [4-((R)-3-amino-piperidin-1-yl)-5-methoxy-1H-pyrrolo[2,3-b]pyridin-3-yl]-amide To a solution of ((R)-1-{3-[(1-benzyl-1H-pyrazole-4-carbonyl)-amino]-5-methoxy-1H-pyrrolo[2,3-b]pyridin-4-yl}-piperidin-3-yl)-carbamic acid tert-butyl ester (81 mg, 0.14 mmol) in DCM (5 mL) was added TFA (1 mL) at RT. The reaction mixture was stirred for a further 2 hours at RT and then concentrated in vacuo. The residue was taken up in DCM, washed with 5% aqueous ammonia solution, saturated aqueous sodium chloride, dried (MgSO$_4$) and concentrated in vacuo. The crude material was purified by automated column chromatography eluting with DCM to 20% MeOH (containing 5% 7N NH$_3$ in MeOH) (gradient). Fractions containing pure product were combined and concentrated in vacuo to afford the title compound as a white solid, 34 mg, 51%.

LC/MS: RT=1.81 Min (270 nm), m/z=464 [M+H]. Total run time 3.75 min (short pos), HP1100.

$^1$H NMR (d$_6$ DMSO): δ 1.18 (m, 1H), 1.45-1.71 (m, 5H), 2.85 (m, 2H), 3.03 (m, 2H), 3.21 (d, 1H), 3.86 (s, 3H), 5.40 (s, 2H), 7.21 (m, 2H), 7.34 (m, 2H), 7.72 (s, 1H), 8.01 (s, 1H), 8.06 (s, 1H), 8.55 (s, 1H), 9.73 (br s, 1H), 11.21 (br s, 1H)

Example 90: 1-(3-Methyl-benzyl)-1H-pyrazole-4-carboxylic acid [4-((R)-3-amino-piperidin-1-yl-5-methoxy-1H-pyrrolo[2,3-b]pyridin-3-yl]-amide

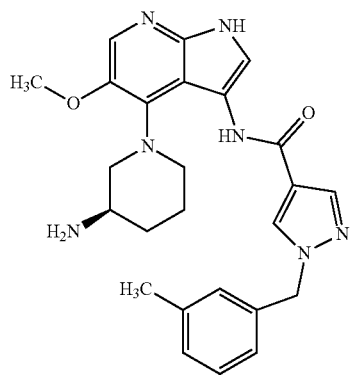 [SMILES: COc1cnc2[nH]cc(NC(=O)c3cnn(Cc4cccc(C)c4)c3)c2c1N1CCC[C@@H](N)C1]

The title compound was prepared according to the route outlined in Scheme 7, using the methodology described for Example 89, substituting 1-(3-methyl-benzyl)-1H-pyrazole-4-carboxylic acid (79 mg, 0.365 mmol) for 1-(4-fluoro-benzyl)-1H-pyrazole-4-carboxylic acid, in Step 1. The title compound was isolated as a white solid, 59 mg, 64.7%.

LC/MS: RT=1.86 Min (270 nm), m/z=460 [M+H]. Total run time 3.75 min (short pos), HP1100.

$^1$H NMR (d$_6$ DMSO): δ 1.19 (m, 1H), 1.44-1.75 (m, 5H), 2.29 (s, 3H), 2.85 (m, 2H), 3.03 (t, 2H), 3.21 (d, 1H), 3.86 (s, 3H), 5.36 (s, 2H), 7.07-7.14 (m, 3H), 7.26 (t, 1H), 7.73 (s, 1H), 8.00 (s, 1H), 8.06 (s, 1H), 8.55 (s, 1H), 9.74 (br s, 1H), 11.20 (br s, 1H)

Example 91: 1-(3-Fluoro-benzyl)-1H-pyrazole-4-carboxylic acid [4-((R)-3-amino-piperidin-1-yl)-5-methoxy-1H-pyrrolo[2,3-b]pyridin-3-yl]-amide

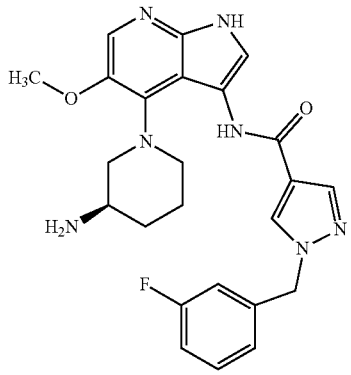 [SMILES: COc1cnc2[nH]cc(NC(=O)c3cnn(Cc4cccc(F)c4)c3)c2c1N1CCC[C@@H](N)C1]

The title compound was prepared according to the route outlined in Scheme 7, using the methodology described for Example 89, substituting 1-(3-fluoro-benzyl)-1H-pyrazole-4-carboxylic acid (80.4 mg, 0.365 mmol) for 1-(4-fluoro-benzyl)-1H-pyrazole-4-carboxylic acid, in Step 1. The title compound was isolated as a white solid, 47 mg, 59.5%.

LC/MS: RT=1.81 Min (270 nm), m/z=464 [M+H]. Total run time 3.75 min (short pos), HP1100.

$^1$H NMR (d$_6$ DMSO): δ 1.21 (m, 1H), 1.46 (m, 1H), 1.66-2.13 (m, 4H), 2.86 (m, 2H), 3.03 (t, 2H), 3.21 (d, 1H), 3.86 (s, 3H), 5.44 (s, 2H), 7.07-7.19 (m, 3H), 7.42 (m, 1H), 7.70 (s, 1H), 8.04 (s, 1H), 8.06 (s, 1H), 8.60 (s, 1H), 9.73 (br s, 1H), 11.22 (br s, 1H)

Example 92: 1-(2-Chloro-benzyl)-1H-pyrazole-4-carboxylic acid [4-((R)-3-amino-piperidin-1-yl-methoxy-1H-pyrrolo[2,3-b]pyridin-3-yl]-amide

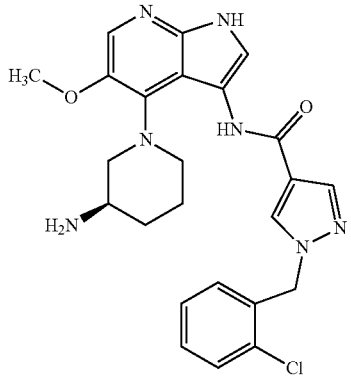 [SMILES: COc1cnc2[nH]cc(NC(=O)c3cnn(Cc4ccccc4Cl)c3)c2c1N1CCC[C@@H](N)C1]

The title compound was prepared according to the route outlined in Scheme 7, using the methodology described for Example 89, substituting 1-(2-chloro-benzyl)-1H-pyrazole-4-carboxylic acid (86.5 mg, 0.365 mmol) for 1-(4-fluoro-benzyl)-1H-pyrazole-4-carboxylic acid, in Step 1. The title compound was isolated as a white solid, 55 mg, 53.6%.

LC/MS: RT=1.86 Min (270 nm), m/z=480 [M+H]. Total run time 3.75 min (short pos). HP1100.

$^1$H NMR (d$_6$ DMSO): δ 1.17 (m, 1H), 1.44-1.72 (m, 5H), 2.84 (m, 2H), 3.04 (t, 2H), 3.20 (d, 1H), 3.86 (s, 3H), 5.52 (s, 2H), 7.15 (m, 1H), 7.38 (m, 2H), 7.52 (m, 1H), 7.73 (s, 1H), 8.04 (s, 1H), 8.06 (s, 1H), 8.50 (s, 1H), 9.75 (br s, 1H), 11.22 (br s, 1H)

Example 93: 1-(2-Methyl-benzyl)-1H-pyrazole-4-carboxylic acid [4-((R)-3-amino-piperidin-1-yl)-6-methoxy-1H-pyrrolo[2,3-b]pyridin-3-yl]-amide

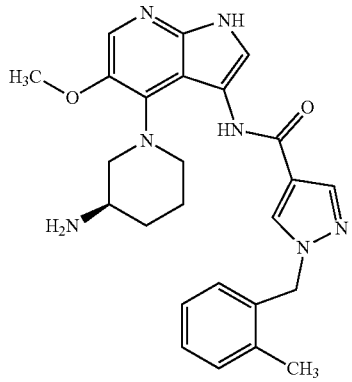 [SMILES: COc1cnc2[nH]cc(NC(=O)c3cnn(Cc4ccccc4C)c3)c2c1N1CCC[C@@H](N)C1]

The title compound was prepared according to the route outlined in Scheme 7, using the methodology described for Example 89, substituting 1-(2-methyl-benzyl)-1H-pyrazole-4-carboxylic acid (79 mg, 0.365 mmol) for 1-(4-fluoro-benzyl)-1H-pyrazole-4-carboxylic acid, in Step 1. The title compound was isolated as a white solid, 52 mg, 54.1%.

LC/MS: RT=1.86 Min (270 nm), m/z=460 [M+H]. Total run time 3.75 min (short pos), HP1100.

$^1$H NMR (d$_6$ DMSO): δ 1.17 (m, 1H), 1.42-1.74 (m, 5H), 2.28 (s, 3H), 2.83 (m, 2H), 3.02 (t, 2H), 3.21 (d, 1H), 3.85 (s, 3H), 5.42 (s, 2H), 7.07 (d, 1H), 7.24 (m, 3H), 7.72 (s, 1H), 8.01 (s, 1H), 8.06 (s, 1H), 8.41 (s, 1H), 9.71 (br s, 1H), 11.21 (br s, 1H)

Example 94: 1-(4-Fluoro-benzyl-1H-pyrazole-4-carboxylic acid [4-(R)-3-amino-piperidin-1-yl)-5-trifluoromethyl-1H-pyrrolo[2,3-b]pyridin-3-yl]-amide

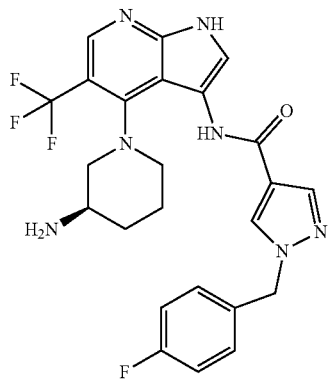 [SMILES: N[C@@H]1CCCN(c2c(C(F)(F)F)cnc3[nH]cc(NC(=O)c4cnn(Cc5ccc(F)cc5)c4)c23)C1]

The title compound was prepared according to the route outlined in Scheme 8.

Step 1: Preparation of 4-chloro-1-triisopropylsilanyl-1H-pyrrolo[2,3-b]pyridine

The title compound was prepared as described in Example 6. Step 1, substituting 4-chloro-1H-pyrrolo[2,3-b]pyridine (5 g, 32.8 mmol) for 4-bromo-1H-pyrrolo[2,3-b]pyridine. It was isolated as a colourless oil, 8.27 g, 81.7%.

Step 2: Preparation of 4-chloro-5-iodo-1H-pyrrolo[2,3-b]pyridine sec-Butyllithium solution, 1.4M in cyclohexane (15.82 mL, 22.15 mmol) was added drop wise to a solution of 4-chloro-1-triisopropylsilanyl-1H-pyrrolo[2,3-b]pyridine (3.91 g, 12.77 mmol) in THF (50 mL) at −78° C. The reaction was stirred at −78° C. for 30 minutes and then a solution of iodine (8.03 g, 31.64 mmol) in THF (25 mL) was added drop wise and the reaction was stirred at −78° C. for a further 45 minutes. The reaction was quenched by the addition of saturated aqueous ammonium chloride (50 mL) and the reaction allowed to attain RT. The mixture was extracted with iso-hexane (2×75 mL) and the combined extracts washed with saturated aqueous sodium sulfite (×2) and saturated aqueous sodium chloride. The solution was dried over anhydrous MgSO4 and concentrated to a colourless oil. This was taken up in THF (25 mL) and tetrabutylammonium fluoride solution, 1.0M in THF (12.7 mL, 12.7 mmol) was added drop wise at RT The reaction mixture was stirred at RT for 30 minutes and then partitioned between H$_2$O and EtOAc. The organic layer was separated and the aqueous was extracted with more EtOAc. The combined organic phases were washed with saturated aqueous sodium chloride, dried (MgSO$_4$) and concentrated in vacuo. The residue was stirred in DCM, filtered and washed with DCM prior to drying in vacuo. This afforded the title compound as a white solid, 2.72 g, 77.3%.

Step 3: Preparation of 1-benzenesulfonyl-4-chloro-5-iodo-1H-pyrrolo[2,3-b]pyridine Sodium hydride, 60% dispersion in mineral oil (0.508 g, 12.7 mmol) was added in portions to 4-chloro-5-iodo-1H-pyrrolo[2,3-b]pyridine (2.72 g, 10.74 mmol) in DMF (20 mL) at 0° C. The reaction was stirred for a further 15 minutes and then benzene sulphonyl chloride (1.9 g, 1.37 mL, 10.74 mmol) was added and the reaction stirred at RT for 2 hours. The reaction mixture was diluted with H$_2$O and after stirring for 15 minutes the precipitate was filtered off, washed with H$_2$O and with Et$_2$O. This furnished the title compound as a white powder, 3.47 g, 84.8%, after drying in vacuo.

Step 4: Preparation of 1-benzenesulfonyl-4-chloro-5-trifluoromethyl-1H-pyrrolo[2,3-b]pyridine Copper (I) iodide (0.78 g, 4.1 mmol) was added to a solution of 1-benzenesulfonyl-4-chloro-5-iodo-1H-pyrrolo[2,3-b]pyridine (1.43 g, 3.42 mmol) in DMF (10 mL). The mixture was degassed and methyl 2,2-difluoro-2-(fluorosulfonyl)acetate (2.3 g, 11.96 mmol) was added and mixture degassed again before heating at 100° C. for 2.5 hours. The reaction was cooled to RT and diluted with EtOAc (40 mL). The precipitate was separated by filtering through a plug of celite. The filtrate was washed with H$_2$O (20 mL), saturated aqueous sodium chloride (20 mL), dried (MgSO$_4$) and concentrated in vacuo. The crude material was purified by automated column chromatography eluting with iso-hexane to 25% EtOAc/iso-hexane (gradient). Fractions containing pure product were combined and concentrated in vacuo to afford the title compound as a white solid, 0.46 g, 37.5%. Fractions containing pure product and small impurities were combined and concentrated in vacuo. The residue was triturated with Et$_2$O to afford the title compound as a white powder, 0.26 g, 21.3%. This gave a yield of 0.72 g, 58.8% overall.

Step 5: Preparation of 4-chloro-5-trifluoromethyl-1H-pyrrolo[2,3-b]pyridine 1-benzenesulfonyl-4-chloro-5-trifluoromethyl-1H-pyrrolo[2,3-b]pyridine (1.5 g, 4.16 mmol) was stirred in THF (10 mL) and LiOH monohydrate (520 mgs, 12.47 mmol) in H$_2$O (6 mL) was added. The reaction mixture was stirred at RT for 64 hours and then the pH was adjusted to 7 by the addition of saturated aqueous potassium hydrogen sulphate. This was extracted with EtOAc (2×30 mL) and the combined organics washed with saturated aqueous sodium chloride, dried over MgSO$_4$ and concentrated in vacuo to afford the title compound as a pale yellow powder, 0.84 g, 91.8%.

Step 6: Preparation of 4-chloro-3-nitro-5-trifluoromethyl-1H-pyrrolo[2,3-b]pyridine The title compound was prepared according to the methodology described for Example 6, Step 5, substituting 4-chloro-5-trifluoromethyl-1H-pyrrolo[2,3-b]pyridine (842 mg, 3.82 mmol) for 5-bromo-4-fluoro-1H-pyrrolo[2,3-b]pyridine. It was isolated as a pale yellow powder, 0.78 g, 76.9%.

Step 7: Preparation of [(R)-1-(3-nitro-5-trifluoromethyl-1H-pyrrolo[2,3-b]pyridin-4-yl)-piperidin-3-yl]-carbamic acid tert-butyl ester The title compound was prepared according to the methodology described for Example 89, Step 1, substituting 4-chloro-3-nitro-5-trifluoromethyl-1H-pyrrolo[2,3-b]pyridine (200 mg, 0.75 mmol) for 4-fluoro-5-methoxy-3-nitro-1H-pyrrolo[2,3-b]pyridine. It was isolated as a yellow glass, 179 mg, 55.4%.

Step 8: Preparation of [(R)-1-(3-amino-5-trifluoromethyl-1H-pyrrolo[2,3-b]pyridin-4-yl)-piperidin-3-yl]-carbamic acid tert-butyl ester The title compound was prepared according to the methodology described for Example 31, Step 8, substituting [(R)-1-(3-nitro-5-trifluoromethyl-1H-pyrrolo[2,3-b]pyridin-4-yl)-piperidin-3-yl]-carbamic acid tert-butyl ester (179 mg, 0.42 mmol) for 2,2-dimethyl-propionic acid 4-((R)-3-tert-butoxycarbonylamino-piperidin-1-yl)-3-nitro-1H-pyrrolo[2,3-b]pyridin-5-yl ester. It was isolated as a green gum, 149 mgs, 88.9%.

Step 9: Preparation of [(R)-1-(3-{[1-(4-Fluoro-benzyl)-1H-pyrazole-4-carbonyl]-amino}-5-trifluoromethyl-1H-pyrrolo[2,3-b]pyridin-4-yl)-piperidin-3-yl]-carbamic acid tert-butyl ester 1-(4-Fluoro-benzyl)-1H-pyrazole-4-carboxylic acid (synthesis described in Example 17) was stirred as a suspension in DCM (2 mL) and oxalyl chloride, 2.0M solution in DCM (0.17 mL, 0.34 mmol) was added drop wise at RT followed by a drop of DMF. The reaction was stirred for a further 15 minutes and the subsequent solution was concentrated in vacuo. The residue was taken up in DCM (1 mL) and added drop wise to a solution of [(R)-1-(3-amino-5-trifluoromethyl-1H-pyrrolo[2,3-b]pyridin-4-yl)-piperidin-3-yl]-carbamic acid tert-butyl ester (62.3 mg, 0.28 mmol) in DCM (2 mL) containing Et$_3$N (90 mg, 0.12 mL, 0.85 mmol). After stirring for a further 1 hour the reaction was diluted with DCM and washed with H$_2$O. The organics were separated, dried (MgSO$_4$) and concentrated in vacuo. The residue was taken up in MeOH (5 mL) and after 50% w/v NaOH (1 mL) was added, the mixture was stirred for 18 hours at RT. The solvent removed in vacuo and the residue taken up in DCM. It was washed with H$_2$O, saturated aqueous sodium chloride, dried over MgSO$_4$ and concentrated in vacuo. The crude material was purified via automated column chromatography eluting with 25% EtOAc/iso-hexane to EtOAc (gradient). The fractions containing product were combined and concentrated in vacuo to afford the title compound as a yellow glass, 52 mg, 30.6%.

Step 10: Preparation of title compound: 1-(4-Fluoro-benzyl)-1H-pyrazole-4-carboxylic acid [4-((R)-3-amino-piperidin-1-yl)-5-trifluoromethyl-1H-pyrrolo[2,3-b]pyridin-3-yl]-amide

[(R)-1-(3-{[1-(4-Fluoro-benzyl)-1H-pyrazole-4-carbonyl]-amino}-5-trifluoromethyl-1H-pyrrolo[2,3-b]pyridin-4-yl)-piperidin-3-yl]-carbamic acid tert-butyl ester (50 mg, 0.08 mmol) was taken up in hydrochloric acid solution, 1.25M in MeOH (2 mL) and heated under microwave irradiation at 80° C. for 30 minutes. The solvent was removed in vacuo and residue taken up in minimum volume of MeOH and applied to a SCX-2 ion exchange cartridge. This was washed with MeOH and desired compound eluted with 4:1 DCM/7N NH$_3$ in MeOH and concentrated in vacuo. The crude material was further purified via automated column chromatography eluting with DCM to 15% MeOH (containing 5% 7N NH$_3$ in MeOH)/DCM (gradient). The fractions found to contain product were combined and concentrated in vacuo. The residue was triturated with diethyl ether to afford the title compound as a cream powder, 4.5 mgs, 10.8%.

LC/MS: RT=0.93 Min (230 nm), m/z=502.2 [M+H]. Total run time 1.9 min (super short pos), HP1200.

$^1$H NMR (d$_6$ DMSO): δ 0.82-0.93 (m, 1H), 1.38-1.50 (m, 1H), 1.54-1.65 (m, 2H), 2.70-2.81 (m, 2H), 2.80-3.00 (m, 2H), 3.1-3.09 (m, 1H), 5.42 (s, 2H), 7.16-7.24 (m, 2H), 7.28-7.36 (m, 2H), 7.70 (s, 1H), 8.08 (s, 1H), 8.45-8.48 (m, 2H), 9.62 (br s, 1H), 11.60-12.60 (br s, 1H) 2 protons not seen Example 95: 1-Benzyl-1H-pyrazole-4-carboxylic acid [4-((R)-3-amino-piperidin-1-yl-5-trifluoromethyl-1H-pyrrolo[2,3-b]pyridin-3-yl]-amide

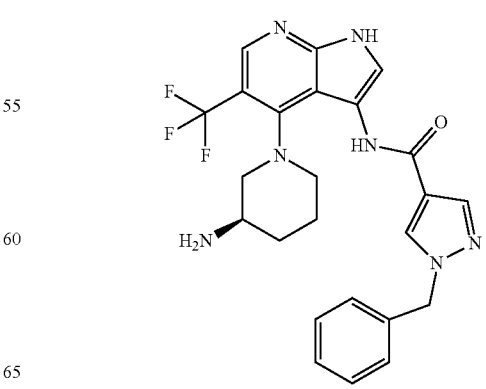

The title compound was prepared according to the methodology described for Example 94 in Steps 1 to 8.

Step 9: Preparation of ((R)-1-{3-[(1-benzyl-1H-pyrazole-4-carbonyl)-amino]-5-trifluoromethyl-1H-pyrrolo[2,3-b]pyridin-4-yl}-piperidin-3-yl)-carbamic acid tert-butyl ester This was prepared using the methodology described for Example 31, Step 9, substituting [(R)-1-(3-amino-5-trifluoromethyl-1H-pyrrolo[2,3-b]pyridin-4-yl)-piperidin-3-yl]-carbamic acid tert-butyl ester (60 mg, 0.15 mmol) for 2,2-dimethyl-propionic acid 3-amino-4-((R)-3-tert-butoxycarbonylamino-piperidin-1-yl)-1H-pyrrolo[2,3-b]pyridin-5-yl ester and DIPEA (40 mg, 50 uL, 0.3 mmol) for Et$_3$N. The title compound was isolated as a dark yellow glass, 63 mg, 71.9%.

Step 10: preparation of title compound: 1-benzyl-1H-pyrazole-4-carboxylic acid [4-((R)-3-amino-piperidin-1-yl)-5-trifluoromethyl-1H-pyrrolo[2,3-b]pyridin-3-yl]-amide This was prepared using the methodology described for Example 94, Step 10, substituting ((R)-1-{3-[(1-benzyl-1H-pyrazole-4-carbonyl)-amino]-5-trifluoromethyl-1H-pyrrolo[2,3-b]pyridin-4-yl}-piperidin-3-yl)-carbamic acid tert-butyl ester (63 mg, 0.11 mmol) for [(R)-1-(3-{[1-(4-fluoro-benzyl)-1H-pyrazole-4-carbonyl]-amino}-5-trifluoromethyl-1H-pyrrolo[2,3-b]pyridin-4-yl)-piperidin-3-yl]-carbamic acid tert-butyl ester. After the usual work up, the residue was taken up in minimum volume of MeOH and applied to a SCX-2 ion exchange cartridge. This was washed with MeOH and the desired compound eluted with 4:1 DCM/7N NH$_3$ in MeOH and concentrated in vacuo. The material was further purified by trituration with Et$_2$O and then MeCN. This afforded the title compound as a beige powder, 4.3 mg, 8.2%.

LC/MS: RT=0.91 Min (230 nm), m/z=484.2 [M+H]. Total run time 1.9 min (super short pos), HP1200.

$^1$H NMR (d$_6$ DMSO): δ 0.90-1.00 (m, 1H), 1.40-1.51 (m, 1H), 1.54-1.68 (m, 2H), 2.80-3.00 (m, 4H), 3.07-3.13 (m, 1H), 5.42 (s, 2H), 7.20-7.40 (m, 5H), 7.70 (s, 1H), 8.10 (s, 1H), 8.45-8.50 (m, 2H), 9.65 (br s, 1H), 11.00-13.00 (br s, 1H) 2 protons not seen Example 96: 1-Pyridin-3-ylmethyl-1H-pyrazole-4-carboxylic acid [4-((R)-3-amino-piperidin-1-yl)-5-trifluoromethyl-1H-pyrrolo[2,3-b]pyridin-3-yl]-amide

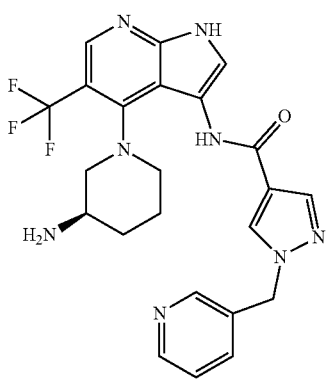 [SMILES: N[C@@H]1CCCN(c2c(C(F)(F)F)cnc3[nH]cc(NC(=O)c4cnn(Cc5cccnc5)c4)c23)C1]

The title compound was prepared according to the methodology described for Example 94, substituting 1-pyridin-3-ylmethyl-1H-pyrazole-4-carboxylic acid (57.5 mg, 0.28 mmol) for 1-(4-fluoro-benzyl)-1H-pyrazole-4-carboxylic acid, in Step 9. The title compound was isolated as a beige powder, 11.7 mg, 28.2%.

LC/MS: RT=0.78 Min (230 nm), m/z=485 [M+H]. Total run time 1.9 min (super short pos), HP1200.

$^1$H NMR (d$_6$ DMSO): δ 0.83-0.93 (m, 1H), 1.38-1.51 (m, 1H), 1.54-1.64 (m, 2H), 2.71-2.82 (m, 2H), 2.84-3.00 (m, 2H), 3.02-3.10 (m, 1H), 5.48 (s, 2H), 7.38-7.43 (m, 1H), 7.63-7.72 (m, 2H), 8.10, (s, 1H), 8.45 (s, 1H), 8.50-8.55 (m, 3H), 9.65 (br s, 1H), 11.60-12.60 (br s, 1H) 2 protons not seen Example 97: 1-Pyridin-2-ylmethyl-1H-pyrazole-4-carboxylic acid [4-((R)-3-amino-piperidin-1-yl-5-trifluoromethyl-1H-pyrrolo[2,3-b]pyridin-3-yl]-amide

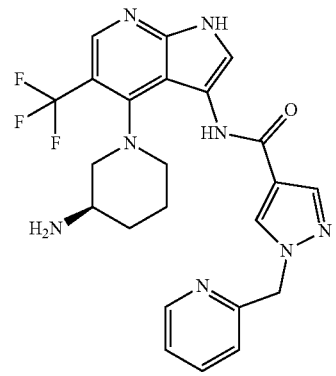 [SMILES: N[C@@H]1CCCN(c2c(C(F)(F)F)cnc3[nH]cc(NC(=O)c4cnn(Cc5ccccn5)c4)c23)C1]

The title compound was prepared according to the methodology described for Example 94, substituting 1-pyridin-2-ylmethyl-1H-pyrazole-4-carboxylic acid (57.5 mg, 0.28 mmol) for 1-(4-fluoro-benzyl)-1H-pyrazole-4-carboxylic acid, in Step 9. The title compound was isolated as a beige powder, 15.1 mg, 43.4%.

LC/MS: RT=0.82 Min (230 nm), m/z=485.2 [M+H]. Total run time 1.9 min (super short pos), HP1200.

$^1$H NMR (d$_6$ DMSO): δ 0.88-0.99 (m, 1H), 1.42-1.54 (m, 1H), 1.57-1.69 (m, 2H), 2.73-2.84 (m, 2H), 2.84-3.00 (m, 2H), 3.04-3.11 (m, 1H), 5.53 (s, 2H), 7.10 (d, 1H), 7.31-7.37 (m, 1H), 7.72 (s, 1H), 7.80 (m, 1H), 8.07, (s, 1H), 8.45-8.57 (m, 3H), 9.68 (br s, 1H), 11.60-12.60 (br s, 1H) 2 protons not seen

GENERAL PROCEDURES

All reagents obtained from commercial sources were used without further purification. Anhydrous solvents were obtained from commercial sources and used without further drying. Flash chromatography was performed with pre-packed silica-gel cartridges (Isolute Flash Si II, 56 Å, Biotage). Automated flash chromatography was performed on a Teledyne Isco CombiFlash® Rf purification system with pre-packed silica-gel cartridges (SilaSep™ Flash, 60 Å, Silicycle). Ion exchange chromatography was performed using isolute SCX-2, SPE columns, Biotage. Thin layer chromatography was conducted with 5×10 cm plates coated with Silica 60 (Machery-Nagel). Microwave heating was performed with a Biotage Initiator Eight™ 2.0 instrument, a CEM explorer 24 or a CEM explorer 48.

The compounds of the present invention were characterized by high performance liquid chromatography-mass spectroscopy (HPLC-MS) on either an Agilent HP1200 Rapid Resolution Mass detector 6140 multimode source M/z range 150 to 1000 amu or an Agilent HP1100 Mass detector 1946D ESI source M/z range 150 to 1000 amu. The conditions and methods listed below are identical for both machines.

Column for 7.5 min run: GeminiNX, 5 μm, C18, 30×2.1 mm (Phenomenex) or Zorbax Eclipse Plus, 3.5 μm, C18, 30×2.1 mm (Agilent).
Temperature: 35° C.
Column for 3.75 min run: GeminiNX, 5 μm, C18, 30×2.1 mm (Phenomenex) or Zorbax Eclipse Plus, 3.5 μm, C18, 30×2.1 mm (Agilent).
Temperature: 35° C.
Column for 1.9 min run: Kinetex, 2.5 μm, C18, 50×2.1 mm (Phenomenex) or Accucore, 2.6 μm, C18, 50×2.1 mm.
Temperature: 55° C.
Mobile Phase: A—$H_2O$+10 mmol/ammonium formate+0.08% (v/v) formic acid at pH ca 3.5.
B—95% Acetonitrile+5% A+0.08% (v/v) formic acid.
Injection Volume: 1 μL
"Short" method gradient table, either positive (pos) or positive and negative (pos/neg) ionisation

| Time (min) | Solvent A (%) | Solvent B (%) | Flow (mL/min) |
|---|---|---|---|
| 0 | 95 | 5 | 1 |
| 0.25 | 95 | 5 | 1 |
| 2.50 | 5 | 95 | 1 |
| 2.55 | 5 | 95 | 1.7 |
| 3.60 | 5 | 95 | 1.7 |
| 3.65 | 5 | 95 | 1 |
| 3.70 | 95 | 5 | 1 |
| 3.75 | 95 | 5 | 1 |

"Super Short" method gradient table, either positive (pos) or positive and negative (pos/neg) ionisation

| Time (min) | Solvent A (%) | Solvent B (%) | Flow (mL/min) |
|---|---|---|---|
| 0 | 95 | 5 | 1.3 |
| 0.12 | 95 | 5 | 1.3 |
| 1.30 | 5 | 95 | 1.3 |
| 1.35 | 5 | 95 | 1.6 |
| 1.85 | 5 | 95 | 1.6 |
| 1.90 | 5 | 95 | 1.3 |
| 1.95 | 95 | 5 | 1.3 |

"Long" method gradient table, either positive (pos) or positive and negative (pos/neg) ionisation

| Time (min) | Solvent A (%) | Solvent B (%) | Flow (mL/min) |
|---|---|---|---|
| 0 | 95 | 5 | 1 |
| 0.25 | 95 | 5 | 1 |
| 5.50 | 5 | 95 | 1 |
| 7.25 | 5 | 95 | 1 |
| 7.50 | 95 | 5 | 1 |

Detection: UV detection at 230, 254 and 270 nm.
The compounds of the present invention were also characterized by Nuclear Magnetic Resonance (NMR). Analysis was performed with a Bruker DPX400 spectrometer and proton NMR spectra were measured at 400 MHz. The spectral reference was the known chemical shift of the solvent. Proton NMR data is reported as follows: chemical shift (δ) in ppm, followed by the multiplicity, where s=singlet, d=doublet, t=triplet, q=quartet, m=multiplet, dd=doublet of doublets, dt=doublet of triplets, dm=doublet of multiplets, ddd=doublet of double doublets, td=triplet of doublets, qd=quartet of doublets and br=broad, and finally the integration.

Some compounds of the invention were purified by preparative HPLC. These were performed on a $H_2Os$ Fraction-Lynx MS autopurification system, with a Gemini-NX® 5 μm. C18, 100 mm×21 mm i.d. Axia column from Phenomenex, running at a flow rate of 20 $cm^3$ $min^{-1}$ with UV diode array detection (210-400 nm), and mass-directed collection. Gradients used for each compound are shown in Tables above.

At pH 4: solvent A=10 mM ammonium formate in HPLC grade $H_2O$+0.08% v/v formic acid. Solvent B=95% v/v HPLC grade acetonitrile+5% v/v solvent A+0.08% v/v formic acid.

At pH 9: solvent A=10 mM ammonium formate in HPLC grade $H_2O$+0.08% v/v ammonia solution. Solvent B=95% v/v HPLC grade MeOH+5% v/v solvent A+0.08% v/v ammonia solution.

The mass spectrometer was a $H_2Os$ Micromass ZQ2000 spectrometer, operating in positive and negative ion electrospray ionisation modes, with a molecular weight scan range of 150 to 1000.

IUPAC chemical names were generated using AutoNom Standard.

Assay Protocols
CHK1 Enzyme Assay

Assays for the CHK1 kinase activity were carried out by monitoring the phosphorylation of a synthetic peptide Chktide with the amino acid sequence, KKKVSRSGLYR-SPSMPENLNRPR. The assay mixture containing the inhibitor and CHK1 enzyme was mixed together in a microtiter plate in a final volume of 50 μl and incubated for 40 minutes at 30° C.

The assay mixture contained 0.02 mM unlabeled ATP, 0.5 μCi $^{33}$P-γ-ATP, 15 μM Chktide, 0.1 mg/mL BSA, 50 mM Hepes-NaOH pH 7.5 and 5 nM CHK-1(1-289)-8HIS (Vemalis) enzyme. The reaction was stopped by adding 50 μL of 50 mM phosphoric acid, 90 uL of the mixture was transferred to a pre-wetted 96-well multi-screen MAPHNOB filtration plate (Millipore) and filtered on a vacuum manifold. The filter plate was washed with 3 successive additions of 100 μl 50 mM phosphoric acid and then with 50 μL MeOH. The filtration plate was dried for 10 min at 65° C., scintillant added and phosphorylated peptide quantified in a scintillation counter (Trilux, PerkinElmer).

CHK-1 Enzyme Assay (TR-FRET)

CHK activity was also assessed using LanthaScreen TR-FRET technology (Life Technologies) by monitoring the phosphorylation of a synthetic fluorescein-labelled peptide based on ezrin/radixin/moesin (ERM) (amino acid sequence GAGRLGRDKYKTLRQIRQ). The assay mixture containing the inhibitor and CHK-1 enzyme was mixed together in a microtiter plate in a final volume of 20 μl and incubated for 80 minutes at 30° C.

The assay mixture contained 50 mM HEPES pH 7.5, 10 mM MgCl₂, 1 mM EGTA, 0.01% Brij-35, 200 µM ATP, 400 nM fluorescein-labelled ERM (Life Technologies), and 1 nM full length HIS-tagged CHK-1 (Life Technologies). The reaction was stopped by adding 20 µL of TR-FRET dilution buffer (Life Technologies) containing 20 mM EDTA and 1 nM terbium-labelled anti-pERM antibody (Life Technologies). The quenched reaction was incubated for 30 minutes at room temperature with shaking to allow antibody to bind to phosphorylated ERM, and then fluorescence from the donor fluorophore (terbium) and acceptor fluorophore (fluorescein) was measured using a Synergy2 Multi-Mode Microplate Reader (BioTek) at 495 nm and 520 nm respectively. The TR-FRET ratio was calculated as 520 nm/495 nm.

CHK-1 Binding Assay (TR-FRET)

Compounds were assessed for CHK-1 binding using LanthaScreen TR-FRET technology (Life Technology). Assay mixture containing inhibitor, 50 mM HEPES pH 7.5, 10 mM MgCl₂, 1 mM EGTA, 0.01% Brij-35, 2 nM biotin-labelled anti-HIS tag antibody (Life Technologies), 2 nM Europium-labelled streptavidin (Life Technologies), 100 nM AlexaFluor-labelled Tracer236 (Life Technologies), and either 10 nM or 30 nM CHK-1(1-289)-8HIS (Vemalis) enzyme, was incubated in a microtitre plate for 120 minutes at 23° C. A final volume of 15 µL was used.

Fluorescence from the donor fluorophore (europium) and acceptor fluorophore (Alexa Fluor) was measured using a Synergy2 Multi-Mode Microplate Reader (BioTek) at 620 nm and 665 nm respectively. The TR-FRET ratio was calculated as 665 nm/620 nm.

All the compounds exemplified in the patent were tested in one, two or all three of the above assays and were found to have an IC₅₀ of less than 1 µM. A majority of Examples 1-97 were found to have an IC₅₀ of less than 0.1 µM.

CHK1 Cellular Assay—Gemcitabine EC₅₀ Assay

HT29 cells were purchased from ATCC (Manassas, Va., US) and cultured in Dulbecco's modified Eagles medium (DMEM) supplemented with 10% foetal calf serum (FCS) and penicillin/streptomycin at 37° C., 5% CO₂ in a humidified incubator, 5×10³ HT29 cells were seeded per well of a 96-well plate and allowed to incubate overnight. Tripling dilutions of compound, prepared in DMEM/10% FCS plus 15 nM gemcitabine, were added to the cells and incubated at 37'C for 72 hours. Cells were then fixed with 10% trichloroacetic acid (TCA) stained with sulphorhodamine B (SRB) and the absorbance determined at 540 nm. Curves were analysed using XLFit 4 (Excel) with model 205 (fit=(A+((B−A)/(1+((C/x)^D))))). The EC₅₀ was determined as the concentration of compound that inhibited growth by 50% at a given concentration of gemcitabine.

All the compounds exemplified in the patent were tested in the above assay in the presence of gemcitabine at 15 nM, and were found to have an EC₅₀ of less than 1 µM. A majority of Examples 1-97 were found to have an EC₅₀ of less than 0.1 µM.

The invention claimed is:

1. A method for treating ovarian cancer, triple negative breast cancer, melanoma, neuroblastoma, or pancreatic cancer in a mammal subject in need thereof comprising administering to the mammal subject a therapeutically effective amount of a compound of formula (I):

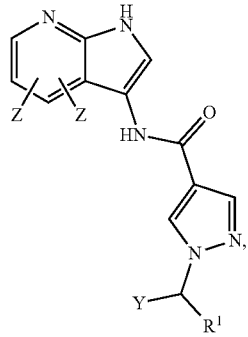

or a pharmaceutically acceptable salt thereof, wherein:
each Z is independently $(Alk)_n-R_n-(Alk)_n-X$, wherein:
each Alk is independently ($C_1$ to $C_{12}$) alkylene or ($C_2$ to $C_{12}$) alkenylene, each of which is optionally substituted;
each n is independently 0 or 1;
each R is independently optionally substituted arylene, optionally substituted heteroarylene, optionally substituted cycloalkylene, optionally substituted heterocycle, —O—, —S—, —(C=O)—, —(C=S)—, —SO₂—, —C(=O)O—, —C(=O)NR$^A$—, —C(=S)NR$^A$—, —SO₂NR$^A$—, —NR$^A$C(=O)—, —NR$^A$SO₂—, or —NR$^A$—, wherein R$^A$ is hydrogen, $C_1$-$C_6$ alkyl, —$C_1$-$C_6$ alkyl(cycloalkyl), $C_1$-$C_6$ alkyl($C_1$-$C_6$ alkoxy), or $C_1$-$C_6$ alkoxy; and
each X is independently halogen, —H, —OR$^A$, —NR$^A$R$^A$, optionally substituted aryl, optionally substituted heteroaryl, optionally substituted cycloalkyl, optionally substituted heterocycle, CN, or C(halogen)$_a$H$_b$, where a is 1, 2, or 3, and b is (3-a);
Y is phenyl optionally substituted with $C_1$ to $C_6$ alkyl or halogen; optionally substituted, bicyclic or tricyclic aryl; optionally substituted heteroaryl; optionally substituted cycloalkyl; or optionally substituted heterocycle; and
R¹ is H or $C_1$-$C_6$ alkyl.

2. The method according to claim 1, wherein the cancer is ovarian cancer.

3. The method according to claim 1, wherein the condition is cancer and the compound is administered in combination with radiotherapy or chemotherapy.

4. The method according to claim 1, wherein R$^A$ is hydrogen or $C_1$-$C_6$ alkyl.

5. The method according to claim 1, wherein at least one Z is H, halogen, optionally substituted aryl, optionally substituted heteroaryl, optionally substituted nitrogen-containing heterocycle, $C_1$ to $C_6$ alkyl, or —OR$^A$.

6. The method according to claim 5, wherein one Z group is H, halogen, —OR$^A$, or $C_1$ to $C_6$ alkyl, and the other Z group is optionally substituted aryl or optionally substituted nitrogen-containing heterocycle.

7. The method according to claim 6, wherein the nitrogen-containing heterocycle is substituted with —NR$^A$R$^A$.

8. The method according to claim 1, wherein at least one Z is $(Alk)_n$-optionally substituted arylene-$(Alk)_n$-optionally substituted heterocycle.

9. The method according to claim 1, wherein R is H.

10. The method according to claim 1, wherein Y is phenyl optionally substituted with $C_1$ to $C_6$ alkyl or halogen; or heteroaryl optionally substituted with $C_1$ to $C_6$ alkyl, —OR$^A$, halogen, or $C_1$ to $C_6$ alkoxy.

11. The method according to claim 1, wherein Y is pyridyl, pyrrolyl, phenyl; or phenyl substituted with methyl, bromine, or chlorine.

12. The method according to claim 1, wherein the compound is of the formula (Ia):

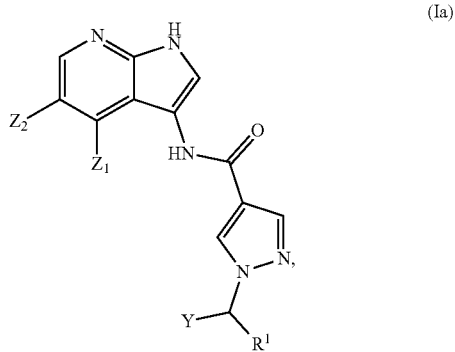

(Ia)

or a pharmaceutically acceptable salt thereof, wherein:
$Z_1$ and $Z_2$ are independently $(Alk)_n$-$R_n$-$(Alk)_n$-X.

13. The method according to claim 12, wherein $Z_1$ is halogen, phenyl, —$OR^A$, or $C_1$ to $C_6$ alkyl, and $Z_2$ is optionally substituted aryl or optionally substituted heterocycle.

14. The method according to claim 12, wherein $Z_2$ is halogen, $CF_3$, cyclopropyl, phenyl, —$OR^A$, or $C_1$ to $C_6$ alkyl, and $Z_1$ is optionally substituted aryl or optionally substituted heterocycle.

15. The method according to claim 12, wherein the optionally substituted heterocycle is an optionally substituted piperidine, optionally substituted piperazine, or optionally substituted morpholine.

16. The method according to claim 1, wherein the compound is one of the compounds listed below, or a pharmaceutically acceptable salt thereof:

1-Benzyl-1H-pyrazole-4-carboxylic acid (5-bromo-1H-pyrrolo[2,3-b]pyridin-3-yl)-amide;
1-Benzyl-1H-pyrazole-4-carboxylic acid (1H-pyrrolo[2,3-b]pyridin-3-yl)-amide;
1-Benzyl-1H-pyrazole-4-carboxylic acid (4-bromo-1H-pyrrolo[2,3-b]pyridin-3-yl)-amide;
1-Benzyl-1H-pyrazole-4-carboxylic acid (5-phenyl-1H-pyrrolo[2,3-b]pyridin-3-yl)-amide;
1-Benzyl-1H-pyrazole-4-carboxylic acid (5-piperidin-1-yl-1H-pyrrolo[2,3-b]pyridin-3-yl)-amide;
N-{4-[(3R)-3-Aminopiperidin-1-yl]-5-bromo-1H-pyrrolo[2,3-b]pyridin-3-yl}-1-benzyl-1H-pyrazole-4-carboxamide;
1-Benzyl-1H-pyrazole-4-carboxylic acid [4-((R)-3-amino-pyrrolidin-1-yl)-5-bromo-1H-pyrrolo[2,3-b]pyridin-3-yl]-amide;
1-Benzyl-1H-pyrazole-4-carboxylic acid [5-bromo-4-((R)-3-methylamino-piperidin-1-yl)-1H-pyrrolo[2,3-b]pyridin-3-yl]-amide;
1-Benzyl-1H-pyrazole-4-carboxylic acid [5-bromo-4-((R)-3-ethylamino-piperidin-1-yl)-1H-pyrrolo[2,3-b]pyridin-3-yl]-amide;
1-Benzyl-1H-pyrazole-4-carboxylic acid [5-bromo-4-((R)-3-hydroxy-pyrrolidin-1-yl)-1H-pyrrolo[2,3-b]pyridin-3-yl]-amide;
1-Benzyl-1H-pyrazole-4-carboxylic acid [5-bromo-4-((R)-3-hydroxy-piperidin-1-yl)-1H-pyrrolo[2,3-b]pyridin-3-yl]-amide;
1-Benzyl-1H-pyrazole-4-carboxylic acid [5-bromo-4-(3-dimethylamino-piperidin-1-yl)-1H-pyrrolo[2,3-b]pyridin-3-yl]-amide;
1-Benzyl-1H-pyrazole-4-carboxylic acid {5-bromo-4-[(R)-3-(cyclopentylmethyl-amino)-piperidin-1-yl]-1H-pyrrolo[2,3-b]pyridin-3-yl}-amide;
1-Benzyl-1H-pyrazole-4-carboxylic acid [5-bromo-4-((R)-3-isobutylamino-piperidin-1-yl)-1H-pyrrolo[2,3-b]pyridin-3-yl]-amide;
1-Benzyl-1H-pyrazole-4-carboxylic acid {5-bromo-4-[(R)-3-(2,2-dimethyl-propylamino)-piperidin-1-yl]-1H-pyrrolo[2,3-b]pyridin-3-yl}-amide;
1-Benzyl-1H-pyrazole-4-carboxylic acid {5-bromo-4-[(R)-3-(cyclopropylmethyl-amino)-piperidin-1-yl]-1H-pyrrolo[2,3-b]pyridin-3-yl}-amide;
1-(4-Fluoro-benzyl)-1H-pyrazole-4-carboxylic acid [4-((R)-3-amino-piperidin-1-yl)-5-bromo-1H-pyrrolo[2,3-b]pyridin-3-yl]-amide;
1-(4-Chloro-benzyl)-1H-pyrazole-4-carboxylic acid [4-((R)-3-amino-piperidin-1-yl)-5-bromo-1H-pyrrolo[2,3-b]pyridin-3-yl]-amide;
1-(4-Methyl-benzyl)-1H-pyrazole-4-carboxylic acid [4-((R)-3-amino-piperidin-1-yl)-5-bromo-1H-pyrrolo[2,3-b]pyridin-3-yl]-amide;
1-Pyridin-2-ylmethyl-1H-pyrazole-4-carboxylic acid [4-((R)-3-amino-piperidin-1-yl)-5-bromo-1H-pyrrolo[2,3-b]pyridin-3-yl]-amide;
1-Pyridin-3-ylmethyl-1H-pyrazole-4-carboxylic acid [4-((R)-3-amino-piperidin-1-yl)-5-bromo-1H-pyrrolo[2,3-b]pyridin-3-yl]-amide;
1-Pyridin-4-ylmethyl-1H-pyrazole-4-carboxylic acid [4-((R)-3-amino-piperidin-1-yl)-5-bromo-1H-pyrrolo[2,3-b]pyridin-3-yl]-amide;
N-{4-[(3R)-3-aminopiperidin-1-yl]-5-chloro-1H-pyrrolo[2,3-b]pyridin-3-yl}-1-benzyl-1H-pyrazole-4-carboxamide;
1-(4-Methyl-benzyl)-1H-pyrazole-4-carboxylic acid [4-((R)-3-amino-piperidin-1-yl)-5-chloro-1H-pyrrolo[2,3-b]pyridin-3-yl]-amide;
1-(4-Fluoro-benzyl)-1H-pyrazole-4-carboxylic acid [4-((R)-3-amino-piperidin-1-yl)-5-chloro-1H-pyrrolo[2,3-b]pyridin-3-yl]-amide;
1-(4-Chloro-benzyl)-1H-pyrazole-4-carboxylic acid [4-((R)-3-amino-piperidin-1-yl)-5-chloro-1H-pyrrolo[2,3-b]pyridin-3-yl]-amide;
1-Benzyl-1H-pyrazole-4-carboxylic acid [4-((R)-3-amino-pyrrolidin-1-yl)-5-chloro-1H-pyrrolo[2,3-b]pyridin-3-yl]-amide;
N-{4-[(3R)-3-aminopiperidin-1-yl]-5-cyclopropyl-1H-pyrrolo[2,3-b]pyridin-3-yl}-1-benzyl-1H-pyrazole-4-carboxamide;
1-Benzyl-1H-pyrazole-4-carboxylic acid [4-((R)-3-amino-piperidin-1-yl)-5-hydroxy-1H-pyrrolo[2,3-b]pyridin-3-yl]-amide;
1-Benzyl-1H-pyrazole-4-carboxylic acid [4-((R)-3-amino-piperidin-1-yl)-5-methoxy-1H-pyrrolo[2,3-b]pyridin-3-yl]-amide;
1-Benzyl-1H-pyrazole-4-carboxylic acid [4-((R)-3-amino-piperidin-1-yl)-5-methyl-1H-pyrrolo[2,3-b]pyridin-3-yl]-amide;
1-Benzyl-1H-pyrazole-4-carboxylic acid [5-(4-piperidin-1-ylmethyl-phenyl)-1H-pyrrolo[2,3-b]pyridin-3-yl]-amide;
1-Benzyl-1H-pyrazole-4-carboxylic acid [5-(4-{[(2-methoxy-ethyl)-methyl-amino]-methyl}-phenyl)-1H-pyrrolo[2,3-b]pyridin-3-yl]-amide;

1-Benzyl-1H-pyrazole-4-carboxylic acid [5-(4-pyrrolidin-1-ylmethyl-phenyl)-1H-pyrrolo[2,3-b]pyridin-3-yl]-amide;
1-Benzyl-1H-pyrazole-4-carboxylic acid {5-[4-(4-fluoro-piperidin-1-ylmethyl)-phenyl]-1H-pyrrolo[2,3-b]pyridin-3-yl}-amide;
1-Benzyl-1H-pyrazole-4-carboxylic acid [5-(4-dimethylaminomethyl-phenyl)-1H-pyrrolo[2,3-b]pyridin-3-yl]-amide;
1-Benzyl-1H-pyrazole-4-carboxylic acid {5-[4-(3-fluoro-piperidin-1-ylmethyl)-phenyl]-1H-pyrrolo[2,3-b]pyridin-3-yl}-amide;
1-Benzyl-1H-pyrazole-4-carboxylic acid [5-(4-methylaminomethyl-phenyl)-1H-pyrrolo[2,3-b]pyridin-3-yl]-amide;
1-Benzyl-1H-pyrazole-4-carboxylic acid [5-(4-morpholin-4-ylmethyl-phenyl)-1H-pyrrolo[2,3-b]pyridin-3-yl]-amide;
1-Benzyl-1H-pyrazole-4-carboxylic acid {5-[4-(3,3-difluoro-pyrrolidin-1-ylmethyl)-phenyl]-1H-pyrrolo[2,3-b]pyridin-3-yl}-amide;
1-Benzyl-1H-pyrazole-4-carboxylic acid [5-(3-dimethylaminomethyl-phenyl)-1H-pyrrolo[2,3-b]pyridin-3-yl]-amide;
1-Benzyl-1H-pyrazole-4-carboxylic acid {5-[3-(3-fluoro-piperidin-1-ylmethyl)-phenyl]-1H-pyrrolo[2,3-b]pyridin-3-yl}-amide;
1-Benzyl-1H-pyrazole-4-carboxylic acid {5-[3-(3,3-difluoro-piperidin-1-ylmethyl)-phenyl]-1H-pyrrolo[2,3-b]pyridin-3-yl}-amide;
1-Benzyl-1H-pyrazole-4-carboxylic acid [5-(3-azetidin-1-ylmethyl-phenyl)-1H-pyrrolo[2,3-b]pyridin-3-yl]-amide;
1-Benzyl-1H-pyrazole-4-carboxylic acid {5-[3-(3,3-difluoro-azetidin-1-ylmethyl)-phenyl]-1H-pyrrolo[2,3-b]pyridin-3-yl}-amide;
1-Benzyl-1H-pyrazole-4-carboxylic acid [5-(5-pyrrolidin-1-ylmethyl-thiophen-2-yl)-1H-pyrrolo[2,3-b]pyridin-3-yl]-amide;
1-Benzyl-1H-pyrazole-4-carboxylic acid [5-(5-pyrrolidin-1-ylmethyl-thiophen-3-yl)-1H-pyrrolo[2,3-b]pyridin-3-yl]-amide;
1-Benzyl-1H-pyrazole-4-carboxylic acid {5-[5-(3,3-difluoro-azetidin-1-ylmethyl)-thiophen-3-yl]-1H-pyrrolo[2,3-b]pyridin-3-yl}-amide;
1-Benzyl-1H-pyrazole-4-carboxylic acid [5-(3-pyrrolidin-1-ylmethyl-phenyl)-1H-pyrrolo[2,3-b]pyridin-3-yl]-amide;
1-Benzyl-1H-pyrazole-4-carboxylic acid [4-((R)-3-amino-piperidin-1-yl)-5-fluoro-1H-pyrrolo[2,3-b]pyridin-3-yl]-amide;
1-Benzyl-1H-pyrazole-4-carboxylic acid [4-((R)-3-amino-piperidin-1-yl)-5-phenyl-1H-pyrrolo[2,3-b]pyridin-3-yl]-amide;
1-Benzyl-1H-pyrazole-4-carboxylic acid [4-((R)-3-amino-piperidin-1-yl)-5-cyano-1H-pyrrolo[2,3-b]pyridin-3-yl]-amide;
1-Benzyl-1H-pyrazole-4-carboxylic acid {5-[3-(2-morpholin-4-yl-ethoxy)-phenyl]-1H-pyrrolo[2,3-b]pyridin-3-yl}-amide;
1-Benzyl-1H-pyrazole-4-carboxylic acid {5-[3-(3-dimethylamino-2,2-dimethyl-propoxy)-phenyl]-1H-pyrrolo[2,3-b]pyridin-3-yl}-amide;
1-Benzyl-1H-pyrazole-4-carboxylic acid {5-[3-(3-morpholin-4-yl-propoxy)-phenyl]-1H-pyrrolo[2,3-b]pyridin-3-yl}-amide;
1-Benzyl-1H-pyrazole-4-carboxylic acid {5-[3-(1-methyl-piperidin-3-ylmethoxy)-phenyl]-1H-pyrrolo[2,3-b]pyridin-3-yl}-amide;
1-Benzyl-1H-pyrazole-4-carboxylic acid {5-[3-(oxetan-3-yloxy)-phenyl]-1H-pyrrolo[2,3-b]pyridin-3-yl}-amide;
1-Benzyl-1H-pyrazole-4-carboxylic acid {5-[3-(2-pyrrolidin-1-yl-ethoxy)-phenyl]-1H-pyrrolo[2,3-b]pyridin-3-yl}-amide;
1-Benzyl-1H-pyrazole-4-carboxylic acid [4-((3R,4R)-3-amino-4-cyclopropyl-piperidin-1-yl)-5-bromo-1H-pyrrolo[2,3-b]pyridin-3-yl]-amide;
1-Benzyl-1H-pyrazole-4-carboxylic acid [5-(2-fluoro-4-pyrrolidin-1-ylmethyl-phenyl)-1H-pyrrolo[2,3-b]pyridin-3-yl]-amide;
1-Benzyl-1H-pyrazole-4-carboxylic acid [5-(3-pyrrolidin-1-yl-phenyl)-1H-pyrrolo[2,3-b]pyridin-3-yl]-amide;
1-Benzyl-1H-pyrazole-4-carboxylic acid [5-(1-methyl-1H-pyrazol-4-yl)-1H-pyrrolo[2,3-b]pyridin-3-yl]-amide;
1-Benzyl-1H-pyrazole-4-carboxylic acid (5-pyridin-4-yl-1H-pyrrolo[2,3-b]pyridin-3-yl)-amide;
1-Benzyl-1H-pyrazole-4-carboxylic acid (5-pyridin-3-yl-1H-pyrrolo[2,3-b]pyridin-3-yl)-amide;
1-(2-Fluoro-benzyl)-1H-pyrazole-4-carboxylic acid (5-bromo-1H-pyrrolo[2,3-b]pyridin-3-yl)-amide;
1-(2-Cyano-benzyl)-1H-pyrazole-4-carboxylic acid (5-bromo-1H-pyrrolo[2,3-b]pyridin-3-yl)-amide;
1-(1H-Pyrrol-2-ylmethyl)-1H-pyrazole-4-carboxylic acid (5-bromo-1H-pyrrolo[2,3-b]pyridin-3-yl)-amide;
1-(4-Fluoro-benzyl)-1H-pyrazole-4-carboxylic acid (5-bromo-1H-pyrrolo[2,3-b]pyridin-3-yl)-amide;
1-Benzyl-1H-pyrazole-4-carboxylic acid (5-methyl-1H-pyrrolo[2,3-b]pyridin-3-yl)-amide;
1-Benzyl-1H-pyrazole-4-carboxylic acid (5-chloro-1H-pyrrolo[2,3-b]pyridin-3-yl)-amide;
1-(4-Fluoro-benzyl)-1H-pyrazole-4-carboxylic acid (5-chloro-1H-pyrrolo[2,3-b]pyridin-3-yl)-amide;
1-Benzyl-1H-pyrazole-4-carboxylic acid {5-[3-((S)-1-methyl-pyrrolidin-2-ylmethoxy)-phenyl]-1H-pyrrolo[2,3-b]pyridin-3-yl}-amide;
1-Benzyl-1H-pyrazole-4-carboxylic acid {5-[3-(1-methyl-piperidin-3-yloxy)-phenyl]-1H-pyrrolo[2,3-b]pyridin-3-yl}-amide;
1-Benzyl-1H-pyrazole-4-carboxylic acid {5-[4-(3-dimethylamino-propoxy)-phenyl]-1H-pyrrolo[2,3-b]pyridin-3-yl}-amide;
1-Benzyl-1H-pyrazole-4-carboxylic acid {5-[1-(2-diethylamino-ethyl)-1H-pyrazol-4-yl]-1H-pyrrolo[2,3-b]pyridin-3-yl}-amide;
1-Benzyl-1H-pyrazole-4-carboxylic acid {5-[1-(2-pyrrolidin-1-yl-ethyl)-1H-pyrazol-4-yl]-1H-pyrrolo[2,3-b]pyridin-3-yl}-amide;
1-Pyridin-4-ylmethyl-1H-pyrazole-4-carboxylic acid [4-((R)-3-amino-piperidin-1-yl)-5-methoxy-1H-pyrrolo[2,3-b]pyridin-3-yl]-amide;
1-Pyridin-3-ylmethyl-1H-pyrazole-4-carboxylic acid [4-((R)-3-amino-piperidin-1-yl)-5-methoxy-1H-pyrrolo[2,3-b]pyridin-3-yl]-amide;
1-Pyridin-2-ylmethyl-1H-pyrazole-4-carboxylic acid [4-((R)-3-amino-piperidin-1-yl)-5-methoxy-1H-pyrrolo[2,3-b]pyridin-3-yl]-amide;
1-Pyridin-3-ylmethyl-1H-pyrazole-4-carboxylic acid [4-((R)-3-amino-piperidin-1-yl)-5-chloro-1H-pyrrolo[2,3-b]pyridin-3-yl]-amide;

1-Pyridin-4-ylmethyl-1H-pyrazole-4-carboxylic acid [4-((R)-3-amino-piperidin-1-yl)-5-chloro-1H-pyrrolo[2,3-b]pyridin-3-yl]-amide;

1-Pyridin-2-ylmethyl-1H-pyrazole-4-carboxylic acid [4-((R)-3-amino-piperidin-1-yl)-5-chloro-1H-pyrrolo[2,3-b]pyridin-3-yl]-amide;

1-Pyridin-4-ylmethyl-1H-pyrazole-4-carboxylic acid [4-((R)-3-amino-piperidin-1-yl)-5-methyl-1H-pyrrolo[2,3-b]pyridin-3-yl]-amide;

1-Pyridin-3-ylmethyl-1H-pyrazole-4-carboxylic acid [4-((R)-3-amino-piperidin-1-yl)-5-methyl-1H-pyrrolo[2,3-b]pyridin-3-yl]-amide;

1-(4-Fluoro-benzyl)-1H-pyrazole-4-carboxylic acid [4-((R)-3-amino-piperidin-1-yl)-5-methoxy-1H-pyrrolo[2,3-b]pyridin-3-yl]-amide;

1-(3-Methyl-benzyl)-1H-pyrazole-4-carboxylic acid [4-((R)-3-amino-piperidin-1-yl)-5-methoxy-1H-pyrrolo[2,3-b]pyridin-3-yl]-amide;

1-(3-Fluoro-benzyl)-1H-pyrazole-4-carboxylic acid [4-((R)-3-amino-piperidin-1-yl)-5-methoxy-1H-pyrrolo[2,3-b]pyridin-3-yl]-amide;

1-(2-Chloro-benzyl)-1H-pyrazole-4-carboxylic acid [4-((R)-3-amino-piperidin-1-yl)-5-methoxy-1H-pyrrolo[2,3-b]pyridin-3-yl]-amide;

1-(2-Methyl-benzyl)-1H-pyrazole-4-carboxylic acid [4-((R)-3-amino-piperidin-1-yl)-5-methoxy-1H-pyrrolo[2,3-b]pyridin-3-yl]-amide;

1-(4-Fluoro-benzyl)-1H-pyrazole-4-carboxylic acid [4-((R)-3-amino-piperidin-1-yl)-5-trifluoromethyl-1H-pyrrolo[2,3-b]pyridin-3-yl]-amide;

1-Benzyl-1H-pyrazole-4-carboxylic acid [4-((R)-3-amino-piperidin-1-yl)-5-trifluoromethyl-1H-pyrrolo[2,3-b]pyridin-3-yl]-amide;

1-Pyridin-3-ylmethyl-1H-pyrazole-4-carboxylic acid [4-((R)-3-amino-piperidin-1-yl)-5-trifluoromethyl-1H-pyrrolo[2,3-b]pyridin-3-yl]-amide; and 1-Pyridin-2-ylmethyl-1H-pyrazole-4-carboxylic acid [4-((R)-3-amino-piperidin-1-yl)-5-trifluoromethyl-1H-pyrrolo[2,3-b]pyridin-3-yl]-amide.

17. The method according to claim 1, wherein the cancer is triple negative breast cancer.

18. The method according to claim 1, wherein the mammal subject is a human subject.

19. The method according to claim 1, wherein the cancer is neuroblastoma.

* * * * *